US009572628B2

(12) United States Patent
Zubiate et al.

(10) Patent No.: US 9,572,628 B2
(45) Date of Patent: Feb. 21, 2017

(54) HIGHLY ARTICULATED PROBES WITH ANTI-TWIST LINK ARRANGEMENT, METHODS OF FORMATION THEREOF, AND METHODS OF PERFORMING MEDICAL PROCEDURES

(71) Applicants: Brett Zubiate, Pittsburgh, PA (US); Arnold Oyola, Northborough, MA (US); Dale Whipple, Taunton, MA (US); Joseph A. Stand, Holden, MA (US); Robert Didomenico, Norfolk, MA (US); William H. Kennefick, Plymouth, MA (US); J. Christopher Flaherty, Auburndale, FL (US)

(72) Inventors: Brett Zubiate, Pittsburgh, PA (US); Arnold Oyola, Northborough, MA (US); Dale Whipple, Taunton, MA (US); Joseph A. Stand, Holden, MA (US); Robert Didomenico, Norfolk, MA (US); William H. Kennefick, Plymouth, MA (US); J. Christopher Flaherty, Auburndale, FL (US)

(73) Assignee: MEDROBOTICS CORPORATION, Raynham, MA (US)

( * ) Notice: Subject to any disclaimer, the term of this patent is extended or adjusted under 35 U.S.C. 154(b) by 0 days.

(21) Appl. No.: 15/064,043

(22) Filed: Mar. 8, 2016

(65) Prior Publication Data

US 2016/0262840 A1    Sep. 15, 2016

Related U.S. Application Data

(63) Continuation of application No. 14/343,915, filed as application No. PCT/US2012/054802 on Sep. 12, 2012.

(Continued)

(51) Int. Cl.
*A61B 34/00* (2016.01)
*A61B 34/30* (2016.01)
(Continued)

(52) U.S. Cl.
CPC ............... *A61B 34/71* (2016.02); *A61B 1/008* (2013.01); *A61B 1/0056* (2013.01); *A61B 34/30* (2016.02);
(Continued)

(58) Field of Classification Search
CPC .............................. A61B 1/008; A61B 1/0055
See application file for complete search history.

(56) References Cited

U.S. PATENT DOCUMENTS 3,060,972 A    10/1962    Sheldon
3,557,780 A    1/1971    Sato
(Continued)

FOREIGN PATENT DOCUMENTS

EP        653922      11/2005
EP       1015068      9/2011
(Continued)

OTHER PUBLICATIONS

Extended European Search Report dated Sep. 16, 2014 issued in European Application No. 12793169.9-1660 / 2713931.
(Continued)

*Primary Examiner* — Terence Boes
(74) *Attorney, Agent, or Firm* — Onello & Mello, LLP

(57) ABSTRACT

An articulating probe, comprises a first mechanism including a first link comprising a first longitudinal axis, a first articulation surface and a first motion-limiting element; and a second link comprising a second longitudinal axis, a second articulation surface and a second motion-limiting element. An articulation joint comprises the first articulation surface and the second articulation surface and constructed
(Continued)

and arranged to allow two degree-of-freedom articulation of the second link relative to the first link. A motion resisting assembly comprises the first motion limiting element and the second motion limiting element, wherein the motion resisting assembly is constructed and arranged to resist rotation of the second link about the second longitudinal axis relative to the first longitudinal axis of the first link.

24 Claims, 29 Drawing Sheets

Related U.S. Application Data

(60) Provisional application No. 61/681,340, filed on Aug. 9, 2012, provisional application No. 61/656,600, filed on Jun. 7, 2012, provisional application No. 61/578,582, filed on Dec. 21, 2011, provisional application No. 61/534,032, filed on Sep. 13, 2011.

(51) Int. Cl.
*B25J 18/06* (2006.01)
*A61B 1/005* (2006.01)
*A61B 1/008* (2006.01)
*B25J 9/06* (2006.01)

(52) U.S. Cl.
CPC ............... *B25J 9/065* (2013.01); *B25J 18/06* (2013.01); *A61B 2034/301* (2016.02); *A61B 2034/305* (2016.02)

(56) References Cited

U.S. PATENT DOCUMENTS

| | | | |
|---|---|---|---|
| 3,572,325 A | 3/1971 | Bazell et al. |
| 3,583,393 A | 6/1971 | Takahashi |
| 3,625,200 A | 12/1971 | Muller |
| 3,638,973 A | 2/1972 | Poletti |
| 3,643,653 A | 2/1972 | Takahashi et al. |
| 3,703,968 A | 11/1972 | Uhrich et al. |
| 3,739,770 A | 6/1973 | Mori |
| 3,790,002 A | 2/1974 | Germond et al. |
| 3,892,228 A | 7/1975 | Mitsui |
| 3,920,972 A | 11/1975 | Corwin, Jr. et al. |
| 4,078,670 A | 3/1978 | Francois et al. |
| 4,108,211 A | 8/1978 | Tanaka |
| 4,150,329 A | 4/1979 | Dahlstrom |
| 4,221,997 A | 9/1980 | Flemming |
| 4,259,876 A | 4/1981 | Belyanin et al. |
| 4,260,319 A | 4/1981 | Motoda et al. |
| 4,299,533 A | 11/1981 | Ohnaka |
| 4,351,323 A | 9/1982 | Ouchi et al. |
| 4,393,728 A | 7/1983 | Larson et al. |
| 4,432,349 A | 2/1984 | Oshiro |
| 4,445,184 A | 4/1984 | Noguchi |
| 4,474,174 A | 10/1984 | Petruzzi |
| 4,475,375 A | 10/1984 | Hill |
| 4,479,914 A | 10/1984 | Baumrucker |
| 4,494,417 A | 1/1985 | Larson et al. |
| 4,496,278 A | 1/1985 | Kaise |
| 4,502,830 A | 3/1985 | Inaba et al. |
| 4,517,963 A | 5/1985 | Michel |
| 4,531,885 A | 7/1985 | Molaug |
| 4,535,207 A | 8/1985 | Lindqvist |
| 4,564,179 A | 1/1986 | Hollingsworth |
| 4,600,355 A | 7/1986 | Johnson |
| 4,655,257 A | 4/1987 | Iwashita |
| 4,661,032 A | 4/1987 | Arai |
| 4,666,366 A | 5/1987 | Davis |
| 4,700,693 A | 10/1987 | Lia et al. |
| 4,706,001 A | 11/1987 | Nakashima et al. |
| 4,726,355 A | 2/1988 | Okada |
| 4,780,045 A | 10/1988 | Akeel et al. |
| 4,787,369 A | 11/1988 | Allred, III et al. |
| 4,790,294 A | 12/1988 | Allred, III et al. |
| 4,796,607 A | 1/1989 | Allred, III et al. |
| 4,804,897 A | 2/1989 | Gordon et al. |
| 4,805,477 A | 2/1989 | Akeel |
| 4,806,066 A | 2/1989 | Rhodes et al. |
| 4,830,569 A | 5/1989 | Jannborg |
| 4,831,547 A | 5/1989 | Ishiguro et al. |
| 4,838,859 A | 6/1989 | Strassmann |
| 4,863,133 A | 9/1989 | Bonnell |
| 4,864,888 A | 9/1989 | Iwata |
| 4,873,965 A | 10/1989 | Danieli |
| 4,888,708 A | 12/1989 | Brantmark et al. |
| 4,900,218 A | 2/1990 | Sutherland |
| 4,941,457 A | 7/1990 | Hasegawa |
| 4,943,296 A | 7/1990 | Funakubo et al. |
| 4,947,827 A | 8/1990 | Opie et al. |
| 4,949,927 A | 8/1990 | Madocks et al. |
| 4,950,116 A | 8/1990 | Nishida |
| 4,956,790 A | 9/1990 | Tsuchihashi et al. |
| 4,979,949 A | 12/1990 | Matsen, III et al. |
| 4,998,916 A | 3/1991 | Hammerslag et al. |
| 5,005,558 A | 4/1991 | Aomori |
| 5,006,035 A | 4/1991 | Nakashima et al. |
| 5,012,169 A | 4/1991 | Ono et al. |
| 5,037,391 A | 8/1991 | Hammerslag et al. |
| 5,044,063 A | 9/1991 | Voellmer |
| 5,046,375 A | 9/1991 | Salisbury, Jr. et al. |
| 5,064,340 A | 11/1991 | Genov et al. |
| 5,078,140 A | 1/1992 | Kwoh |
| 5,086,401 A | 2/1992 | Glassman et al. |
| 5,105,819 A | 4/1992 | Wollschlager et al. |
| 5,108,368 A | 4/1992 | Hammerslag et al. |
| 5,143,475 A | 9/1992 | Chikama |
| 5,167,221 A | 12/1992 | Chikama |
| 5,174,277 A | 12/1992 | Matsumaru |
| 5,176,126 A | 1/1993 | Chikama |
| 5,178,129 A | 1/1993 | Chikama et al. |
| 5,179,935 A | 1/1993 | Miyagi |
| 5,180,276 A | 1/1993 | Hendrickson |
| 5,193,963 A | 3/1993 | McAffee et al. |
| 5,195,968 A | 3/1993 | Lundquist et al. |
| 5,200,679 A | 4/1993 | Graham |
| 5,201,325 A | 4/1993 | McEwen et al. |
| 5,203,380 A | 4/1993 | Chikama |
| 5,203,772 A | 4/1993 | Hammerslag et al. |
| 5,217,003 A | 6/1993 | Wilk |
| 5,217,453 A | 6/1993 | Wilk |
| 5,236,432 A | 8/1993 | Matsen, III et al. |
| 5,251,611 A | 10/1993 | Zehel et al. |
| 5,254,088 A | 10/1993 | Lundquist et al. |
| 5,257,669 A | 11/1993 | Kerley et al. |
| 5,266,875 A | 11/1993 | Slotine et al. |
| 5,271,381 A | 12/1993 | Ailinger et al. |
| 5,297,443 A | 3/1994 | Wentz |
| 5,318,526 A | 6/1994 | Cohen |
| 5,327,905 A | 7/1994 | Avitall |
| 5,337,732 A | 8/1994 | Grundfest et al. |
| 5,386,741 A | 2/1995 | Rennex |
| 5,448,989 A | 9/1995 | Heckele |
| 5,524,180 A | 6/1996 | Wang et al. |
| 5,759,151 A | 6/1998 | Sturges |
| 6,080,181 A | 6/2000 | Jensen et al. |
| 6,132,368 A | 10/2000 | Cooper |
| 6,223,100 B1 | 4/2001 | Green |
| 6,234,958 B1 | 5/2001 | Snoke et al. |
| 6,346,072 B1 | 2/2002 | Cooper |
| 6,440,061 B1 | 8/2002 | Wenner et al. |
| 6,450,948 B1 | 9/2002 | Matsuura et al. |
| 6,743,239 B1 | 6/2004 | Kuehn et al. |
| 6,837,846 B2 | 1/2005 | Jaffe et al. |
| 6,837,847 B2 | 1/2005 | Ewers et al. |
| 6,916,306 B1 | 7/2005 | Jenkins et al. |
| 7,182,764 B2 | 2/2007 | Jenkins et al. |
| 7,682,319 B2 | 3/2010 | Martin et al. |
| 7,789,875 B2 | 9/2010 | Brock et al. |
| 7,850,642 B2 | 12/2010 | Moll et al. |
| 7,854,109 B2 | 12/2010 | Zubiate et al. |
| 7,854,738 B2 | 12/2010 | Lee et al. |

(56) References Cited

U.S. PATENT DOCUMENTS

| | | | |
|---|---|---|---|
| 7,867,241 B2 | 1/2011 | Brock et al. | |
| 7,918,845 B2 | 4/2011 | Saadat et al. | |
| 7,946,546 B2 | 5/2011 | Zubiate et al. | |
| 8,075,476 B2 | 12/2011 | Vargas | |
| 8,100,031 B2 | 1/2012 | Zubiate et al. | |
| 8,123,703 B2 | 2/2012 | Martin et al. | |
| 8,192,422 B2 | 6/2012 | Zubiate et al. | |
| 8,224,485 B2 | 7/2012 | Unsworth | |
| 8,459,138 B2 | 6/2013 | Zubiate et al. | |
| 8,768,509 B2 | 7/2014 | Unsworth | |
| 9,011,318 B2 | 4/2015 | Choset et al. | |
| 2001/0013764 A1 | 8/2001 | Blumenkranz et al. | |
| 2002/0133174 A1 | 9/2002 | Charles et al. | |
| 2002/0161281 A1 | 10/2002 | Jaffe et al. | |
| 2003/0135203 A1 | 7/2003 | Wang et al. | |
| 2004/0044350 A1 | 3/2004 | Martin et al. | |
| 2004/0138529 A1 | 7/2004 | Wiltshire et al. | |
| 2004/0193146 A1 | 9/2004 | Lee et al. | |
| 2005/0033287 A1 | 2/2005 | Sra | |
| 2005/0065397 A1 | 3/2005 | Saadat et al. | |
| 2005/0090811 A1 | 4/2005 | Doyle et al. | |
| 2005/0113640 A1 | 5/2005 | Saadat et al. | |
| 2005/0215992 A1 | 9/2005 | Jenkins et al. | |
| 2005/0216033 A1 | 9/2005 | Lee et al. | |
| 2006/0052664 A1 | 3/2006 | Julian et al. | |
| 2007/0276430 A1* | 11/2007 | Lee | A61B 1/00071 606/205 |
| 2007/0299387 A1 | 12/2007 | Williams et al. | |
| 2008/0027279 A1 | 1/2008 | Abou El Kheir | |
| 2008/0119868 A1 | 5/2008 | Sharp et al. | |
| 2008/0163603 A1 | 7/2008 | Zubiate et al. | |
| 2008/0188869 A1 | 8/2008 | Weitzner et al. | |
| 2008/0245173 A1 | 10/2008 | Schwerin et al. | |
| 2008/0275300 A1* | 11/2008 | Rothe | A61B 1/0008 600/129 |
| 2009/0030428 A1 | 1/2009 | Omori et al. | |
| 2009/0171151 A1* | 7/2009 | Choset | A61B 1/00006 600/114 |
| 2009/0326556 A1 | 12/2009 | Diolaiti et al. | |
| 2010/0022825 A1 | 1/2010 | Yoshie | |
| 2010/0130924 A1 | 5/2010 | Martin et al. | |
| 2010/0160735 A1 | 6/2010 | Bakos | |
| 2010/0160736 A1 | 6/2010 | Padget et al. | |
| 2010/0204713 A1 | 8/2010 | Ruiz Morales | |
| 2010/0224022 A1 | 9/2010 | Choi et al. | |
| 2010/0280325 A1 | 11/2010 | Ibrahim et al. | |
| 2011/0028790 A1 | 2/2011 | Farr et al. | |
| 2011/0056320 A1 | 3/2011 | Zubiate et al. | |
| 2011/0152613 A1 | 6/2011 | Zubiate et al. | |
| 2011/0184241 A1 | 7/2011 | Zubiate et al. | |
| 2011/0213384 A1 | 9/2011 | Jeong | |
| 2011/0313243 A1* | 12/2011 | Zubiate | A61B 17/00234 600/104 |
| 2012/0209073 A1 | 8/2012 | McWeeney et al. | |
| 2013/0150673 A1 | 6/2013 | Kakehashi | |
| 2014/0088356 A1 | 3/2014 | Matsuo et al. | |
| 2015/0164491 A1 | 6/2015 | Choset et al. | |
| 2016/0174816 A1 | 6/2016 | Choset et al. | |

FOREIGN PATENT DOCUMENTS

| | | |
|---|---|---|
| JP | 5921756 | 5/1984 |
| JP | 0622905 | 2/1994 |
| JP | 2007511247 | 5/2007 |
| JP | 2007511248 | 5/2007 |
| JP | 2008504072 | 2/2008 |
| WO | 2007134461 | 11/2007 |
| WO | 2010050771 | 5/2010 |

OTHER PUBLICATIONS

PCT ISRWO dated May 19, 2014, issued in International application No. PCT/US2014/010808.

Expo-70 Robot—Vadim Matskevich's students, http://cyberneticzoo.com/wp-content/uploads/2010/03/Expo-70-MK-1969-02-p31-3.pdf, 1969.

Conductor Robot, http://cyberneticzoo.com/wp-content/uploads/2010/03/Ticket-robot-russian-1973.pdf, 1973.

Michael L. Rhodes, "Computer Graphics and an Interactive Stereotactic System for CT-Aided Neurosurgery", IEEE Computer Graphics and Application, Computer Graphics in Medicine & Biology, 1983, p. 31-37.

Lee E. Weiss, Arthur C. Sanderson, Charles P. Neuman, "Dynamic Sensor Based Control of Robots with Visual Feedback", IEEE Journal of Robotics and Automation, 1987, p. 404-417.

Jean-Jacques E. Slotine, Weiping Li, "Composite adaptive control of robot manipulators", Automatica; Nonlinear Systems Laboratory, Massachusetts Institute of Technology, Cambridge, MA 02139, U.S.A., 1989, p. 509-519.

Weiping Li, Jean-Jacques E. Slotine, "An indirect adaptive robot controller", Systems & Control Letters; Nonlinear Systems Laboratory, Massachusetts Institute of Technology Cambridge, MA 02139, U.S.A., 1989, p. 259-266.

Xu Hongbin, "Stability and performance robustness analysis of hybrid control for robot manipulators", Journal of UEST of China, vol. 22 No. 5, Oct. 1993, p. 501-505.

Francois Chaumette, Patrick Rives, Bernard Espiau, "Positioning of a Robot With Respect to an Object, Tracking It and Estimating Its Velocity by Visual Servoing", IEEE International Conf. on Robotics and Automation, 1991, p. 2248-2253.

A.V. Timofejev, N.V. Ivanova, "Expert System of the Control Programs Designing of Adaptive Robots", The Lenigrand Institute of Aircraft Instrumentation, 1991, p. 912-915.

W Szczepiński, "Theory of polyhedrons of positioning accuracy of manipulators", Mechanism and Machine Theory; Institute of Fundamental Technological Research, Polish Academy of Sciences, 00-049 Warsaw, Swietokrzyska 21, Poland, 1991, p. 697-709.

Junji Furusho, Hiroshi Nagao, Naruse Makoto, "Multivariable Root Loci of Control Systems of Robot Manipulators with Flexible Driving Systems : Distortion Feedback", JSME International Journal, 1992, p. 65-73.

Potemkin, E., Astafurov, P., Osipov, A., Malenkov, M., Mishkinyuk, V., Sologub, P., "Remote-controlled robots for repair and recovery in the zones of high radiation levels", Robotics and Automation, IEEE, 1992, p. 80-82.

S. L. Shishkin, "Adaptive control of a biped robot walking across a horizontal plane", International Journal of Adaptive Control and Signal Processing, 1992, p. 259-264.

Henk Nijmeijer, "Global regulation of robots using only position measurements", Systems and Control Letters; Department of Electrical Engineering, Mechatronics Research Centre Twente, University of Twente, P.O. Box 217, 7500 AE Enschede, Netherlands, 1992, p. 289-293.

Hitoshi Maekawa, Kazuhito Yokoi, Kazuo Tanie, Makoto Kaneko, Nobuo Kimura, Nobuaki Imamura, "Development of a three-fingered robot hand with stiffness control capability", Mechatronics; Mechanical Engineering Laboratory, 1992, p. 483-494.

J.D. Moon, D.W. Cho, "A component mode synthesis applied to mechanisms for an investigation of vibration", Journal of Sound and Vibration; Department of Mechanical Engineering, Pohang Institute of Science and Technology, Pohang, Korea, 1992, p. 67-79.

Timopheev, A.V., Prokhorov, D.V., "Neural networks processing systems in recognition and control problems", Neuroinformatics and Neurocomputers; IEEE, 1992, p. 820-828.

Jianguo Fu, Naresh K. Sinha, "An iterative learning scheme for motion control of robots using neural networks: A case study", Journal of Intelligent & Robotic Systems, 1993, p. 375-398.

Troccaz, J. Lavallee, S. Hellion, E., "A passive arm with dynamic constraints: a solution to safety problems in medical robotics", Systems Engineering in the Service of Humans, Conference Proceedings, 1993, p. 166-171.

Swarup, M. Gopal, "Comparative study on linearized robot models", Journal of Intelligent & Robotic Systems, 1993, p. 287-300.

H. Azaria, A. Dvir, "Algorithm optimization using a rule-based system. A case study: The Direct Kinematic Solution in robotics", Journal of Intelligent & Robotic Systems, 1993, p. 309-324.

(56) References Cited

OTHER PUBLICATIONS

Erick Garcia-Benitez; Stephen Yurkovich; Kevin M. Passino, "Rule-Based Supervisory Control of a Two-Link Flexible Manipulator", Journal of Intelligent and Robotic Systems, 1993, p. 195-213.
K. Periyasamy, V. S. Alagar, T. D. Bui, "A formal framework for design and verification of robotic agents", Journal of Intelligent & Robotic Systems, 1993, p. 173-200.
S. Nicosia, A. Tornambè, P. Valigi, "State estimation in robotic manipulators: Some experimental results", Journal of Intelligent & Robotic Systems,, 1993, p. 321-351.
Dimitrios M. Emiris, Vassilios D. Tourassis, "Singularity-robust decoupled control of dual-elbow manipulators", Journal of Intelligent & Robotic Systems, 1993, p. 225-243.
M.M. Bayoumi, "Adaptive Control of Robots with Rigid Links: A Status Report", Department of Electrical Engineering, Queen's University, Ontario, Canada (IEEE), 1993, p. 232-236.
Y. Edan, B. A. Engel, G. E. Miles, "Intelligent control system simulation of an agricultural robot", Journal of Intelligent & Robotic Systems, 1993, p. 267-284.
Chun-Yi Su, "Adaptive sliding mode control of nonlinear robotic systems with time-varying parameters", Systems and Control Letters; Department of Mechanical Engineering, University of Victoria, Victoria, B.C. Canada V8W 3P6, 1993, p. 35-41.
Yalou Huang; Guizhang Lu, "Force Analysis and Hybrid Control Scheme for Multiple Robot Manipulators", Artificial Intelligence and Robotics Research Laboratories; Dept of Computer and System Sciences; Nankai University, China (Proceedings of the 1993 IEEE/RSJ International Conference on Intelligent Robots and Systems in Japan), 1993, p. 1530-1534.
C.M. Lim; T. Hiyama, "Experimental implementation of a fuzzy logic control scheme for a servomotor", Mechatronics; Department of Electronic Engineering, Ngee Ann Polytechnic, Singapore 2159 Singapore.
E. Al-Gallaf, A.J. Allen, K. Warwick, "Dextrous hands: Issues relating to a four-finger articulated hand", Mechatronics; Department of Cybernetics, School of Engineering and Information Sciences, University of Reading, Reading, Berks RG6 2AY, U.K., 1993, p. 329-342.
A. Swarup, M. Gopal, "On robustness of decentralized control for robot manipulators", Robotics and Autonomous Systems; Department of Electrical Engineering, Indian Institute of Technology, New Delhi—110016, India, 1993, p. 109-112.
L. Behera, M. Gopal, Santanu Chaudhury, "Trajectory tracking of robot manipulator using Gaussian networks", Dept. of Electrical Engineering, Indian Institute of Technology, Delhi, Hauz Khas, New Delhi 110 016, India, 1993.
E. V. Panteley, A. A. Stotsky, "Adaptive trajectory/force control scheme for constrained robot manipulators", International Journal of Adaptive Control and Signal Processing, 1993, p. 489-496.
Filaretov, V.F., "A Synthesis of Adaptive Control Systems for Industrial Robots", Electronic Mfg Technology Symposium, 1993, p. 168-171.
S. Zenkevich, A. Maximov, A. Nazarova, A. Korshunov, "Control of robot-based assembly cell", Lecture Notes in Control and Information Sciences , 1993, p. 418-427.
D.E. Whitney, "The Mathematics of Coordinated Control of Prosthetic Arms and Manipulators", Asme Publication, 1972.
Shapiro, "Digital Technology Enables Robots to See", Computer Design, 1978.
Bejczy, A. K., Salisbury, Jr., J. K., "Kinesthetic Coupling Between Operator and Remote Manipulator", Advances in Computer Technology, 1980.
"An Improved CT-Aided Stereotactic Neurosurgery Technique", Fifth Annual Symposium on Computer Applications in Medical Care, 1981, p. 591-595.
Michael L. Thodes, Ph.D, "Stereotactic Neurosurgery Using 3D Image Data From Computed Tomography", Journal of Medical Systems, 1982, p. 106-118.
Salisburg, Jr., J. Kenneth, "Kinematic and Force Analysis of Articulated Hands", 1982.
"Minicomputer Control Robot's Six Electrohydraulic Servoactuators", Hydraulics & Pneumatics, 1982, p. 53-58.
F.M. Kulakov, "Modeling Robot Control in Assembly Operations", Modern Robot Engineering, Moscow, MIR Publishers, 1982, p. 100-116.
Bejczy et al., "Controlling Remote Manipulators Through Kinesthetic Coupling", Computers in Mechanical Engineering, 1983, p. 48-60.
L.E. Weiss, "Dynamic Visual Servo Control of Robots: an adaptive image-based approach, Technical Report", Carnegie Mellon, 1984.
Dennis E. Bullard, "CT-Guided Stereotactic Biopsies Using a Modified Grame and Gildenberg Techniques", Journal of Neurology, Neurosurgery and Psychiatry, 1984, p. 590-595.
M. Caporali et al., "Design and Construction of a Five Fingered Robotic Hand", Robotics Age, 1984, p. 14-20.
Salisbury, Jr., J. K., "Design and Control of an Articulated Hand", International Symposium on Dessign and Synthesis, 1984.
L. Dade Lunsford, M.D., "Stereotactic Exploration of the Brain in the Era of Computed Tomography", Surg. Neurol, 1984, p. 222-230.
Jacobsen, S.C., Iversen, E.K., Knutti, D. F., Johnson, R.T., Biggers, K. B., "Design of the Utah/MIT Dexterous Hand", Conf. on Robotics and Automation, 1986.
S. Hayati, M. Mirmirani, "Improving the Absolute positioning Accuracy of Robot Manipulators", Journal of Robotic Systems, 1986, p. 397-413.
Vertut, J., Coiffet, P., "Teleoperations and Robotics Evolution and Development", Robot Technology, 1986, p. 191-194.
L.E. Weiss; A.C. Sanderson, "Dynamic Sensor-based Control of Robots with Visual Feedback", IEEE Journal of Robotics and Automation, 1987, p. 5.
Townsend, W.T., Salisbury, Jr. J. K., "The Effect of Coulomb Friction and Stiction on Force Control", Conf. on Robotics and Automation, 1987.
P. Rives, F. Chaumette, B. Espiau, "Visual Servoing Based on a Task Function Approach", International Symposium on Experimental Robotics (Canada), 1989.
B.L. Davies, R.D. Hibberd, A. Timoney, J.E.A. Wickham, "A surgeon robot for prostatectomies", Proc. of 2nd Int. Conference on Robotics in Medicine (UK), 1989.
J.T. Feddema, C.S.G. Lee, O.R. Mitchell, "Automatic selection of image features for visual servoing of a robot manipulator", Conf. IEEE Robotics and Automation (USA), 1989, p. 14-19.
J.T. Feddema, O.R. Mitchell, "Vision-Guided Servoing with Feature-Based Trajectory Generation", IEEE Transaction on Robotics and Automation, 1989.
Pierre J. de Smet, Eugene I. Rivin, Yongle Lou, D. Kegg, "Robot Performance as Influenced by Mechanical System", CIRP Annals—Manufacturing Technology, 1990, p. 383-386.
Mills, J.K., "Hybrid actuation of robotic manipulators: an integral manifold control approach", Intelligent Control, IEEE, 1990, p. 817-823.
John T. Feddema, C. S. George Lee, "Adaptive Image Feature Prediction and Control for Visual Tracking with a Hand-eye Coordinated Camera", IEEE Transactions on Systems, man, and Cybernetics, 1990, p. 1172-1183.
Rafiqul I. Noorani, "Microcomputer-based robot arm control", Mathematical and Computer Modelling, 1990, p. 450-455.
Elysseev S., Kuznetzov, N., Lukyanov A., "Control of Robot Vibrations", 1990.
C. Samson, B. Espiau, "Robot Control: The Task Function Approach", Oxford Univ., 1990.
Adams, L, Krybus, W., Meyer-Ebrecht, D., Rueger, R., Gilsbach, J.M., Moesges, R., Schloendorff, G., "Computer Assisted Surgery", IEEE Computer Graphics and Application, 1990, p. 43-51.
B. Espiau, F. Chaumette, P. Rives, "A new approach to visual servoing in robotics", Research Report; IRISA/INRIA (France), 1990.
Korikov, Anatoliim, Syriamkin, Vladimiri, Titov, Vitaliis, "Correlation robot vision systems", 1990, p. 264.
Sadegh N, Hopowitz R, "Stability and robustness analysis of a class of adaptive controller for robotic manipulator", The International Journal of Robotics Research, 1990.

(56) References Cited

OTHER PUBLICATIONS

Rocheleau, D.N., Crane, C.D., III, "Development of a graphical interface for robotic operation in a hazardous environment", Systems, Man, and Cybernetics, 1991, p. 1077-1081.
J.C. Latombe, "Robot Motion Planning", The Kluwer International Series in Engineering and Computer Science, Kluwer Academic Publishers, 1991.
Kubota, T., Sato, M., Harashima, F., "Visual Control of Robotic Manipulator Based on Neural Networks", Industrial Electronics, IEEE, 1992, p. 490-496.
Nakamura, H., Shimada, T., Kobayashi, H., "An inspection robot for feeder cables-snake like motion control", Industrial Electronics, Control, Instrumentation, and Automation, 1992, p. 849-852.
P. Kazanzides, J. Zuhars, B. Mittelsstadt, R.H. Taylor, "Force sensing and control for a surgical robot", IEEE conference on Robotics and Automation (Nice), 1992, p. 612-617.
Vsevolod I. Astafyev Farus, Yakutsk, Russia Yuri M. Gorsky, "Homeostatics", Cybernetics and applied systems, 1992, p. 7-22.
S. Lavallee, J. Troccaz, L. Gaborit, A.L. Benabid, D. Hoffman, "Image guided operating robot: A clinical application in stereotactic neurosurgery", IEEE Conference on Robotics and Automation (Nice), 1992.
H.A. Paul, B. Mittelstadt, W.L. Bargar, B. Musits, R.H. Taylor, P. Kazanzides, J. Zuhars, B. Williamson, W. Hanson, "A surgical robot for total hip replacement surgery", IEEE Conference on Robotics and Automation (Nice), 1992, p. 606-611.
R.H. Taylor, et. al, Augmentation of Human Precision in Computer-Integrated Surgery, Innov. Tech. Biol. Med., 1992.
Takashi Matsui, Mochizuki Yoshihiro, Effect of Positive Angular Velocity Feedback on Torque Control of Hydraulic Actuator, JSME international journal, 1992, p. 406-412.
Ph, Cinquin, et. al, IGOR: Image Guided Operating Robot. Methodology, Medical Applications, Results, Innov. Tech. Biol. Med., 1992, p. 1048-1049.
Heung-Joo Jeon, Bum-Hee Lee, Robot Motion Planning for Time-Varying Obstacle Avoidance Using the Distance Function, 1992, p. 1429-1438.
Bose, B., Kalra, A.K., Thukral, S., Sood, A., Guha, S.K., Anand, S., Tremor Compensation for Robotics Assisted Microsurgery, Engineering in Medicine and Biology Society, 1992, p. 1067-1068.
Kenneth L. Hillsley, Stephen Yurkovich, Vibration Control of a Two-Link Flexible Robot Arm, Dynamics and Control, 1993, p. 261-280.
Canudas de Wit, C., Ortega, R., Seleme, S.I., Robot Motion Control Using Induction Motor Drives, Robotics and Automation, 1993, p. 533-538.
Alberto Rovetta, Xia Wen, Telemanipulation Control of a Robotic Hand With Cooperating Fingers by Means of Telepresence With a Hybrid Virtual-Real Structure, RoManSy 9: Proceedings of the Ninth CISM-IFToMM Symposium on Theory and Practice of Robots and Manipulators, 1993, p. 411-417.
James K. Mills, Hybrid Actuator for Robot Manipulators: Design, Control and Performance, Robotics and Automation, IEEE Conference, 1993, p. 19-38.
Pietro Fanghella, Carlo Galletti, An Approach to Symbolic Kinematics of Multiloop Robot Mechanisms, RoManSy9, 1993, p. 33-40.
Yozo Fujino, Pennung Warnitchai, B.M. Pacheco, Active Stiffness Control of Cable Vibration, Journal of Applied Mechanics, 1993, p. 948-953.
Ng, W.S. Davies, B.L. Hibberd, R.D. Timoney, A.G., Robotic Surgery, Engineering in Medicine and Biology Magazine, 1993, p. 120-125.
J.L. Dallaway, R.M. Mahoney, R.D. Jackson, R.G. Gosine, An Interactive Robot Control Environment for Rehabilitation Applications, Robotica, 1993, p. 541-551.
Giulio E. Lancioni, Domenico Bellini, Doretta Oliva, "A robot to provide multi-handicapped blind persons with physical guidance and activity choices", Journal of Developmental and Physical Disabilities, 1993, p. 337-348.

Melzer A, Schurr MO, Kunert W, Buess G, Voges U, Meyer JU., Intelligent Surgical Instrument System ISIS. Concept and Preliminary Experimental Application of Components and Prototypes, Endosc Surg Allied Technol., 1993, p. 165-170.
John G. Hunter, Jonathan M. Sackier, Minimally Invasive Surgery, McGraw Hill, Inc., Health Professions Division, 1993.
Zhao Yu-shan Gu Liang-xian , Generalized Dynamic Model for Multibodies Manipulator, 1993.
F.M. Kulakov, Russian Research on Robotics, Intelligent Autonomous Systems, 1995, p. 53-62.
Shevtsova N.A., Faure A., Klepatch A.A., Podladchikova L.N., Rybak I.A. , Model of Foveal Visual Preprocessor, Intelligent Robots and Computer Vision XIV: Algorithms, Techniques, Active Vision, and Materials Handling, 1995, p. 588-596.
Reynolds, O., "On Efficiency of Belts or Straps as Communicators of Work", The Engineer, 1874, p. 396.
Swift, H. W., "Power Transmission by Belts: An Investigation of Fundamentals", The Institution of Mechanical Engineers, 1928.
Smith, G. A. et al., "Surgery", 1950, p. 817-821.
"Baby Robot", http://cyberneticzoo.com/wp-content/uploads/2010/03/Ticket-robot-russian-1973.pdf, 1970.
Rajac, "Variable-Pitch Transfer Mechanism", IBM Technical Disclosure Bulletin, 1974.
Zh Luo , "Theoretical and Experimental Study on Control of Flexible Robot Arms Using Direct Strain Feedback", 1992.
Bu Yonghong, Wang Yi, "The Identification of Geometric Link Parameters of Robot Manipulators", ACTA Automatica Sinica, 1992.
Zheng Nanning Wang Long Hu chao Liu Jianqin, "Improved BP Neural Net and Its Application to Handwritten Numeral Recognition", 1992.
Stefano Chiaverini, Bruno Siciliano, Olav Egeland, Robot Control in Singular Configurations—Analysis and Experimental Results, Experimental Robotics II, 1993, p. 25-34.
Antonio Bicchi, J. Kenneth Salisbury, David L. Brock, Experimental Evaluation of Friction Characteristics With an Articulated Robotic Hand, Experimental Robotics II, 1993, p. 153-167.
Claudio Melchiorri, Gabriele Vassura, Mechanical and Control Issues for Integration of an Arm-Hand Robotic System, Experimental Robotics II, 1993, p. 136-152.
Andrew K. Rist, Ellen Y. Lin, Bartholomew O. Nnaji, Ralph Application for Surface Mount Assembly, International Journal of Flexible Manufacturing Systems, 1993, p. 27-52.
R.H. Taylor, et. al, A Model-Based Optimal Planning and Execution System With Active Sensing and Passive Manipulation for Augmentation of Human-Precision in Computer-Integrated Surgery, Lecture Notes in Control and Information Sciences; Experimental Robo.
Nobuyuki Furuya, Masatomo Matubara, An Algorithm of Motor Control by Software Servo System (2nd Report): Application to 4-Axes SCARA Robot, Journal of the Japan Society of Precision Engineering , 1993, p. 423-428.
H.S. Moon, S.Y. Lee, S.J. Na, A Study on Selection of Gas Metal Arc Welding Parameters of Fillet Joints Using Neural Network, Journal of the Korean Welding Society, 1993, p. 151-160.
Byong Suk Kim, Computer-Assisted System for Accident Analysis and Mul-Function Protection in Industrial Robot, Papersearch.net (Korean Studies Information Co.), 1993, p. 61-64.
J. I. Arocena, R. W. Daniel, P. Elosegui, End Point Control of Compliant Robots, Experimental Robotics II, 1993, p. 435-449.
Ho Kyung Kim, Nonlinear Static Analysis and Determination of Initial Equilibrium States of Suspension Bridges, 1993, p. 177-186.
Gimdongha, imhyeongyo (Dong Ha Kim, Hyeon Kyo Lim) , Safe Speed Limit of Robot Arm During Teaching and Maintenance Work, 1993, p. 64-70.
Chang-Boo Kim, Seung-Hoon Lee, Inverse Dynamic Analysis Of a Flexible Robot Arm With Multiple Joints by Using the Optimal Control Method, Journal of the Korean Society of Precision Engineering , 1993, p. 133-140.
Chang-Soo Han, The Optimum Design of a 6 D.O.F. Fully-Parallel Micromanipulator for Enhanced Robot Accuracy, Journal of the Korean Society of Precision Engineering , 1993, p. 42-51.

(56) References Cited

OTHER PUBLICATIONS

Nicholas Jackson, The Story Behind the Russian Robot Collie Patent Sketches, The Atlantic, 2011.
Oh Joong Chan, Jong Sik Boong, Choi Ko Bong, Kwon Key Jo, Design a Mobile Robot's Tracking Control System Using Fuzzy Theory, Sung Kyun Kwan Univ., 1992, p. 112-115.
Sang-Gwon Lim, Jin-Won Lee, Yong-Ky Moon, Dong-Lyeol Jeon, Sang-Hyun Jin, In-Hwan Oh, Dong-Il Kim, Sung-Kwun Kim, Development of AC Servo Motor Controller for Industrial Robot and CNC Machine System, Control R/D Team, Samsung Electronics, 1992, p. 1211-1214.
E.S. Jeon, S.H. Park, J.E. Oh, Singylarty Control of Robot Wrist Joints Using Euler Parameters, Journal of the Korean Society of Precision Engineering , 1992, p. 11-152.
Yoon Seok Chang, Hakil Kim, Motion Estimation of Moving Objects Using Frequency Domain Transforms, 1992, p. 92-99.
Nam Gu Lee, Chong Soo Lee, Chong Kug Park, Dynamic Hybrid Position/Force Controller for Two Cooperating Robots, 1992, p. 103-107.
Jong-Wu Moon, Jeung Park, Chong-Xuk Park, Adaptibe Control of a Flexible Robot Manipulator—Using ARMA Prediction Model, 1992, p. 122-127.
Dae-Gab Gweon, Choong-Min Jung, Development of a Robot Wrist for the Assembly of Chamferless Parts, Journal of the Korean Society of Precision Engineering , 1992, p. 36-43.
Fumio Harashima, Yaskuhiko Dote, Sensor-Based Robot Systems, Proc. IEEE Int. Symposium; Muroran Institute of Tech. (Japan), 1992, p. 10-19.
Chang-Boo Kim, Seung-Hoon Lee, Formulation of the Equation of Motion for Flexible Robotics Arms by Using the Finite Element Method, Inha Univ., Daewoo Heavy Industries LTD, 1992, p. 233-238.
Jin-Geol Kim, A Study on the Robust Digital Tracking Control of a Robot With Flexible Joints, Journal of the Korean Society of Precision Engineering , 1992, p. 92-100.
Han-Sig Lee, The Prospects for the Future on Research of Flexible Automation and Robot System, 1992, p. 37-38.
Young Hood Joo, Seok Joo Yi, San Yeob Cha, Kwang Bang Woo, Hyung Woo Yoon, Gun Woong Hae, Sung Kwun Kim, A Study on Optimal Navigation of Autonomous Mobile Robot, Production of Eng. Division, Samsung Electronics Co., 1992, p. 128-133.
H. C. Shen, W. P. Yan, G. E. Taylor, Intelligent Sensory Decision-Making for Error Identification in Autonomous Robotics Systems, The International Journal of Advanced Manufacturing Technology, 1993, p. 377-384.
Morris R. Driels, W. Swayze, S. Potter, Full-Pose Calibration of a Root Manipulator Using a Coordinate-Measuring Machine, The International Journal of Advanced Manufacturing Technology, 1993, p. 34-41.
M. Wu, B. C. Jiang, Y. R. Shiau, Controlling a Robot's Position Using Neural Networks, The International Journal of Advanced Manufacturing Technology, 1993, p. 216-226.
Joachim O. Berg, Path and Orientation Accuracy of Industrial Robots, The International Journal of Advanced Manufacturing Technology, 1993, p. 29-33.
Shaheen Ahmad, Mohamed Zribi, Lyapunov-Based Control Design for Multiple Robots Handling a Common Object, Dynamics and Control, 1993, p. 127-157.
S.D. Park, K.W. Jeong, W.K. Chung, Y. Youm, Development of a Control Method Using Both Electric and Pneumatic Actuators for a Heavy Load Handing Robot, Journal of the Korean Society of Precision Engineering , 1993, p. 14-21.
Nicolay V. Kim, Algorithms of Observation Information Synthesis, International Conference on Electronics, Informations and Communications, 1993, p. 120-124.
Sung Do Chi, Seok Pil Lee, Wang Jae Lee, San Hui Park, Hierarchical Design of Intelligent Robot System, Hankuk Aviation Univ., Yonsel Univ., 1993, p. 213-216.
Cai Zi-Xing, Jiang Zhiming, High-Level Expert System-Based Robot Planning, 1993.
Yong-Deuk Seo, Dong-Joon Choi, Ki-Sang Hong, Hong Joeng, The Development of Intelligent Robot Using Vision and Speech Recognition System, Department of EE, Postech, 1993, p. 39-44.
Jae-Hun Jung, Yong-Hyun Jung, Jong-Mo Kim, Suck-Gyu Lee, Dal-Hae Lee, Motion Control of Autonomous Mobile Robot With Fuzzy Algorithm, Yeungnam Univ., 1993, p. 362-365.
Jin-Seob Choi, Dong-Won Kim, Sung-Mo Yang, A Study on the Pseudoinverse Kinematic Motion Control of 6-Axis Arc Welding Robot, Journal of the Korean Society of Precision Engineering , 1993, p. 170-177.
A Study on a Basic System Configuration for the PC Interface and the Robot Trajectory Generation, 1993, p. 354-358.
G.T. Yang, S.D. Ahn, S.C. Lee, Tip Position Control of Flexible Robot Arm by Self-Tuning Fuzzy Algorithm, Chonbuk Univ., 1993, p. 213-217.
Jeong Park, Hoe-Young Yoo, The Study of the Method of Position Control for the One-Link Flexible Robot Arm, 1993, p. 57-60.
ASEA Industrial Robot System IRb-60, 1975, p. 1-8.
Robots Take a Hold on Production, 1982, p. 122-129.
M. Peter Heilburn, M.D., J., Preliminary Experience With Brown-Robert-Wells (BRW) Computerized Tomography Stereotaxis Guidance System, Neurourgery, 1983, p. 217-221.
International Machine Intelligence Robot System Users Manual, International Machine Intelligence, 1983.
Orbitran Wafer Handling Robot, Genmark Automation, 1989, p. 2,3,4.
H Kojima, R Toyama, Development of Wall Cleaning Robot, 1992.
International Search Report and Written Opinion dated Nov. 28, 2012, issued in related International Application No. PCT/US2012/040414.
International Search Report and Written Opinion dated Feb. 27, 2013, issued in related International Application No. PCT/US2012/054802.
International Search Report and Written Opinion dated Apr. 25, 2013, issued in related International Application No. PCT/US2012/070924.
International Search Report and Written Opinion dated Apr. 6, 2012 issued in related International Application No. PCT/US2011/044811.
International Search Report and Written Opinion dated May 31, 2012, issued in related International Application No. PCT/US2011/060214.
Australia Office Action dated Jun. 19, 2014, issued in related Australia Application No. 2011283048.
International Search Report and Written Opinion dated Dec. 9, 2013, issued in related International Application No. PCT/US2013/054326.
International Search Report and Written Opinion dated May 30, 2012, issued in related International Application No. PCT/US2011/057282.
Office Action and English summary from related Chinese application 201280055547.0 dated Apr. 9, 2015.
Extended European Search Report dated Jun. 6, 2015 in related EP Application No. 12832524.8.
Office Action dated Feb. 16, 2016 issued in corresponding China Application No. 2012-80055547.0, with English language summary.
Office Action issued on Jul. 28, 2016 in related Australian application No. 2012308731.
Office Action dated Aug. 23, 2016 in corresponding Japanese Application No. 2014-530749 with English language summary.
Office Action dated Nov. 25, 2016 issued in corresponding European Application No. 12832524.8.

\* cited by examiner

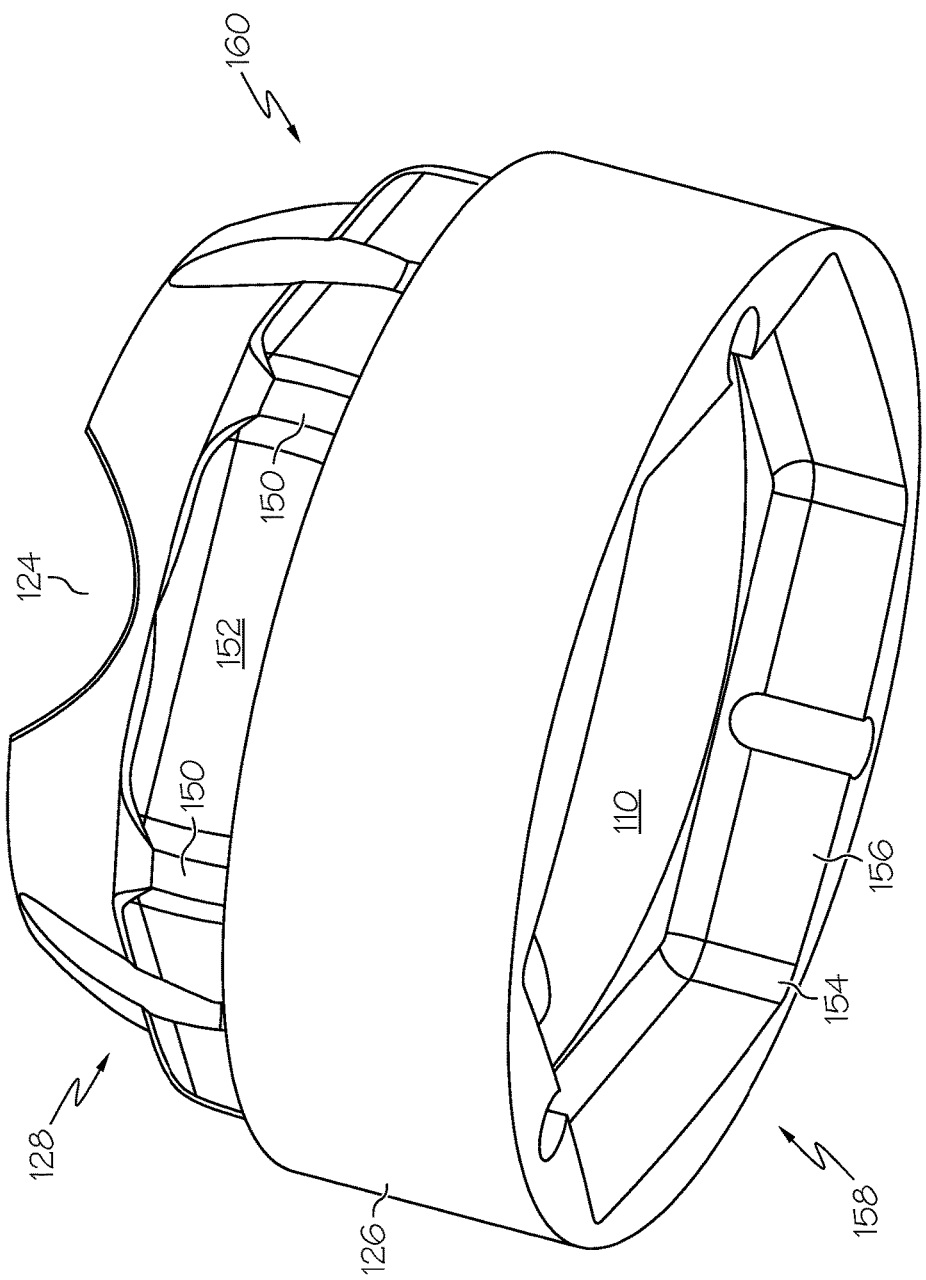

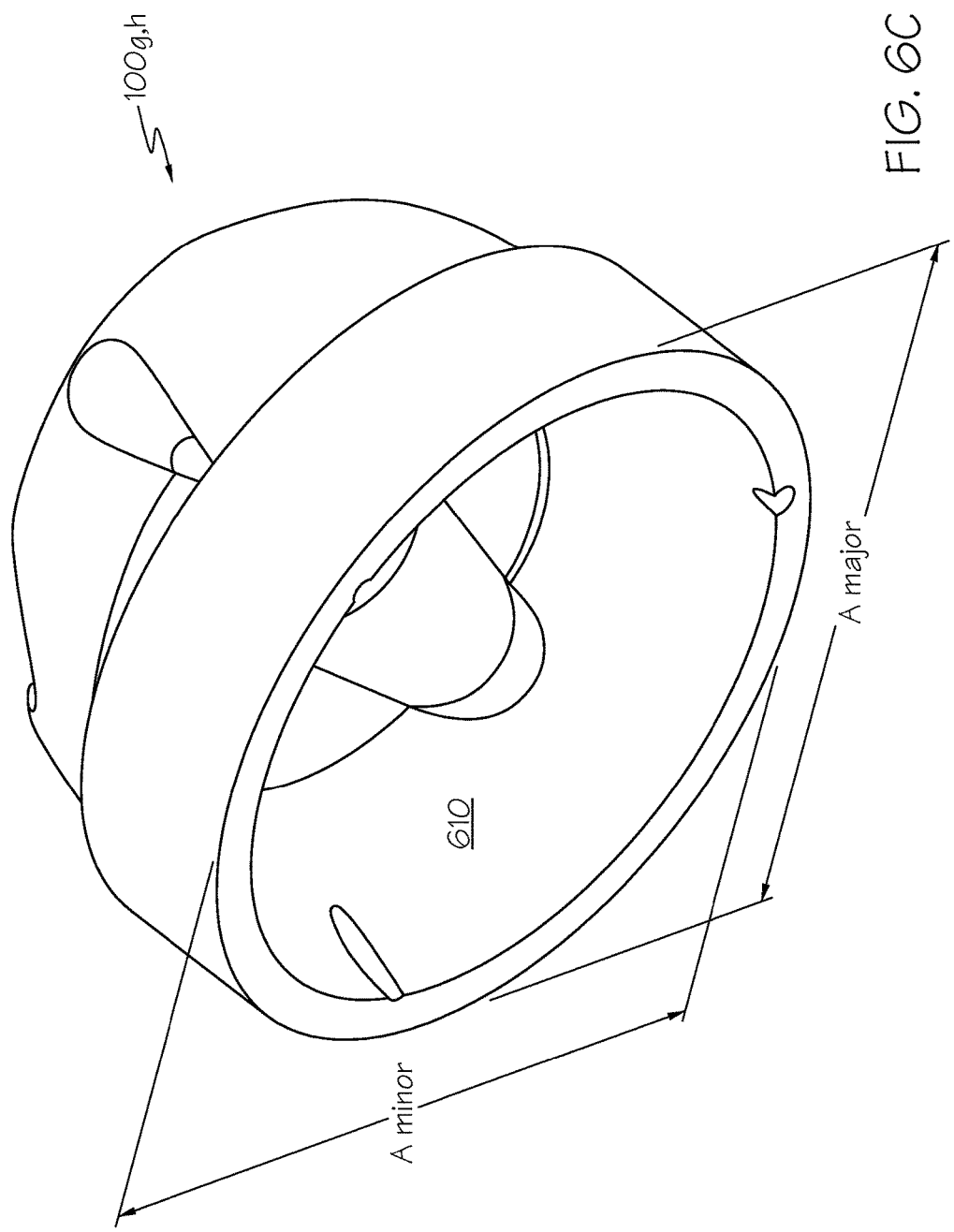

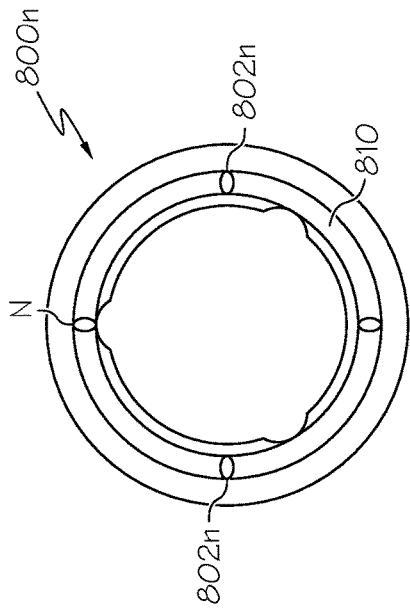
FIG. 8B(1)
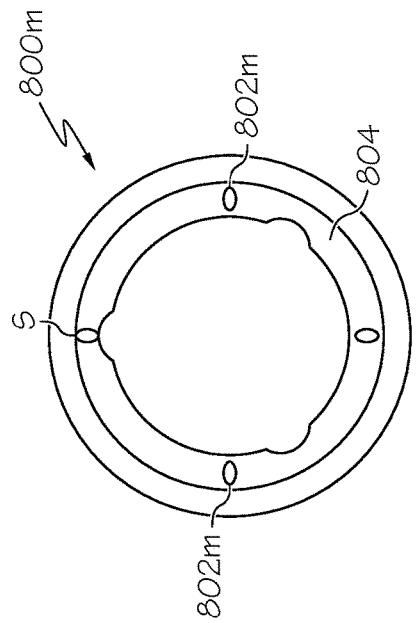
FIG. 8B(2)
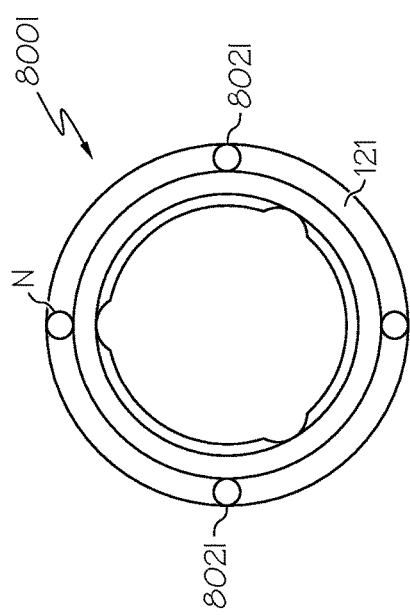
FIG. 8A(1)
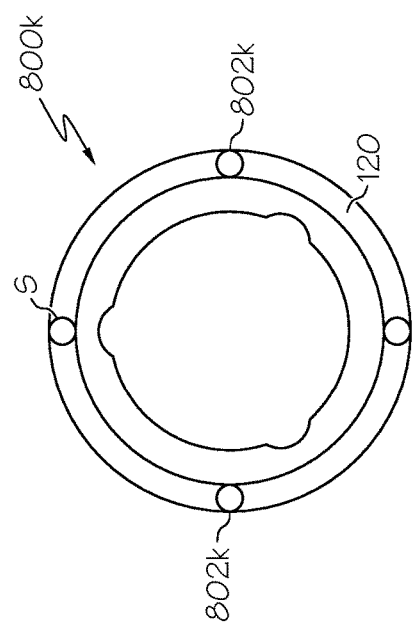
FIG. 8A(2)

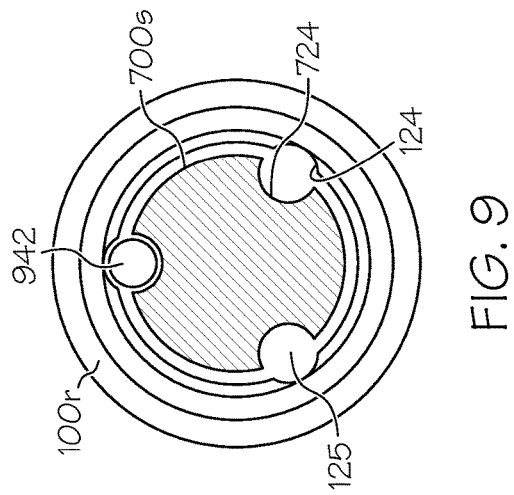
FIG. 9
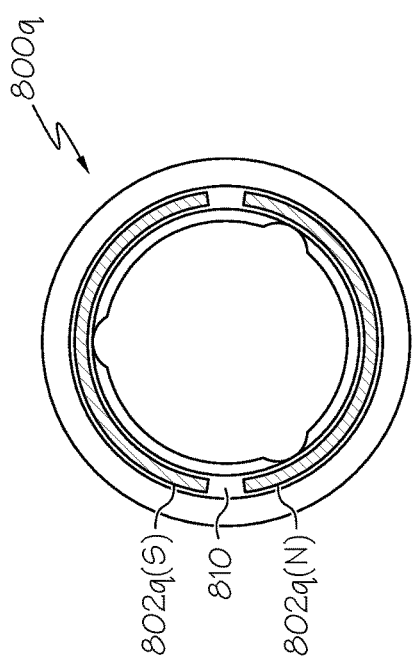
FIG. 8C(1)
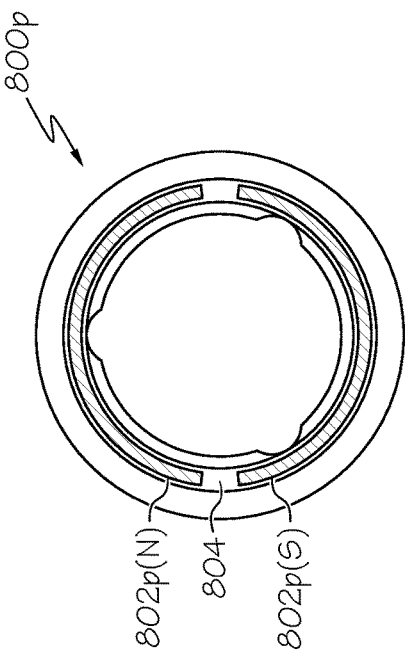
FIG. 8C(2)

HIGHLY ARTICULATED PROBES WITH ANTI-TWIST LINK ARRANGEMENT, METHODS OF FORMATION THEREOF, AND METHODS OF PERFORMING MEDICAL PROCEDURES

RELATED APPLICATIONS

This application is a continuation application of U.S. application Ser. No. 14/343,915, filed Mar. 10, 2014, which is a 371 application of PCT/US2012/054802, filed on Sep. 12, 2012, which claims the benefit of U.S. Provisional Application No. 61/534,032, filed Sep. 13, 2011, the content of which is incorporated herein by reference in its entirety.

This application claims the benefit of U.S. Provisional Application No. 61/578,582, filed Dec. 21, 2011, the content of which is incorporated herein by reference in its entirety.

This application claims the benefit of U.S. Provisional Application No. 61/656,600, filed Jun. 7, 2012, the content of which is incorporated herein by reference in its entirety.

This application claims the benefit of U.S. Provisional Application No. 61/681,340, filed Aug. 9, 2012, the content of which is incorporated herein by reference in its entirety.

This application is related to PCT Application No. PCT/US2012/040414, filed Jun. 1, 2012, the content of which is incorporated herein by reference in its entirety.

This application is related to U.S. Provisional Application No. 61/492,578, filed Jun. 2, 2011, the content of which is incorporated herein by reference in its entirety.

This application is related to PCT Application No PCT/US2012/032279, filed Apr. 5, 2012, the content of which is incorporated herein by reference in its entirety.

This application is related to U.S. Provisional Application No. 61/472,344, filed Apr. 6, 2011, the content of which is incorporated herein by reference in its entirety.

This application is related to PCT Application No PCT/US2011/060214, filed Nov. 10, 2011, the content of which is incorporated herein by reference in its entirety.

This application is related to U.S. Provisional Application No. 61/412,733, filed Nov. 11, 2010, the content of which is incorporated herein by reference in its entirety.

This application is related to PCT Application No PCT/US2011/057282, filed Oct. 21, 2011, the content of which is incorporated herein by reference in its entirety.

This application is related to U.S. Provisional Application No. 61/406,032, filed Oct. 22, 2010, the content of which is incorporated herein by reference in its entirety.

This application is related to PCT Application No PCT/US2011/044811, filed Jul. 21, 2011, the content of which is incorporated herein by reference in its entirety.

This application is related to U.S. Provisional Application No. 61/368,257, filed Jul. 28, 2010, the content of which is incorporated herein by reference in its entirety.

This application is related to U.S. patent application Ser. No. 11/630,279, filed Dec. 20, 2006, published as U.S. Patent Application Publication No. 2009/0171151, the content of which is incorporated herein by reference in its entirety.

TECHNICAL FIELD

Embodiments of the present inventive concepts relate generally to the field of robotics and, more particularly, to three-dimensional, flexible, steerable robotic devices, and methods of forming and controlling the same.

BACKGROUND

As less invasive medical techniques and procedures become more widespread, medical professionals, such as surgeons, may employ snake-like robotic systems having highly articulated multi-link probes to access parts of the human anatomy that were otherwise difficult to reach. With the use of such robotic systems, medical professionals may be able to replace open-cavity surgical procedures with less invasive procedures.

Robotic systems of the type described above may have multiple device channels, referred to as working channels, for guiding a variety of surgical and/or interventional tools during surgical procedures. Conventional articulating probes, which generally comprise a series of steerable links, are subject to twisting, from link to link, which can adversely affect the performance of the articulating probe.

SUMMARY

Embodiments of the present inventive concepts may be directed to articulating robotic systems, robotic system user interfaces, human interface devices for controlling robotic systems and methods of controlling robotic systems.

In an aspect, an articulating probe, comprises: a first mechanism comprising: a first link comprising a first longitudinal axis, a first articulation surface and a first motion-limiting element; a second link comprising a second longitudinal axis, a second articulation surface and a second motion-limiting element; an articulation joint comprising the first articulation surface and the second articulation surface and constructed and arranged to allow two degree-of-freedom articulation of the second link relative to the first link; and a motion resisting assembly comprising the first motion limiting element and the second motion limiting element, wherein the motion resisting assembly is constructed and arranged to resist rotation of the second link about the second longitudinal axis relative to the first longitudinal axis of the first link.

In some embodiments, the first articulation surface comprises a convex surface and wherein the second articulation surface comprises a concave surface.

In some embodiments, the convex, first articulation surface comprises a semi-spherical surface.

In some embodiments, the concave, second articulation surface comprises a semi-spherical surface.

In some embodiments, the first motion-limiting element comprises a pin and wherein the second motion-limiting element comprises a slot and wherein the pin of the first link engages the slot of the second link.

In some embodiments, the convex, first articulation surface comprises a semi-spherical surface and wherein the pin is positioned to extend from an equatorial plane of the semi-spherical surface.

In some embodiments, the first motion-limiting element comprises first and second pins and wherein the second motion-limiting element comprises first and second corresponding slots and wherein over a range of articulation motion of the second link relative to the first link, at least one of the first and second pins is at least partially engaged with the corresponding at least one of the first and second slots.

In some embodiments, at an articulation angle of zero of the second link relative to the first link, both of the first and second pins are partially engaged with the first and second corresponding slots.

In some embodiments, the first and second pins are angularly spaced apart 180 degrees about the first longitudinal axis relative to the first articulation surface.

In some embodiments, the first and second slots are angularly spaced apart 180 degrees about the second longitudinal axis relative to the second articulation surface.

In some embodiments, the first motion-limiting element comprises a single pin and wherein the second motion-limiting element comprises a single slot and wherein over a range of articulation motion of the second link relative to the first link, the pin is at least partially engaged with the slot.

In some embodiments, the pin is positioned on the first articulation surface and wherein the slot is positioned on the second articulation surface.

In some embodiments, the slot is positioned on the first articulation surface and wherein the pin is positioned on the second articulation surface.

In some embodiments, the convex, first articulation surface comprises a semi-spherical surface and wherein the pin is positioned on the first articulation surface between an equator and a pole of the first articulation surface and wherein the slot is positioned on the second articulation surface.

In some embodiments, the convex, first articulation surface comprises a semi-spherical surface and wherein the slot is positioned on the semi-spherical first articulation surface between an equator and a pole of the first articulation surface and wherein the pin is positioned on the second articulation surface.

In some embodiments, the first motion-limiting element comprises a single slot and wherein the second motion-limiting element comprises a single pin and wherein over a range of articulation motion of the second link relative to the first link, the pin is at least partially engaged with the slot.

In some embodiments, the convex, first articulation surface comprises a semi-spherical surface and wherein the slot is positioned on the semi-spherical first articulation surface and extends from an equator of the first articulation surface in a direction toward a pole of the first articulation surface of the first link and wherein the pin is positioned below the second articulation surface of the second link.

In some embodiments, the pin is positioned on the second link at a position that aligns with an equator of the semi-spherical first articulation surface of the first link, when the second link is at an articulation angle of zero relative to the first link.

In some embodiments, the second link further comprises a third motion-limiting element comprising a single slot that is spaced apart 120 degrees in position relative to the pin, the third motion limiting element comprising a second motion limiting assembly that is constructed and arranged to resist rotation of a third link having a mating pin about a third longitudinal axis relative to the second link about the second longitudinal axis.

In some embodiments, the first motion-limiting element comprises at least one rib and wherein the second motion-limiting element comprises at least one recess and wherein over a range of articulation motion of the second link relative to the first link, the at least one rib is at least partially engaged with the at least one recess.

In some embodiments, the first motion-limiting element comprises a plurality of ribs and wherein the second motion-limiting element comprises a plurality of corresponding recesses and wherein over a range of articulation motion of the second link relative to the first link, at least one of the plurality of ribs is at least partially engaged with the corresponding at least one of the plurality of recesses.

In some embodiments, the convex, first articulation surface comprises a semi-spherical surface and wherein the plurality of ribs are spaced about an equator region of the semi-spherical first articulation surface at regular angular intervals about the first longitudinal axis.

In some embodiments, the plurality of ribs comprises two ribs that are spaced at 180 degrees about the first longitudinal axis of the first link.

In some embodiments, the plurality of recesses comprises two recesses that are spaced at 180 degrees about the second longitudinal axis.

In some embodiments, the plurality of ribs comprises three ribs that are spaced at 120 degrees about the first longitudinal axis of the first link.

In some embodiments, the plurality of recesses comprises three recesses that are spaced at 120 degrees about the second longitudinal axis.

In some embodiments, the plurality of ribs comprises four ribs that are spaced at 90 degrees about the first longitudinal axis of the first link.

In some embodiments, the plurality of recesses comprises four recesses that are spaced at 90 degrees about the second longitudinal axis.

In some embodiments, the plurality of ribs comprises five ribs that are spaced at 72 degrees about the first longitudinal axis of the first link.

In some embodiments, the plurality of recesses comprises five recesses that are spaced at 72 degrees about the second longitudinal axis.

In some embodiments, the plurality of ribs comprises six ribs that are spaced at 60 degrees about the first longitudinal axis of the first link.

In some embodiments, the plurality of recesses comprises six recesses that are spaced at 60 degrees about the second longitudinal axis.

In some embodiments, the plurality of ribs comprises seven ribs that are spaced at 360/7 degrees about the first longitudinal axis.

In some embodiments, the plurality of recesses comprises seven recesses that are spaced at 360/7 degrees about the second longitudinal axis.

In some embodiments, the plurality of ribs comprises eight ribs that are spaced at 45 degrees about the first longitudinal axis of the first link.

In some embodiments, the plurality of recesses comprises eight recesses that are spaced at 45 degrees about the second longitudinal axis.

In some embodiments, an outer surface of the first link at a portion between neighboring ones of the ribs is planar.

In some embodiments, an inner surface of the second link at a portion between neighboring ones of the recesses is planar.

In some embodiments, an inner surface of the second link at a portion between neighboring ones of the recesses is curved.

In some embodiments, the first articulation surface comprises a convex surface and wherein the second articulation surface comprises a concave surface.

In some embodiments, the convex, first articulation surface comprises a semi-ellipsoidal surface.

In some embodiments, the concave, second articulation surface comprises a semi-ellipsoidal surface.

In some embodiments: the semi-ellipsoidal, convex, first articulation surface of the first link comprises the first motion limiting element; and the semi-ellipsoidal, concave, second articulation surface of the second link comprises the second motion limiting element.

In some embodiments, an outermost surface of the first and second links is circular in cross section about the respective first and second longitudinal axes.

In some embodiments, the semi-ellipsoidal surface of the first articulation surface has a major axis and a minor axis and wherein the major axis is greater in length than the minor axis.

In some embodiments, the semi-ellipsoidal surface of the second articulation surface has a major axis and a minor axis and wherein the major axis is greater in length than the minor axis.

In some embodiments, the first articulation surface comprises convex and concave regions and wherein the second articulation surface comprises concave and convex regions that correspond to the convex and concave regions of the first articulation surface.

In some embodiments: the first articulation surface of the first link comprises the first motion limiting element; and the second articulation surface of the second link comprises the second motion limiting element.

In some embodiments, an outermost surface of the first and second links is circular in cross section about the respective first and second longitudinal axes.

In some embodiments, the first and second links comprise outer links of the articulating probe.

In some embodiments, the first and second links comprise inner links of the articulating probe.

In some embodiments, the first motion-limiting element comprises a first magnet and wherein the second motion-limiting element comprises a second magnet, and wherein the first and second magnets are positioned on the first and second links respectively so as to magnetically engage each other.

In some embodiments, the first and second links each comprises a base having a lower surface and an upper shoulder, wherein: the first magnet is positioned on the upper shoulder of the base; and the second magnet is positioned on the lower surface of the base, and wherein the first and second magnets are aligned relative to each other so as to magnetically engage each other.

In some embodiments, the first and second magnets have opposed polarity.

In some embodiments, the first magnet comprises multiple first magnets and wherein the second magnet comprises multiple second magnets and wherein the multiple first and second magnets are positioned about the longitudinal axes of the respective first and second links at regular angular intervals.

In some embodiments, the first articulation surface comprises a convex surface and wherein the second articulation surface comprises a concave surface.

In some embodiments, the convex, first articulation surface comprises a semi-spherical surface.

In some embodiments, the concave, second articulation surface comprises a semi-spherical surface.

In some embodiments: the first magnet is positioned on the first articulation surface; and the second magnet is positioned on the second articulation surface, wherein the first and second magnets are aligned relative to each other so as to magnetically engage each other.

In some embodiments, the first and second magnets have opposed polarity.

In some embodiments, a subset of the first magnets has a first polarity and a remaining subset of the first magnets has a second polarity opposite the first polarity.

In some embodiments, the first magnets all have a same, first polarity and the second magnets all have a same, second polarity.

In some embodiments, the first magnet comprises multiple first magnets and wherein the second magnet comprises multiple second magnets and wherein the multiple first and second magnets are positioned about the longitudinal axes of the respective first and second links at regular angular intervals.

In some embodiments, the multiple first and second magnets comprise discrete magnetic elements embedded in the respective first and second articulating surfaces.

In some embodiments, the multiple first and second magnets comprise magnetic strips embedded in the respective first and second articulating surfaces.

In some embodiments, the first articulation surface comprises a convex surface and wherein the second articulation surface comprises a concave surface.

In some embodiments, the first motion-limiting element comprises a pin and wherein the second motion-limiting element comprises a slot and wherein the pin of the first link engages the slot of the second link, and wherein the pin of the first link interfaces with sidewalls of the slot of the second link to resist the rotation of the first link relative to the second link.

In some embodiments, the first mechanism comprises an outer link mechanism of the articulating probe.

In some embodiments, the first mechanism comprises an inner link mechanism of the articulating probe.

In some embodiments, the motion limiting assembly limits rotation of the second link to about 1 degree of rotation about its longitudinal axis.

In some embodiments, the articulating probe further comprises at least one steering cable opening through the first link and the second link extending in a direction that is parallel to the respective first and second longitudinal axes.

In some embodiments, the articulating probe further comprises at least one steering cable corresponding to links in the first mechanism that is selectively tensioned to retain the first and second articulation surfaces of the first and second links in physical contact and selectively released to allow for selective motion of the second link relative to the first link.

In some embodiments, the at least one steering cable opening comprises multiple steering cable openings and wherein the at least one steering cable comprises multiple steering cables.

In some embodiments, the articulating probe comprises two steering cable openings and two steering cables.

In some embodiments, the articulating probe comprises three steering cable openings and three steering cables.

In some embodiments, the articulating probe comprises four steering cable openings and four steering cables.

In some embodiments, the first link further comprises a first articulation axis and a second articulation axis, the first and second articulation axes normal to each other and normal to the first longitudinal axis of the first link; the second link further comprises a first articulation axis and a second articulation axis, the first and second articulation axes normal to each other and normal to the second longitudinal axis of the second link; and two-degree-of-freedom articulation of the second link relative to the first link comprises angular movement of the second link about the first and second articulation axes of the first link.

In another aspect, an articulating probe, comprises: a plurality of outer links, each outer link comprising a first longitudinal axis and an inner surface, the inner surface of each outer link having at least one first concave region that extends in a direction along the first longitudinal axis; a plurality of inner links, each inner link comprising a second longitudinal axis and an outer surface, the outer surface of each inner link having at least one second concave region that extends in a direction along the second longitudinal axis; an anti-twist member positioned between the first concave regions and the second concave regions of the plurality of inner links and the plurality of outer links to allow two degree-of-freedom articulation of the inner links with respect to each other and to allow two degree-of-freedom articulation of the outer links with respect to each other and to limit rotation of an inner link relative to a neighboring inner link and limit rotation of an outer link relative to a neighboring outer link.

In some embodiments, the first concave regions of the outer links and the second concave regions of the inner links comprise working channels of the probe.

In some embodiments, the anti-twist member comprises a tube-shaped member.

In some embodiments, the anti-twist member is continuous from a proximal link to a distal link of the plurality of inner and outer links.

In some embodiments, the anti-twist member is segmented from a proximal link to a distal link of the plurality of inner and outer links.

In another aspect, a method of performing a surgical procedure comprises: selecting the articulating probe as described herein; and manipulating the articulating probe to position at least one tool using the probe.

In another aspect, a system for performing a surgical procedure includes an articulating probe as described herein.

In another aspect, a method of forming an articulating probe comprises: providing a first mechanism comprising: forming a first link comprising a first longitudinal axis, a first articulation surface and a first motion-limiting element; forming a second link comprising a second longitudinal axis, a second articulation surface and a second motion-limiting element; forming an articulation joint comprising the first articulation surface and the second articulation surface and constructed and arranged to allow two degree-of-freedom articulation of the second link relative to the first link; and forming a motion resisting assembly comprising the first motion limiting element and the second motion limiting element, wherein the motion resisting assembly is constructed and arranged to resist rotation of the second link about the second longitudinal axis relative to the first longitudinal axis of the first link.

BRIEF DESCRIPTION OF THE DRAWINGS

The foregoing and other objects, features and advantages of embodiments of the present inventive concepts will be apparent from the more particular description of embodiments, as illustrated in the accompanying drawings in which like reference characters refer to the same elements throughout the different views. The drawings are not necessarily to scale, emphasis instead being placed upon illustrating the principles of the embodiments.

FIG. 5C is a lower perspective view of the link of FIG. 5B.

FIG. 6C is a lower perspective view of the link of FIG. 6B.

FIGS. 8A(1), 8A(2), 8B(1), 8B(2), 8C(1), and 8C(2) are top views of first and second outer links of an articulating probe of a system for performing a medical procedure according to other embodiments of the present inventive concepts.

FIG. 9 is a cross-sectional view of an inner link and an outer link including an anti-twist member positioned therebetween, in accordance with embodiments of the present inventive concepts.

DETAILED DESCRIPTION OF EMBODIMENTS

Figure 1A:
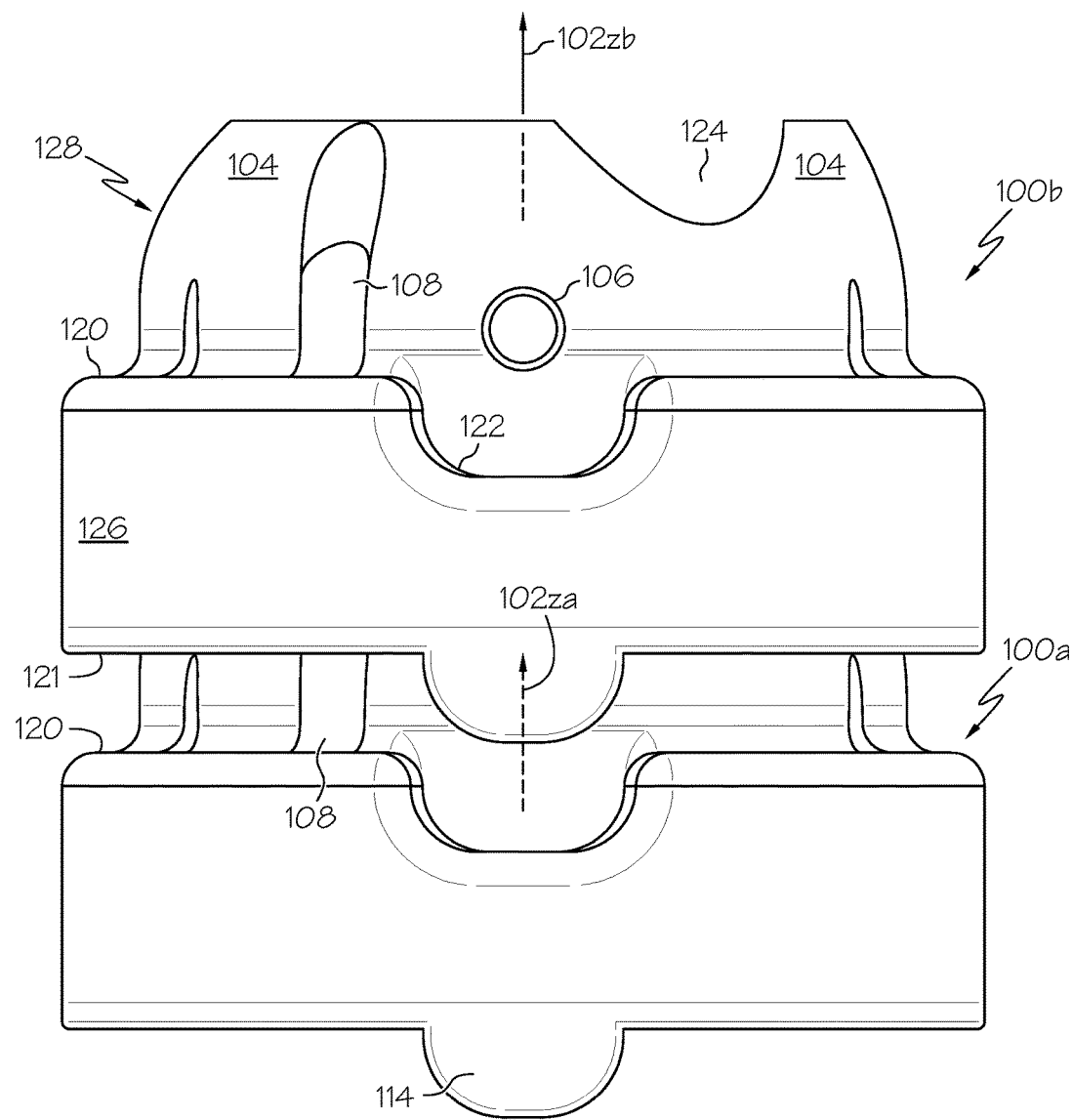
FIG. 1A is a side view of first and second outer links of an articulating probe of a system for performing a medical procedure according to embodiments of the present inventive concepts.

The terminology used herein is for the purpose of describing particular embodiments and is not intended to be limiting of the inventive concepts. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on" or "connected" or "coupled" to another element, it can be directly on or above, or connected or coupled to, the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.). When an element is referred to herein as being "over" another element, it can be over or under the other element, and either directly coupled to the other element, or intervening elements may be present, or the elements may be spaced apart by a void or gap. There are numerous types of steerable multi-linked, highly articulated probes. Robert Sturges' U.S. Pat. No. 5,759,151, which is hereby incorporated by reference in its entirety, discloses a flexible, steerable device for conducting exploratory procedures. The device includes at least one spine, each having stiffening means for selectively rendering the spine rigid and flexible along its length. A flexible sheath surrounds the spine and is axially slidably moveable relative to the spine so that the sheath will follow and conform to the shape of a spine in the rigid state and resist further flexure when the spine is in a relaxed state. A steerable distal tip is provided on the distal end of the device. Controls for the distal tip are mounted on the proximal end of the device. Mechanisms are provided on the distal end of the device for selectively activating and deactivating the stiffening means of the spine. An instrument conduit may be mounted on the sheath. Howard Choset's U.S. patent application Ser. No. 11/630,279, which is hereby incorporated by reference in its entirety, discloses a feeder mechanism for advancing and retracting both an inner core and an outer sleeve, as well as selectively applying tension to control cables used for steering and causing either the inner core or outer sleeve to transition between a rigid state and a limp state.

U.S. Pat. No. 6,610,007 discloses a steerable endoscope having an elongated body with a selectively steerable distal portion and an automatically controlled proximal portion. The endoscope body is inserted into a patient and the selectively steerable distal portion is used to select a desired path within the patient's body. When the endoscope body is advanced, an electronic motion controller operates the automatically controlled proximal portion to assume the selected curve of the selectively steerable distal portion. Another desired path is selected with the selectively steerable distal portion and the endoscope body is advanced again. As the endoscope body is further advanced, the selected curves propagate proximally along the endoscope body, and when the endoscope body is withdrawn proximally, the selected curves propagate distally along the endoscope body. This creates a serpentine motion in the endoscope body allowing it to negotiate tortuous curves along a desired path through or around and between organs within the body.

Figure 10A:
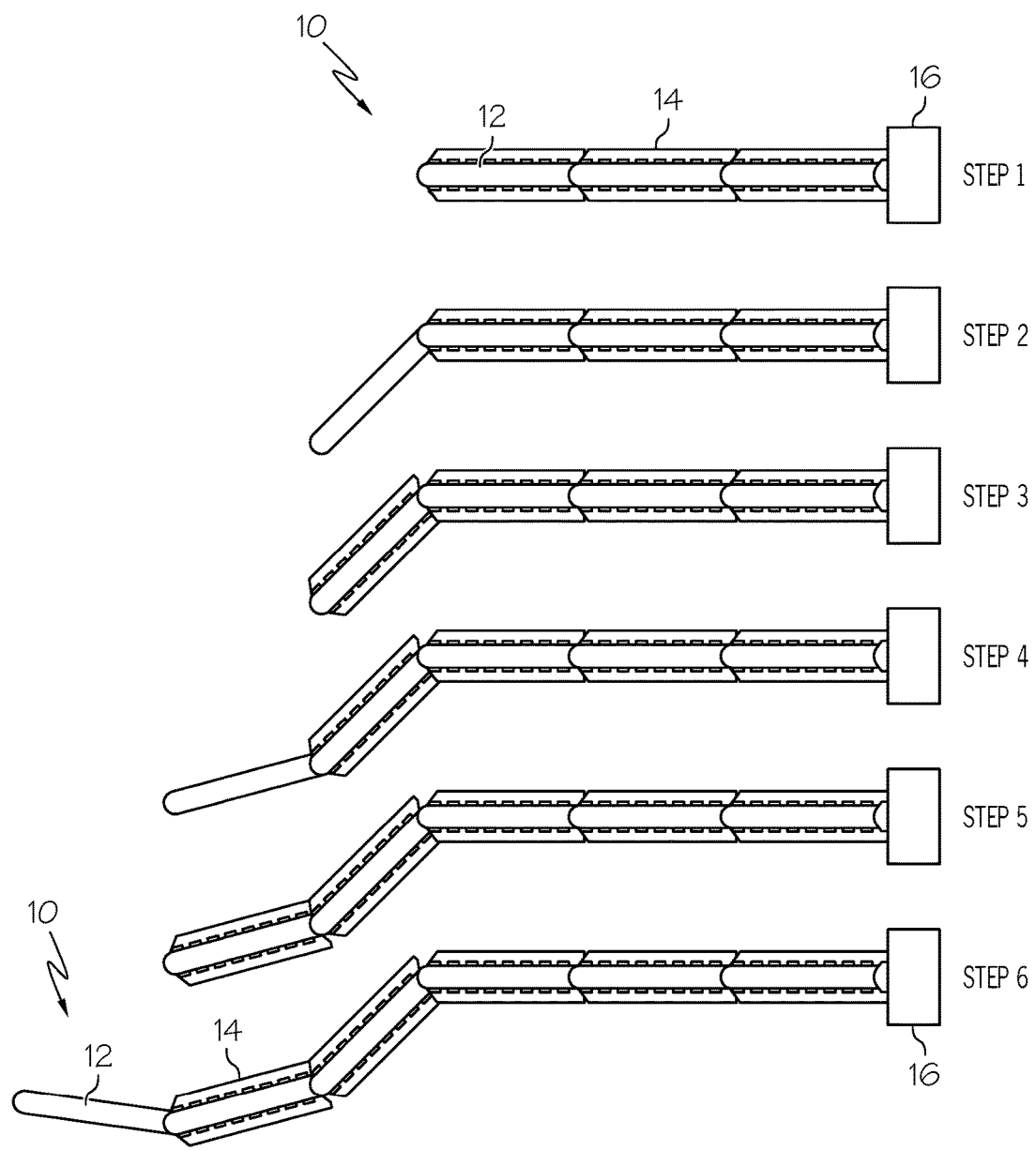
FIGS. 10A-10C are graphic demonstrations of a highly articulated probe device, according to embodiments of the present inventive concepts.
Figure 10B:
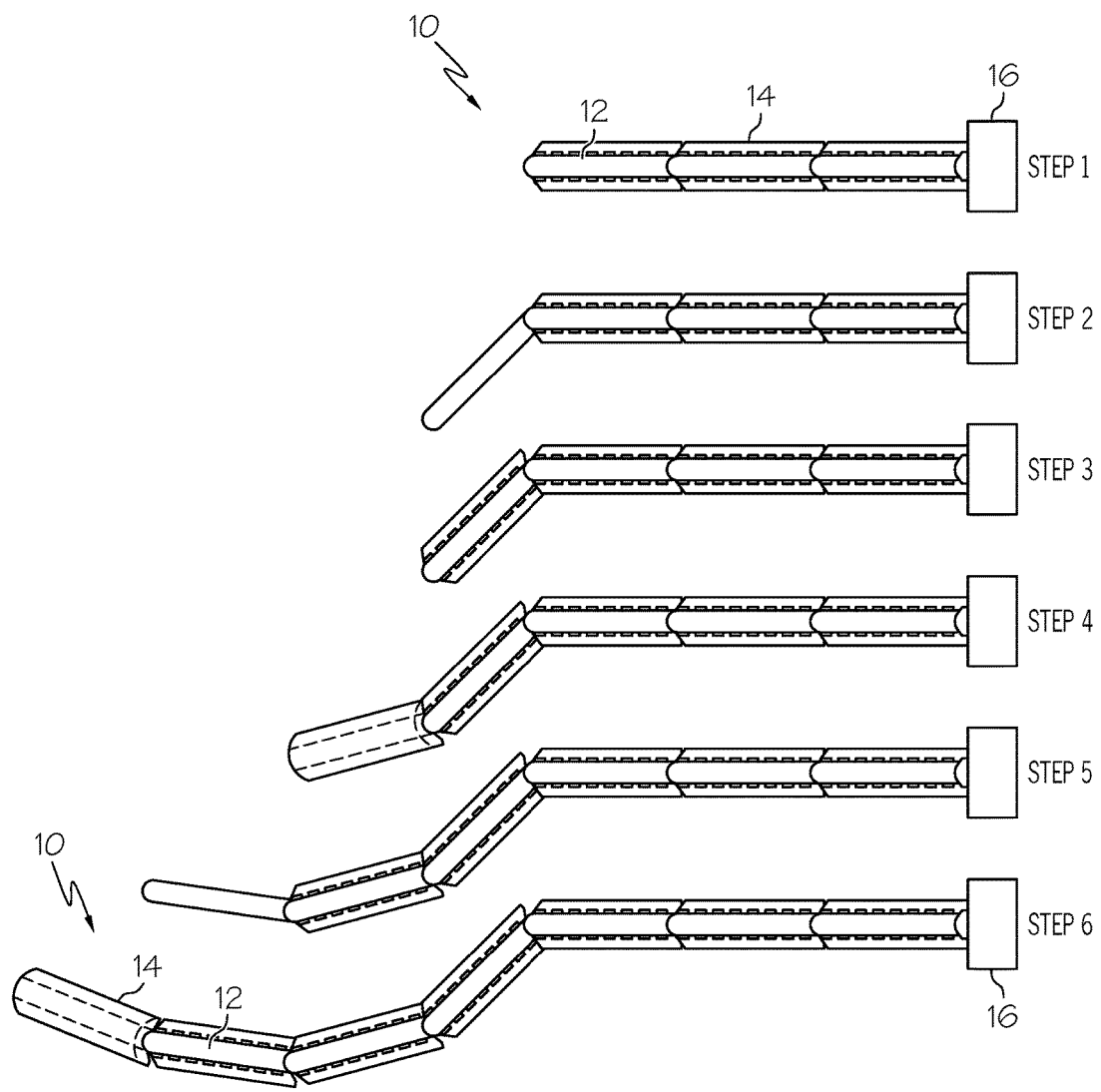
Figure 10C:
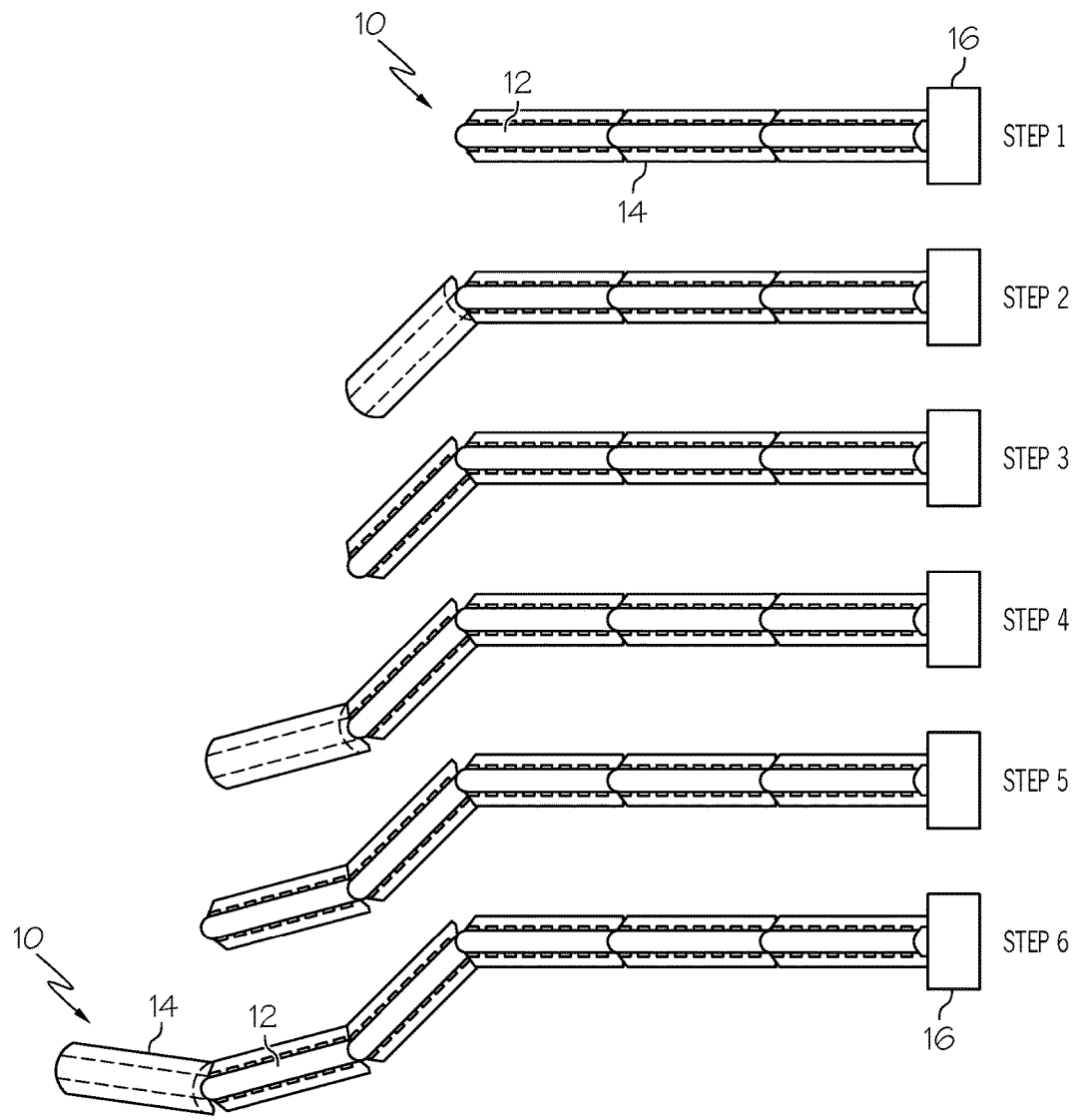

FIGS. 10A-10C are graphic demonstrations of a highly articulated probe device, according to embodiments of the present inventive concepts. A highly articulated robotic probe 10, according to the embodiment shown in FIGS. 10A-10C, comprises essentially two concentric mechanisms, an outer mechanism and an inner mechanism, each of which can be viewed as a steerable mechanism. FIGS. 10A-10C show the concept of how different embodiments of the probe 10 operate. Referring to FIG. 10A, the inner mechanism can be referred to as a first mechanism, an inner core or inner core mechanism 12. The outer mechanism can be referred to as a second mechanism, an outer sleeve or outer sleeve mechanism 14. Each mechanism can alternate between being rigid and limp. In the rigid mode or state, the mechanism is relatively inflexible such that it cannot be readily re-shaped. In the limp mode or state, the mechanism is highly flexible and thus either assumes the shape of its surroundings or can be re-shaped. It should be noted that the term "limp" as used herein does not denote a structure that passively assumes a particular configuration dependent upon gravity and the shape of its environment; rather, the "limp" structures described in this application are capable of assuming positions and configurations that are desired by the operator of the device, and therefore are articulated and controlled rather than flaccid and passive.

In some embodiments, one mechanism starts limp and the other starts rigid. For the sake of explanation, assume the outer sleeve 14 is rigid and the inner core 12 is limp, as seen in step 1 in FIG. 10A. Now, the inner core 12 is both pushed forward by a feeding mechanism 16, described below, and its "head" or distal end is steered, as seen in step 2 in FIG. 10A. Now, the inner core 12 is made rigid and the outer sleeve 14 is made limp. The outer sleeve 14 is then pushed forward until it catches up or is coextensive with the inner core 12, as seen in step 3 in FIG. 10A. Now, the outer sleeve 14 is made rigid, the inner core 12 limp, and the procedure then repeats. One variation of this approach is to have the outer sleeve 14 be steerable as well. The operation of such a device is illustrated in FIG. 10B. In FIG. 10B it is seen that each mechanism is capable of catching up to the other and then advancing one link beyond. According to one embodiment, the outer sleeve 14 is steerable and the inner core 12 is not. The operation of such a device is shown in FIG. 10C.

In medical applications, once the probe 10 arrives at a desired location, the operator, typically a surgeon, can slide one or more tools through one or more channels of outer sleeve 14, inner core 12, or a channel formed between outer sleeve 14 and inner core 12, such as to perform various diagnostic and/or therapeutic procedures. In some embodiments, the channel is referred to as a working channel, that can, for example extend between first recesses formed in a system of outer links and second recesses formed in a system of inner links. In some embodiments, the inner and outer links are of a type depicted in FIGS. 1-9 described in detail herein.

In addition to clinical procedures such as surgery, probe 10 can be used in numerous applications including but not limited to: engine inspection, repair or retrofitting; tank inspection and repair; spying and surveillance applications; bomb disarming; inspection or repair in tightly confined spaces such as submarine compartments or nuclear weapons; structural inspections such as building inspections; hazardous waste remediation; biological sample recovery such as anthrax recovery; and combination of these. Clearly, the device of the present disclosure has a wide variety of applications and should not be taken as being limited to any particular application.

Figure 11A:
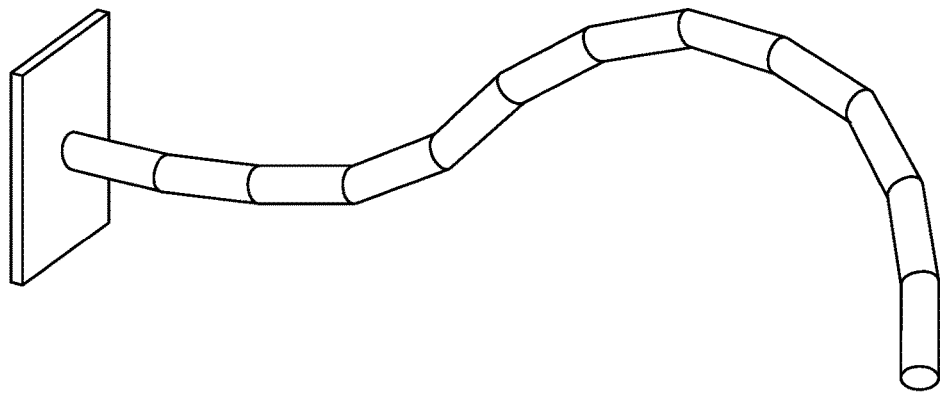
FIGS. 11A-11B illustrate various configurations assumed by a highly articulated probe, according to embodiments of the present inventive concepts.
Figure 11B:
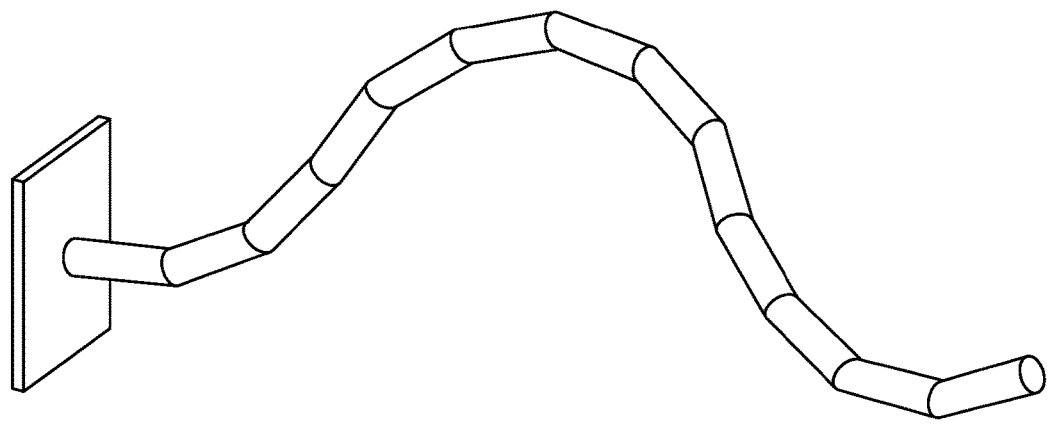
Figure 12A:
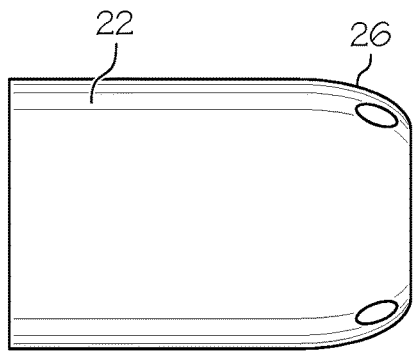
FIGS. 12A-12D illustrate various views of a link of an outer sleeve, according to embodiments of the present inventive concepts.
Figure 12B:
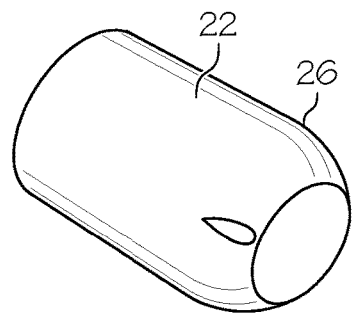
Figure 12C:
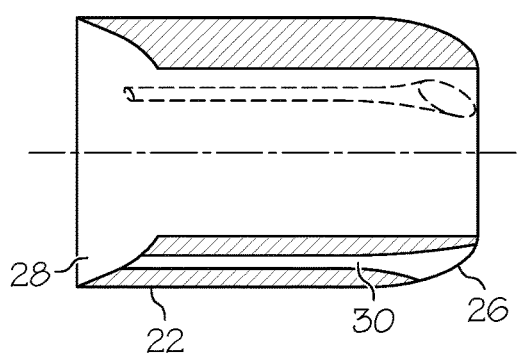
Figure 12D:
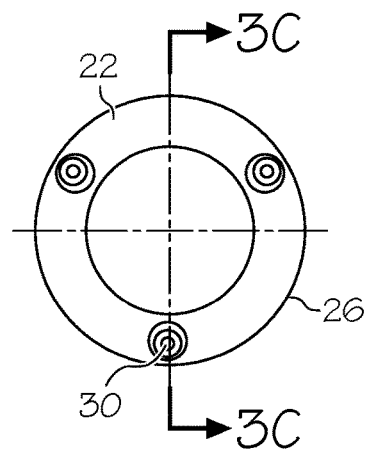
Figure 13A:
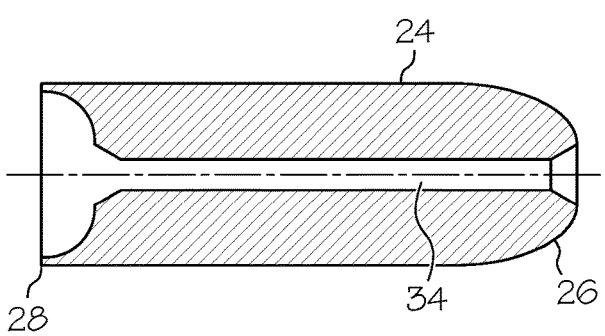
FIGS. 13A and 13B illustrate end and cross-sectional views, respectively, of a link of an inner core, according to embodiments of the present inventive concepts.
Figure 13B:
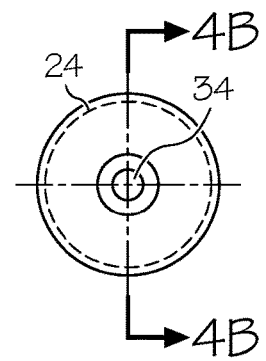

Inner core 12 and/or outer sleeve 14 are steerable and inner core 12 and outer sleeve 14 can each be made both rigid and limp, allowing probe 10 to drive anywhere in three-dimensions. Probe 10 can "remember" its previous configurations and for this reason, probe 10 can go anywhere in a three dimensional volume such as the intracavity spaces in the body of a patient such as a human patient. FIGS. 11A-11B illustrate examples of various configurations assumable by probe 10.

As can be seen in FIGS. 12A-12D and 13A and 13B, according to one embodiment, the outer sleeve 14 and inner core 12, respectively, can be made up of concentric cylinders, outer links 22 and inner links 24, respectively, although links of other shapes may be used, e.g. a dog bone configuration (not shown) as well as links of a type that are not concentric, e.g. backbone configuration, among others. In some embodiments, the ends of the links 22, 24 are not flat but instead one end 26 is an "outer" or convex outer mating surface and the other end 28 is an "inner" or concave inner mating surface. In some embodiments, the inner and outer surfaces can comprise semi-spherical surfaces with similar radii of curvature; however, as described herein, embodiments of the present inventive concepts are not limited thereto. The links 22 are "chained", or nested back-to-back such that the concave end 28 of one mates with the convex end 26 of an adjacent link. Similarly, the links 24 are chained, or nested back-to-back. The result is a spherical-like joint, from a kinematic point of view. In the current embodiment, each link is able to rotate, or articulate on the adjacent link's head, acting as a spherical joint with approximately 10 to 20 degrees range of motion in any direction, although other ranges of motion are possible and potentially advantageous. According to one embodiment, the links 22 have a plurality of channels 30, or cable openings, extending therethrough to accommodate, in some embodiments, a plurality of control cables. Alternatively, in some embodiments, the cable openings 30 can be configured to accommodate elongate devices such as elongate tools.

In some embodiments, the heads (i.e. the distal links) of both the outer sleeve 14 and the inner core 12 are steerable using three cables which are positioned at, for example, 120° from each other. As can be seen in FIGS. 12A-12D, there are three small cylindrical channels 30 respectively, for cables to pass through. In the embodiment depicted in FIGS. 13A and 13B, the inner link 24 has only one cable, in which case there is only a single hole 34 through its center.

It will be appreciated that although the embodiment described above utilizes cables such as conductive or non-conductive wires or other flexible filamentous structure, alternative means of manipulating the limp elements, such as miniature pneumatic or hydraulic pistons or other mechanical linkages situated between individual links, can be employed without falling outside the scope of the present inventive concepts.

The links, and hence probe 10, can comprise virtually any material, including plastic or other magnetic resonance imaging compatible material. The outer sleeve 14 may assume a broad range of diameters, typically greater than 5 mm. Similarly, inner core 12 may assume a broad range of diameters, less than the diameter of outer sleeve 14 and typically more than 3 mm. The total number of outer links in an outer link assembly, or inner links in an inner link assembly links can vary over a large range but is typically greater than 10 outer or inner links.

As noted, the inner core 12 and outer sleeve 14 can be made rigid or limp using cables or other flexible filament structures. In some embodiments, outer sleeve 14 comprises a set of links 22 strung on three cables. The three cables can be positioned 120 degrees apart, making it possible to steer the sleeve in any direction. Radius of curvature of probe 10 is dependent on a number of factors including length of links 22 as well as mating dimensions between the ends of mating links 22. When the cables are pulled towards the back of the outer sleeve 14, the links 22 are pulled towards each other. When the pulling force increases, the friction force between adjacent links 22 increases until the whole outer sleeve 14 stiffens (i.e. enters the rigid mode). When the pulling force is released, the outer sleeve 14 becomes limp. Thus, the cables together with their respective tensioning assemblies (e.g. motor driven pulleys) form a locking device. The tensioning assemblies, along with the electronics for controlling the tensioning assemblies, form a means for controlling the tension on the cable. When the outer sleeve 14 is positioned one link position in front of the inner core 12, and the inner core 12 is rigid, the distal link of the outer sleeve 14 can be oriented by pulling one or more of the three cables. In addition to advancing or retracting cable, the magnitude of the pulling force which is exerted on each cable can be monitored or controlled. By pulling the three cables with the same magnitude, the outer sleeve 14 becomes rigid without changing its shape.

The inner core 12, like the outer sleeve 14, consists of a set of links. According to one embodiment, in contrast to the outer sleeve 14, the inner core 12 does not require a steering ability. In some embodiments, a steering feature is optional, and can be employed, in connection with the inner core 12. In some embodiments, the inner core 12 can change between a rigid mode and a limp mode. Therefore, in embodiments where the inner core 12 need not be steerable, the links of the inner core 12 may be strung on a single cable, which enables a reduced diameter for probe 10.

Figure 14A:
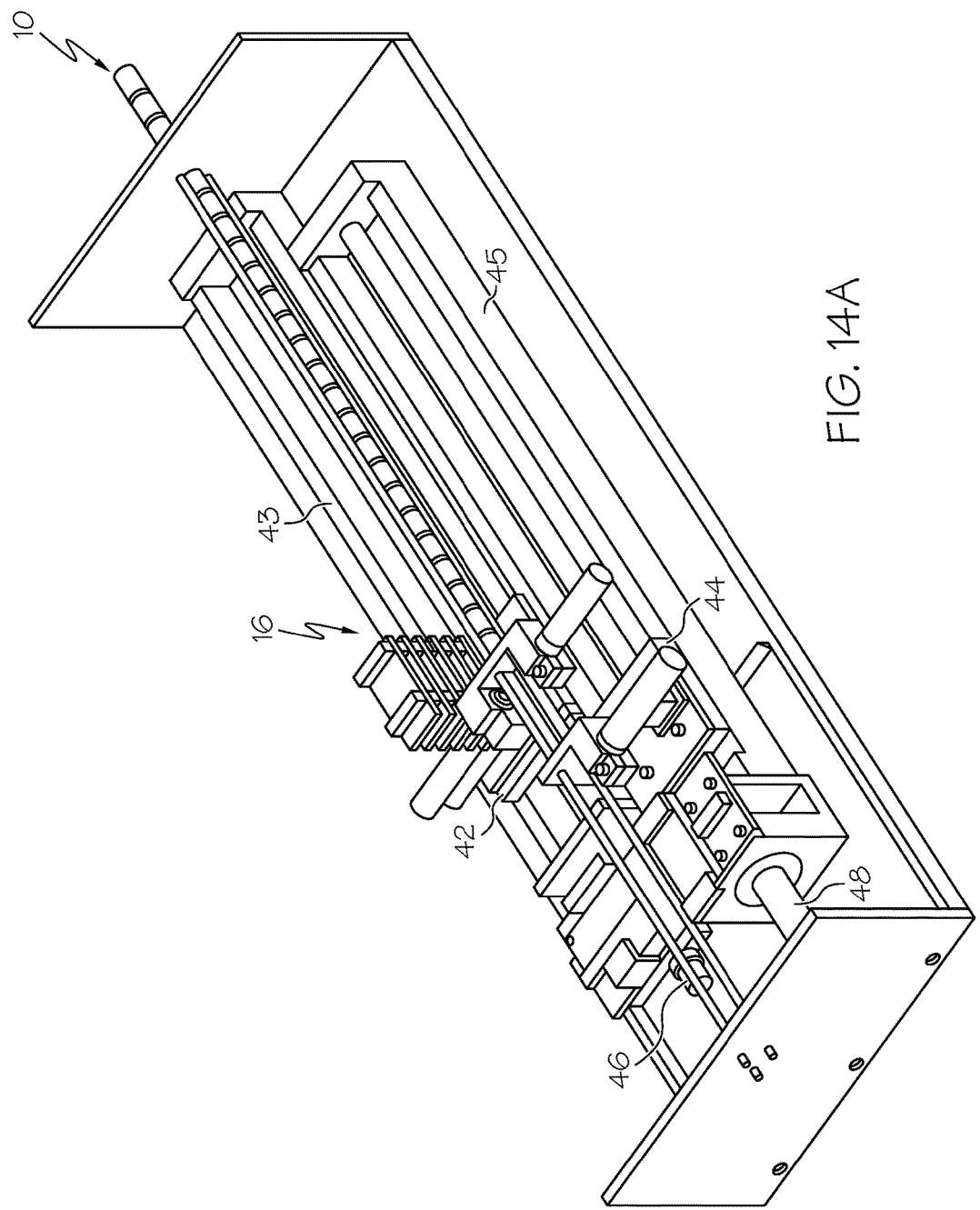
FIGS. 14A and 14B illustrates one example of a feeder mechanism, according to embodiments of the present inventive concepts.
Figure 14B:
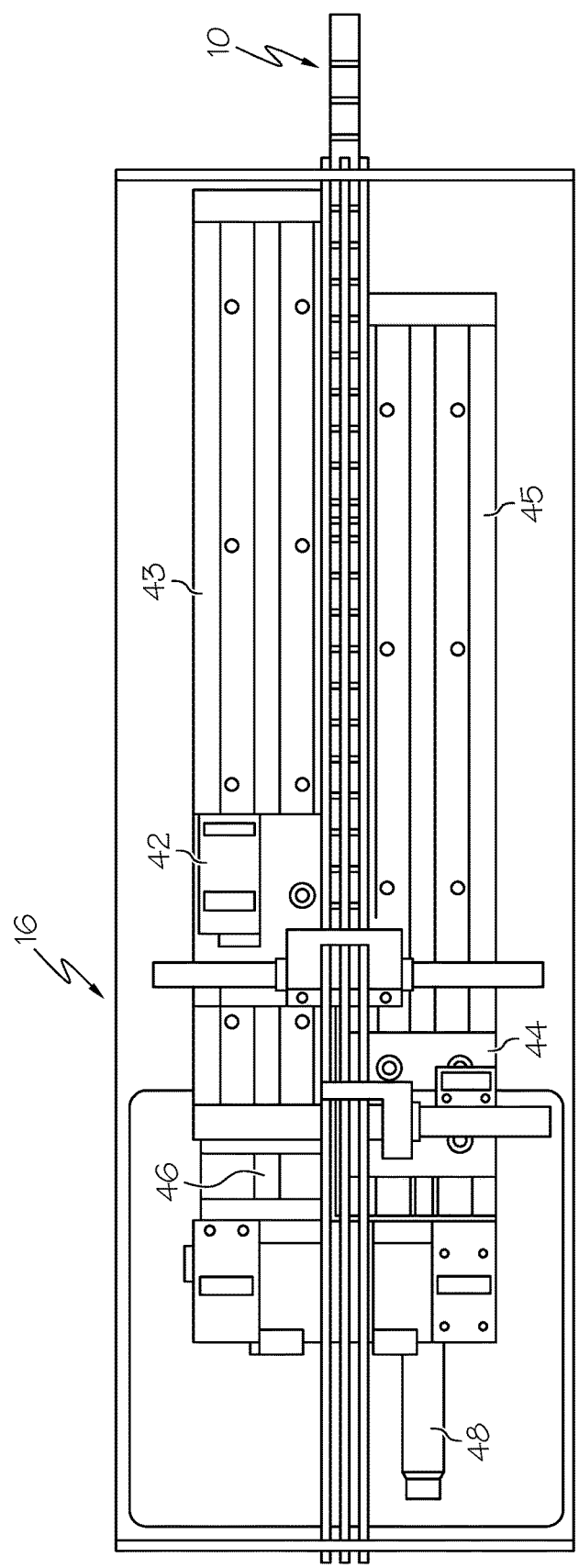

As mentioned above, a feeding mechanism 16 can be used to control the probe 10. One type of feeding mechanism 16, shown in FIGS. 14A and 14B, inserts and retracts the probe 10 into and out of, respectively, a region of interest such as the esophagus, the peritoneal space, the pericardial cavity, or another internal space of a patient. The feeder 16 has two movable carts. A first cart 42, carried in a first fixed tray 43, advances and retracts the outer sleeve 14 while a second cart 44 carried in a second fixed tray 45 advances and retracts the inner core 12. Each cart 42, 44, and hence, each of the inner core 12 and outer sleeve 14, is driven independently by separate linear actuators 46, 48 respectively. The linear actuators 46, 48 may carry shaft encoders (not shown) used for position control as is known to those of skill in the art. Alternatively or additionally, motor current may be monitored to determine a value for tension in a cable used to control position. Cable tension may be monitored with one or more sensors such as a load cell. Numerous positioning and other sensors may be included to provide information relative to cable tension; cart position; probe orientation and configuration; and other system parameters. Typical sensors include but are not limited to: optical sensors; magnetic sensors such as Hall effect sensors; force and pressure sensors such as accelerometers, strain gauges and mechanical switches; and combinations of these. One or more sensors may be positioned in multiple locations including but not limited to: feeding mechanism 16, inner core 12 and outer sleeve 14.

Figure 15:
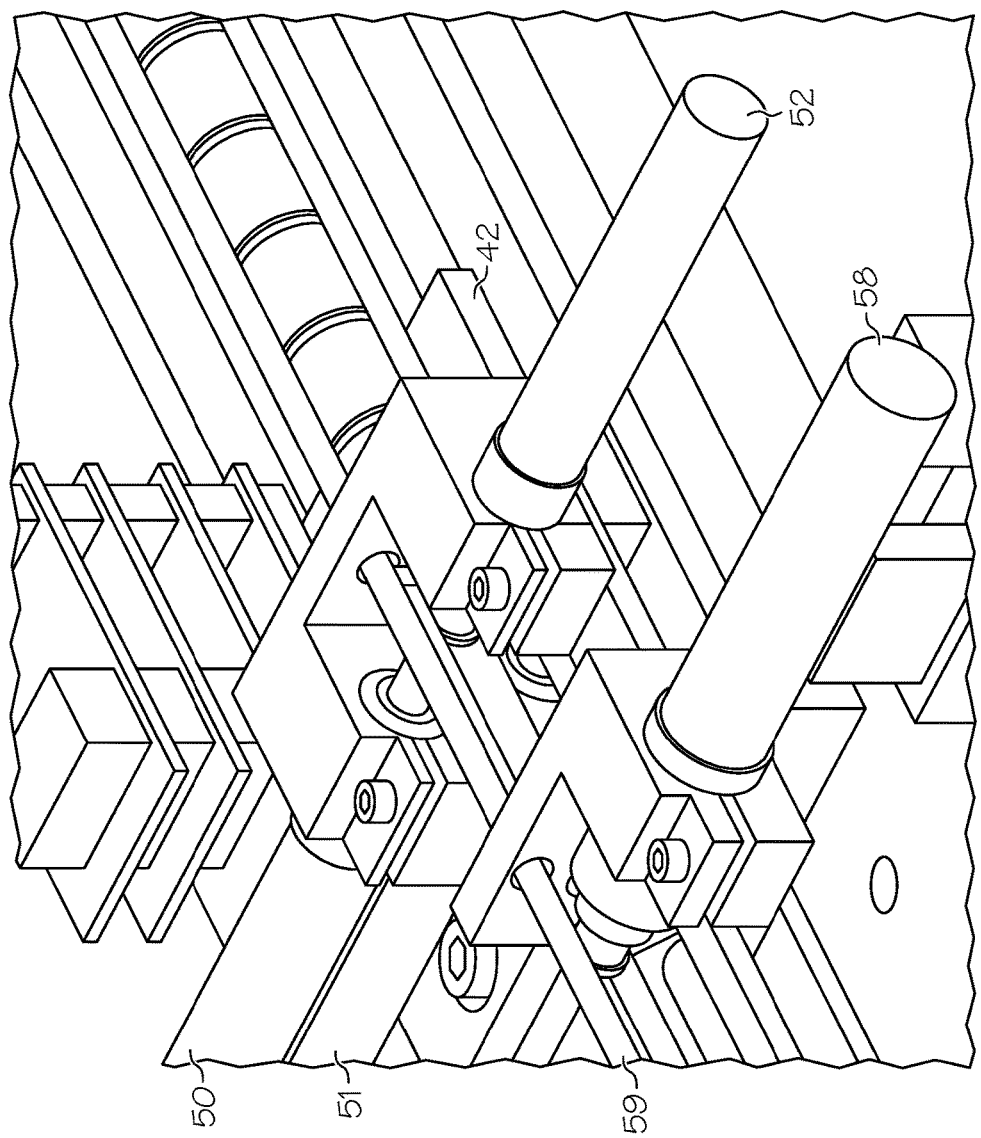
FIG. 15 illustrates devices for controlling the tension on cables, according to embodiments of the present inventive concepts.
Figure 16:
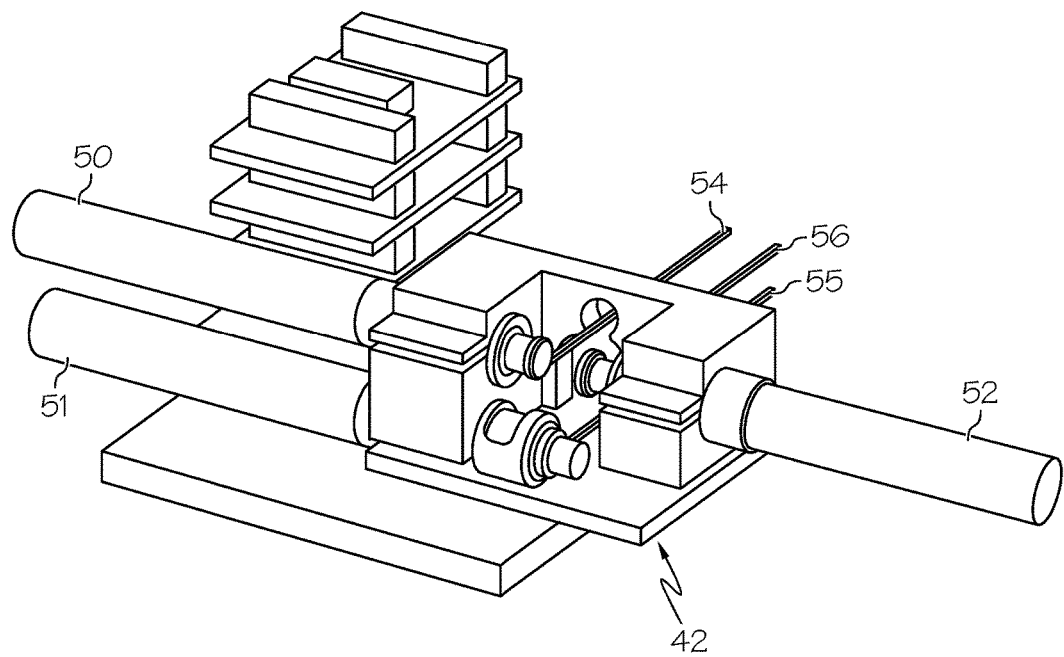
FIG. 16 illustrates devices for controlling the tension on the cables of the outer sleeve, according to embodiments of the present inventive concepts.
Figure 17:
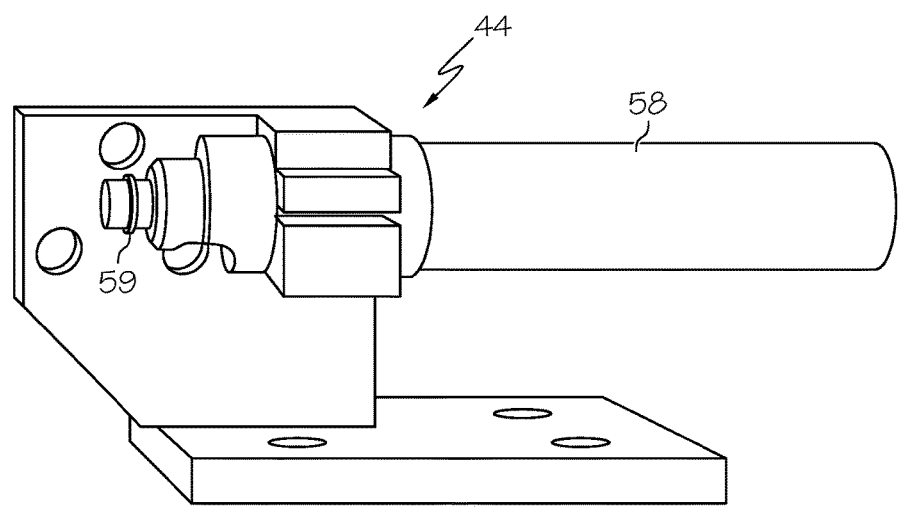
FIG. 17 illustrates a device for controlling the tension on the cable of the inner sleeve, according to embodiments of the present inventive concepts.

Each of the carts 42, 44 carries one or more motors necessary for controlling the cables of the inner core 12 and outer sleeve 14. For example, as seen in FIG. 15 and FIG. 16, the cart 42 carries motors 50, 51, 52 which control the tension on cables 54, 55, 56 of outer sleeve 14. As shown in FIG. 17, second cart 44 has a motor 58 for controlling the tension on cable 59 of the inner core 12. Each of the motors 50, 51, 52 and 58 may be provided with shaft encoders (not shown) used for position control as is known. In an embodiment where the inner core 12 is steerable, the inner core 12 requires two or more motors (e.g. to tension two or more cables) or another cable tensioning mechanism.

Figure 18:
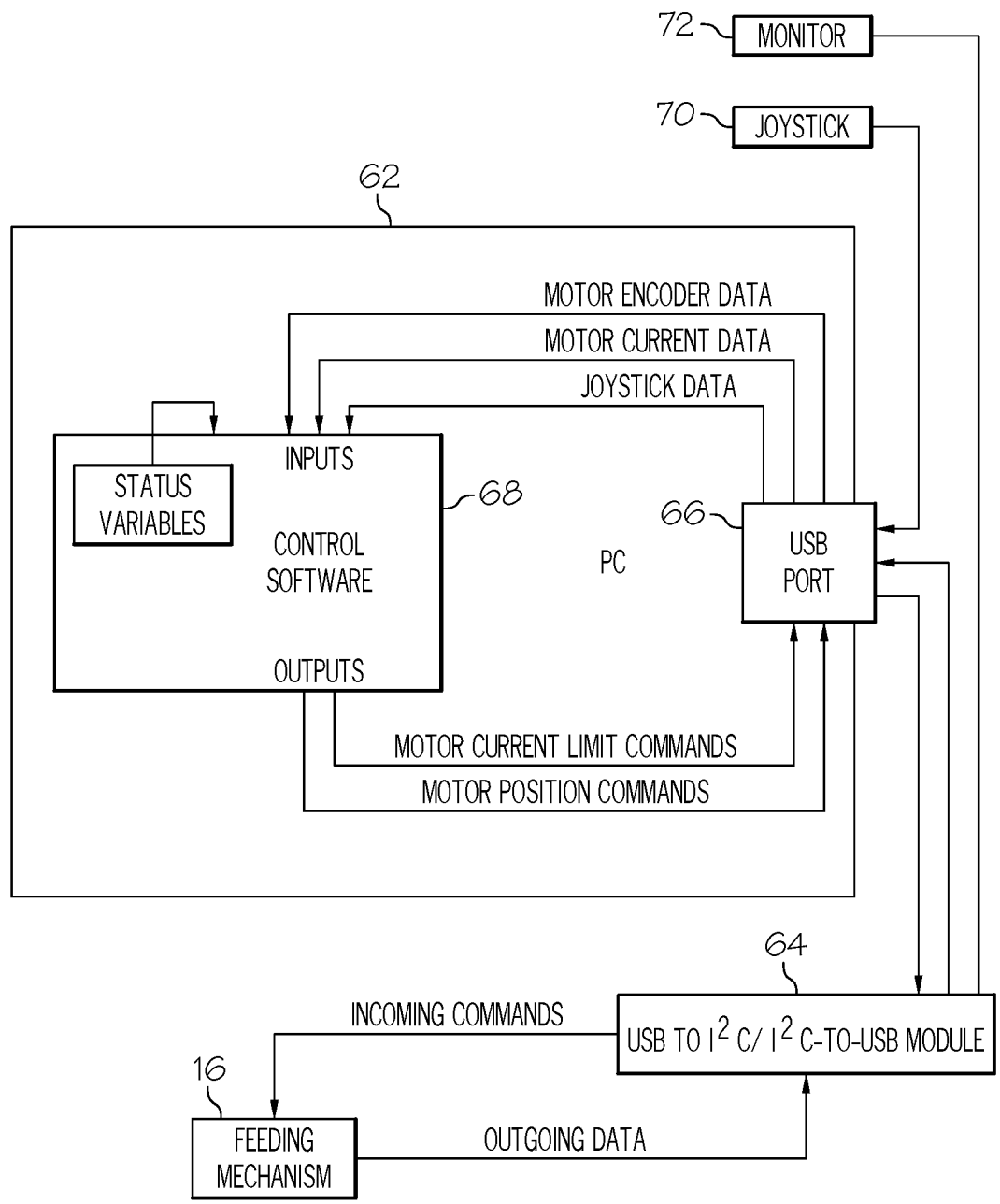
FIG. 18 is a block diagram illustrating the components of a control system and the flow of information between those components, according to embodiments of the present inventive concepts.

FIG. 18 is a block diagram illustrating the components of one embodiment of a control system and the flow of information between those components. The feeding mechanism 16 interfaces with a control computer 62 through a bus conversion module 64. Outgoing data from the feeding mechanism 16 is input to the module 64 for conversion to a communication protocol, such as USB protocol, and is then input to a USB port 66 on the computer 62. Incoming data to control software 68 may include motor current data, motor encoder data and/or cable tension data associated with each of the cables in the feeding mechanism 16. Alternatively or additionally, incoming data to control software 68 may include data from one or more sensors located in feeding mechanism 16, an inner core or an outer sleeve such as inner core 12 or outer sleeve 14 described herein. Joystick data (position data) may also be received from a joystick 70. A monitor 72 may be responsive to video data from a camera mounted on the distal end of the outer sleeve 14 and/or inner core 12 to provide visual feedback to a user regarding the position of the distal end of the probe 10. The control software 68 may output motor current limit commands and motor position commands which are input to the feeding mechanism 16.

During operation of articulating probes, the outer sleeve link systems and inner core link systems are subject to twisting, from link to link. For example, during operation of the probe, an inherent amount of twisting can occur between neighboring links. Twisting of links can be cumulative over the system of links. Accordingly, while the angle of misalignment can be minor from individual neighboring link to link, the total amount of twisting of the distal link of the system relative to the proximal link can be large. As the number of links in a system increases, so too can the amount of cumulative twist. Such twisting can adversely affect the performance of the articulating probe.

Twisting can occur due to a number of factors, including a difference between the outer radii of the steering cables and the inner radii of the steering cable openings. Also, the neighboring links may become misaligned prior to, or during, a procedure. The twisting of links relative to each other can cause an inconsistent relation of steering input to steering output. Loss of alignment between user and robot coordinate systems can occur. As a result, for an operator to initiate a turn in a particular direction, the robot must be moved in a different direction to compensate for twist. In addition, links that are twisted relative to each other may be subject to a limited range of steering. Twisting can also cause neighboring links to become inadvertently locked together, and the steering cables can become pinched in the gaps between over-twisted links. This can, in turn, lead to binding of the cables, resulting in higher steering forces, or incomplete release of tension when in a limp mode of operation. Further problems due to twisting can include the binding of instruments inserted through internal channels of the link systems, possible occlusion of internal tool channels, as well as increased wear on electrical conduits present in the system. Twisting can also result in increased wear and friction between inner and outer links, causing neighboring links to bind, or preventing their ability to advance during a procedure. Also, twisting can result in the misalignment between the end of the probe and the target anatomy.

Twisting between neighboring links can be as severe as 5 degrees of offset. Cumulative twisting of a distal link relative to a proximal link in a link system can be as large as 45 degrees. Embodiments described herein are directed to systems and methods for resisting or preventing the amount of twist of a second neighboring link relative to a first link, while still allowing for articulation of the links for steering purposes.

Figure 1B:
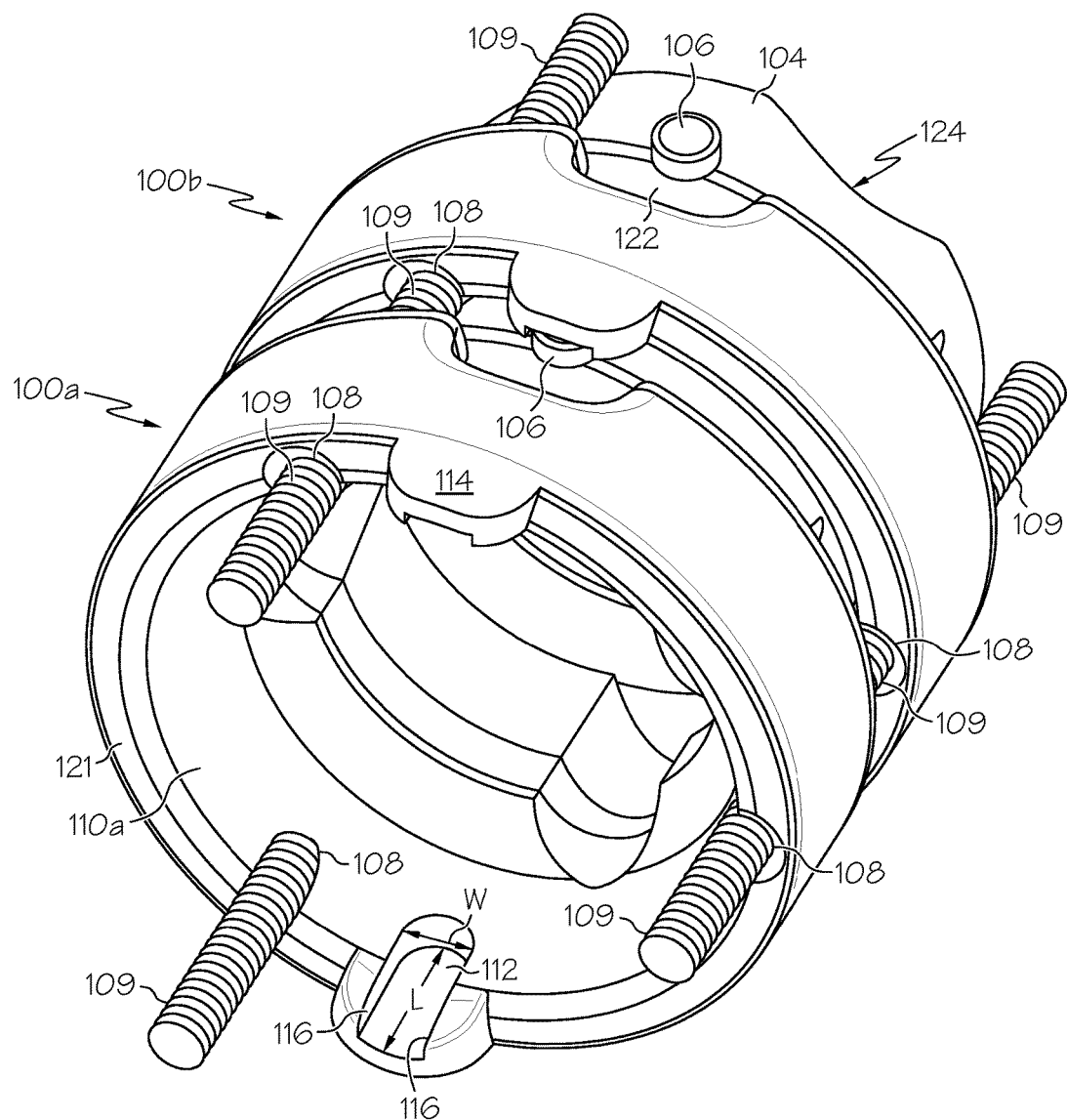
FIG. 1B is a lower perspective view of the first and second outer links of FIG. 1A.
Figure 1C:
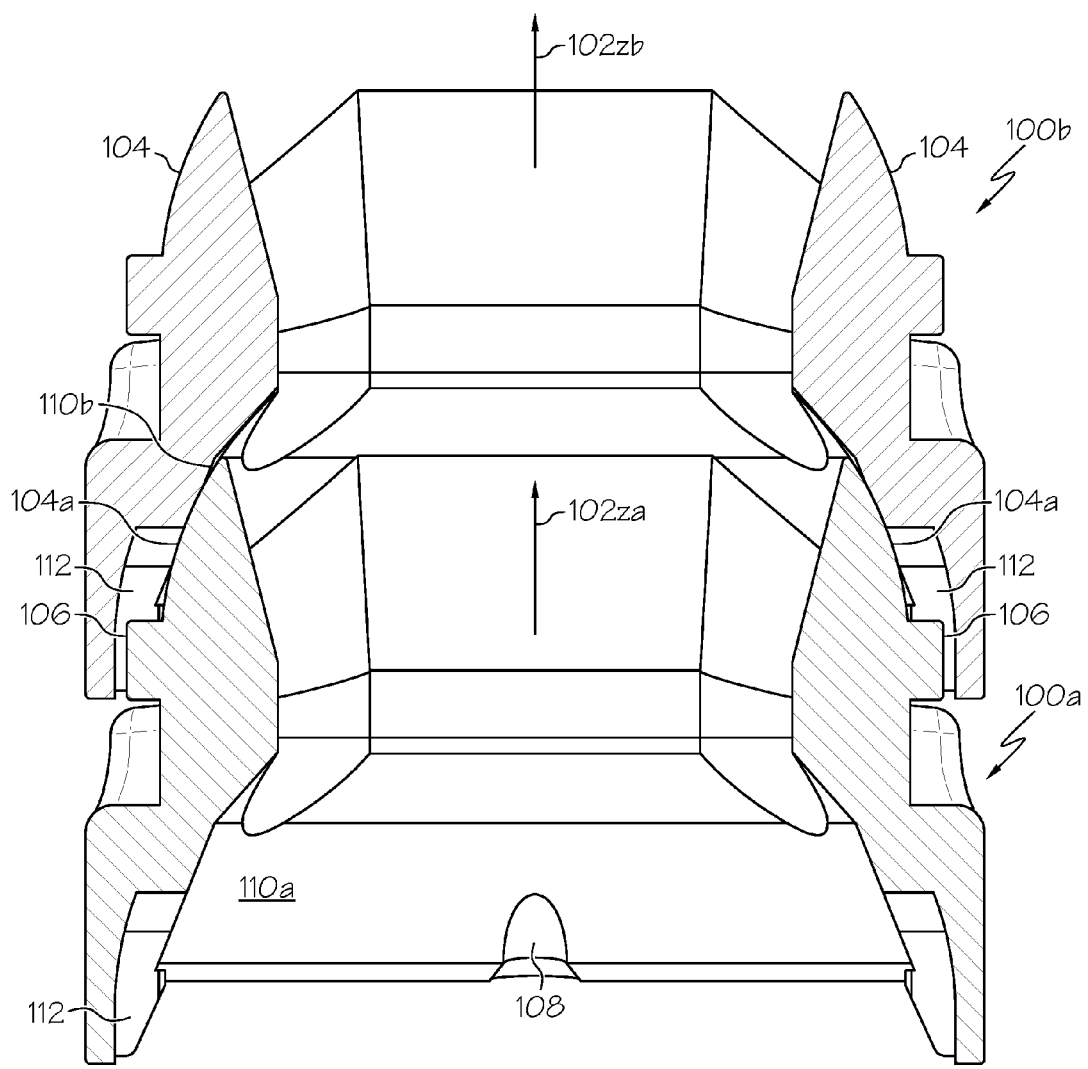
FIG. 1C is a cutaway side view of the first and second outer links of FIG. 1A.
Figure 1D:
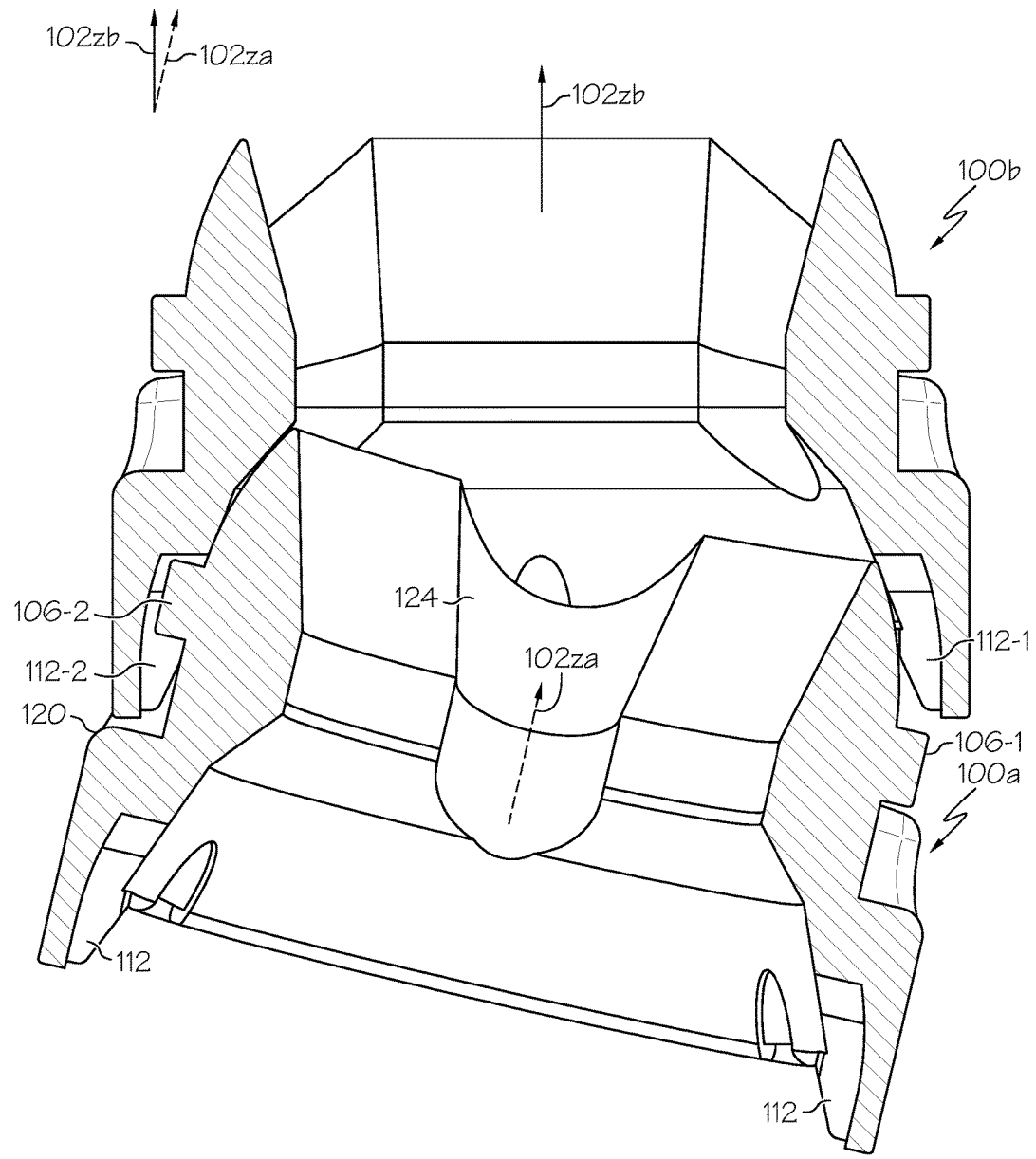
FIG. 1D is a cutaway side view of the first and second outer links of FIG. 1A illustrated with the second link articulated relative to the first link
Figure 1E:
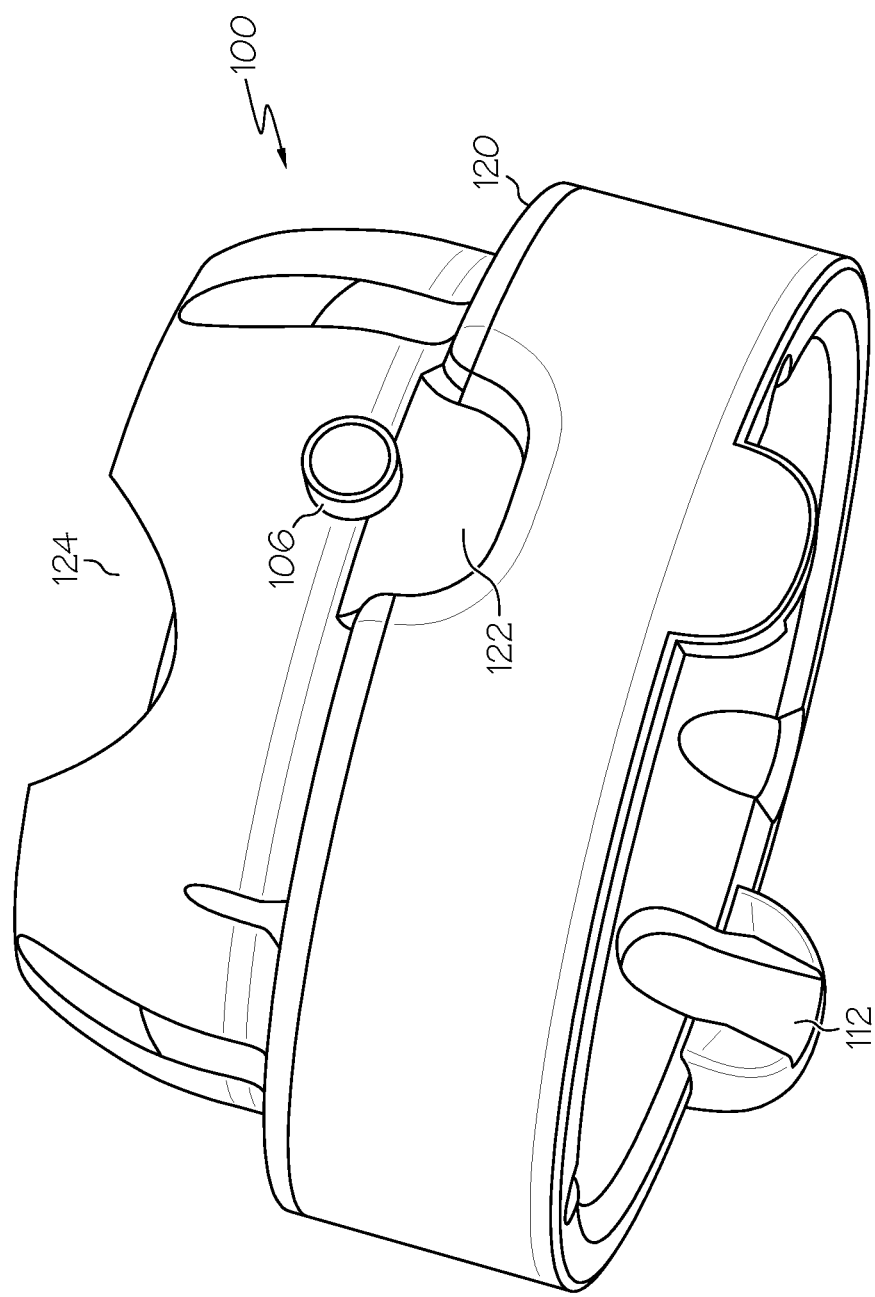
FIG. 1E is a side perspective view of one of the first and second outer links of FIG. 1A.

FIG. 1A is a side view of first and second outer links of an articulating probe of a system for performing a medical procedure according to embodiments of the present inventive concepts. FIG. 1B is a lower perspective view of the first and second outer links of FIG. 1A. FIG. 1C is a cutaway side view of the first and second outer links of FIG. 1A. FIG. 1D is a cutaway side view of the first and second outer links of FIG. 1A illustrated with the second link articulated relative to the first link. FIG. 1E is a side perspective view of one of the first and second outer links of FIG. 1A.

Referring to FIG. 1A, first and second outer links 100a, 100b (generally 100) of the articulating probe are each constructed and arranged to have a longitudinal axis 102Za, 102Zb, an articulation joint (joint formed from articulating surfaces 104 and 110 shown specifically in FIG. 1C) and motion-limiting element 106. Multiple outer links 100 are stacked and nested relative to each other. The links are configured to articulate relative to each other and are prevented from separating relative to each other by steering cables 109 (see FIG. 1B) that pass through one or more steering cable openings 108 of the multiple links 100. In the present example, three steering cable openings 108 and three cables 109 are shown (see FIG. 1B); however fewer or more steering cable openings and steering cables can be employed, depending on the application of the articulating probe.

Illustrated in FIG. 1C, the articulation joint comprises a convex articulation surface 104a of the first outer link 100a and a concave articulation surface 110b of the second outer link 100b. The convex and concave surfaces engage each other throughout a range of articulation of the second outer link 100b relative to the first outer link 100a, under control of the steering cables 109. Tension that is present in at least one of the steering cables 109, at any given time, between the proximal and distal ends of the articulating probe retain the articulating joints of the various links of the assembly in place.

Referring to the illustrations of FIGS. 1A-1C, the respective longitudinal axes 102Za, 102Zb of the first and second outer links 100a, 100b are substantially in alignment with each other, or at an angle of zero degrees with respect to each other. In this position, the second outer links 100b can be considered to be in a non-articulated position relative to the first outer link 100a. However, in the illustration of FIG. 1D, the second longitudinal axis 102Zb of the second link 100b is at a non-zero angle relative to the first longitudinal axis 102Za of the first link 100a. In this position, the second outer link 100b can be considered to be in an articulated position relative to the first outer link 100a.

Figure 2:
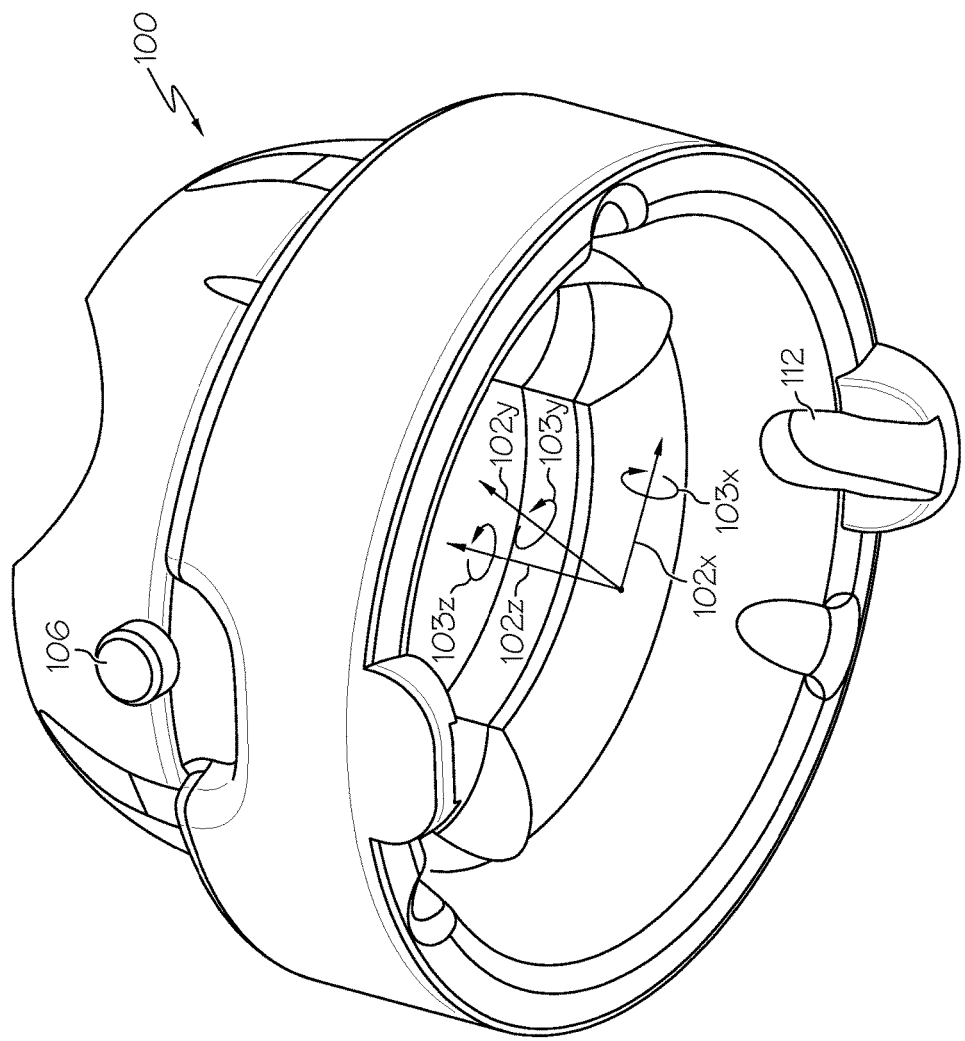
FIG. 2 is a lower perspective view of an outer link of an articulating probe of a system for performing a medical procedure according to embodiments of the present inventive concepts.

FIG. 2 is a lower perspective view of an outer link of an articulating probe of a system for performing a medical procedure according to embodiments of the present inventive concepts. In this view, first and second articulation axes 102X, 102Y of the outer link are illustrated. The first and second articulation axes 102X, 102Y are normal to each other and normal to the longitudinal axis 102Z of the outer link. Over a permitted range of articulation, a second outer link 100b neighboring a first outer link 100a will be permitted to articulate over a range of angles about the first articulation axis 102X as illustrated by arrow 103X and will be permitted to articulate over a range of angles about the second articulation axis 102Y as illustrated by arrow 103Y, relative to the first and second articulation axes of the first outer link 100a. In this manner, articulation is permitted or allowed in two degrees of freedom. Twisting or rotation of the second outer link 100b relative to a neighboring first outer link 100a in the direction illustrated by arrow 103Z is undesirable, for various reasons described herein. Embodiments of the present inventive concepts described herein include a motion-resisting assembly of any of a number of various types for limiting, mitigating or otherwise resisting rotation or twisting of a second outer link relative to a neighboring first outer link of the articulating probe assembly, or of a second inner link relative to a neighboring first inner link of the articulating probe assembly.

Returning to FIG. 1A, the first and second outer links 100a, 100b each include a motion limiting element, pin 106 (also visible in the perspective view of FIG. 1E), that operates in conjunction with a corresponding slot 112 of a neighboring link to provide a motion resisting assembly 106, 112 suitable for limiting rotation of the second link 100b relative to the first link 100a. In particular, motion resisting assembly 106, 112 is suitable for limiting rotation of the second link 100b about its longitudinal axis 102Zb relative to the longitudinal axis 102Za of the first link 100a.

At the same time, the motion resisting assembly 106, 112 operates to limit rotation of the first link 100a relative to the second link 100b. In this manner, the motion resisting assembly 106, 112 can be said to limit rotation of the first link 100a and the second link 100b relative to each other.

In some embodiments, the pin 106 extends in an outward direction from a lower portion of the convex articulation surface 104 of the outer link 100. In an embodiment where the convex articulation surface 104 is semi-spherical, the pin 106 can be positioned at, or along, an equator of the semi-spherical surface. In some embodiments, the pin 106 may be circular in cross-section to allow for pivoting of a slot 112 of a neighboring link during articulation. In other embodiments, the pin 106 can have a cross-sectional shape that is other than circular.

In some embodiments, the slot 112 can be formed in a pin extension or tab 114 that extends from a lower portion of the link 100. The slot 112 can have a width W (see FIG. 1B) that is sized to accommodate the pin 106 width. In some embodiments, the pin 106 can be permitted to slide freely along the slot 112 in a direction of extension of the slot, while limiting gaps or play of the pin 106 between the sidewalls of the slot 112. The slot 112 can have a length L that is sufficient to allow the pin 106 to slide between a range of desired articulation of neighboring links 100a, 100b. A top portion of the slot 112 can be rounded to interface with the rounded, corresponding pin 106.

In some embodiments, as illustrated in FIG. 1C, each link 100 includes two pins 106 and two pin slots 112 for mating with pins of neighboring links. Each link, however, can include a single pin 106, or more than two pins, or a single slot 112, or more than one slot 112, depending on the application. In the embodiment illustrated in FIG. 1C, the first link 100a is in alignment with the second link 100b so that their respective longitudinal axes 102Za, 102Zb are in alignment. In this non-articulated state, the first and second pins 106 are at least partially engaged with the respective first and second slots 112 of the neighboring second link 100b. In this position, the second link 100b is prevented, or otherwise limited, from rotating or twisting, about its longitudinal axis 102Zb, relative to the longitudinal axis 102Za of the first link 100a, as the first and second pins 106 are engaged with their respective mating slots 112. In particular, with any such twisting moment imparted on the second link 100b, the sidewalls of the slots 112 of the second link abut the pins 106 of the first link 100a and thus prevent the first link 100b from rotating about its longitudinal axis 102Zb. At the same time, the interaction of the pins 106 and slots 112 do not obstruct or limit articulation of the second link 100b relative to the first link 100a, for example articulation of the second link 100b about the first and second articulation axes 102x, 102y of the first link 100a (see FIG. 2). Free articulation of the second link 100b relative to the first link 100a is maintained, while mitigating or preventing undesired twisting of the second link relative to the first link.

Referring to FIG. 1D, upon further articulation of the second link 100b relative to the first link 100a, in the present embodiment, one of the pins 106-1 becomes disengaged from its corresponding slot 112-1, while the other of the pins 106-2 becomes engaged more deeply into its corresponding slot 112-2. Similarly, in this articulated position, the sidewalls of the slot 112-2 of the second link 100b interacting with the corresponding pin 106-2 of the first link 100a prevents twisting of the second link 100b about its longitudinal axis 102Zb relative to the first link 100a. At the same time, free articulation of the second link 100b relative to the first link 100a is maintained.

Referring to FIGS. 1A-1E, the links 100a, 100b each include a lower portion 126 and an upper portion 128. In some embodiments, the lower portion 126 includes the concave articulation surface 110 and the upper portion 128 includes the convex articulation surface 104 which combine to form the articulation joint. At an interface of the outer surfaces of the lower portion 126 and the upper portion 128, a shoulder 120 can be provided. The shoulder 120 of a first link 100a and a lower surface 121 of the second link 100b operate to limit the amount of articulation of the second link 100b relative to the first link 100a. For example, articulation can be limited to an angle that corresponds to the position at which the lower surface 121 of the second link 100b physically abuts the shoulder 120 of the first link 100a.

Continuing to refer to FIGS. 1A-1E, in some embodiments, a recess 122 can be formed in the shoulder 120 of the lower portion. The recess 122 can be formed to have a shape that accommodates the pin extension or tab 114. In this manner, the slot 112 of the tab 114 can engage its corresponding pin 106, while maintaining the outer profile of the links 100a, 100b so that their outer perimeters are not increased. In some embodiments, the tab 114 and corresponding recess 122 can be constructed and arranged so that they do not limit articulation of the second link 100b relative to the first link 100*a*. In other words, at the greatest degree of articulation, the shoulder 120 of the first link 100*a* makes contact with the lower surface 121 of the neighboring link 100*b* while a clearance is maintained between the tab 114 and the surface of the corresponding recess 122. In other embodiments, the tab 114 and corresponding recess 122 can be configured so that the interface of the tab 114 and recess 122 provides an articulation-limiting function, while a clearance is maintained between the shoulder 120 and corresponding lower surface 121 of the neighboring links 100*a*, 100*b*.

Continuing to refer to FIGS. 1A-1E, in some embodiments, the links 100*a*, 100*b* comprise outer links of an articulating probe having a plurality of articulating inner links and a plurality of articulating outer links. In some embodiments, recesses 124 are provided at an interface between inner regions of the outer links and corresponding outer regions of the inner links. The recesses 124 correspond to working channels of the articulating probe to allow for delivery of functional elements from the proximal end to the distal end of the articulating probe, as described herein.

In some embodiments, for example in the embodiment depicted in FIGS. 1A-1E, the convex articulation surface 104*a* of the first outer link 100*a* comprises a semi-spherical convex surface and the concave articulation surface 110 of the second outer link 100*b* comprises a semi-spherical concave surface. In some embodiments, the radius of the convex articulation surface 104*a* of the first outer link 100*a* can be the same as the radius of the concave articulation surface 110*b* of the second outer link 100*b*. In some embodiments, the radius of the convex articulation surface 104*a* of the first outer link 100*a* can be greater than the radius of the concave articulation surface 110*b* of the second outer link 100*b*. In some embodiments, the radius of the convex articulation surface 104*a* of the first outer link 100*a* can be less than the radius of the concave articulation surface 110*b* of the second outer link 100*b*.

In some embodiments, for example in the embodiment depicted in FIGS. 1A-1E, the convex articulation surface 104*a* of the first outer link 100*a* comprises a semi-spherical convex surface and the concave articulation surface 110*b* of the second outer link 100*b* comprises a semi-conical concave surface. An advantage of this configuration is that the contact region of the resulting articulation joint corresponds to a circular region. As a result, the resulting interface is less likely to bind, since the region of contact is reduced. Also, the mating properties of the convex and concave articulation surfaces can be more readily controlled, since the interface is less susceptible to variation in manufacturing process parameters such as variation in texture, material, friction, and the like. The resulting interface also allows for greater tolerance variation in the links, reducing manufacturing costs.

In one example, assuming a semi-spherical convex articulation surface, variation in the spherical diameter can affect the amount of surface contact between the convex and concave surfaces. This can result in variation of the steering forces, variation in the amount of compression between neighboring links and binding of the articulation surfaces. Assuming a semi-conical concave articulation surface, any variation in the convex surface as a result of manufacturing or use have little effect on the contact angle and location of contact between the convex and concave articulation surfaces. Variations in the size of the convex surface may have an effect on how far into the semi-conical surface the convex surface engages, but, owing to the geometry, the contact angle will be the same, despite the variations.

The angle of the semi-conical surface can be varied to accommodate tradeoffs between steerability and payload of the resulting articulating probe. The angle of the semi-conical surface controls the contact point between the convex, semi-spherical and the concave, semi-conical articulation surfaces. In general, as the contact point is lowered to a wider region of the cone, the strength of the interface, and therefore the strength of the articulating probe, is improved. As the contact point is raised to a narrower region of the cone, steerability of the articulating probe is improved.

In some embodiments, the angle of the semi-conical surface can be approximately 23°, or 46° included. This angle can be suitable when considering the combined factors of outer link geometry, material strength, and material friction properties. A range of angles were subject to testing, and compression testing indicated that the 23 degree conical provided optimal compression, in other words, the least amount of compression, as a result of where the concave conical surface comes in contact with the convex spherical mating surface, while still providing optimal friction for locking ability in a rigid state, as recorded in friction/steering test results. Steeper angles, for example a 14 degree angle, resulted in the outer links sticking or binding to each other under compression, while more gradual angles, for example, angles greater than about 23 degrees resulted in reduced locking while in a rigid state. However, with a different combination of geometry, friction and material strength, conical angles less than 23 degrees or greater than 23 degrees may be desirable.

In the embodiments depicted herein, the system of outer links 100 employ three steering cables spaced apart from each other at 120 degree intervals. The steering cables are selectively tensioned to retain the articulation surfaces of the links in a rigid position and are selectively released to allow for selective motion of the links in a limp position. Other numbers of steering cables can be employed, for example two, four, or more, and they can be spaced apart at regular angular intervals or at different angles.

Figure 3A:
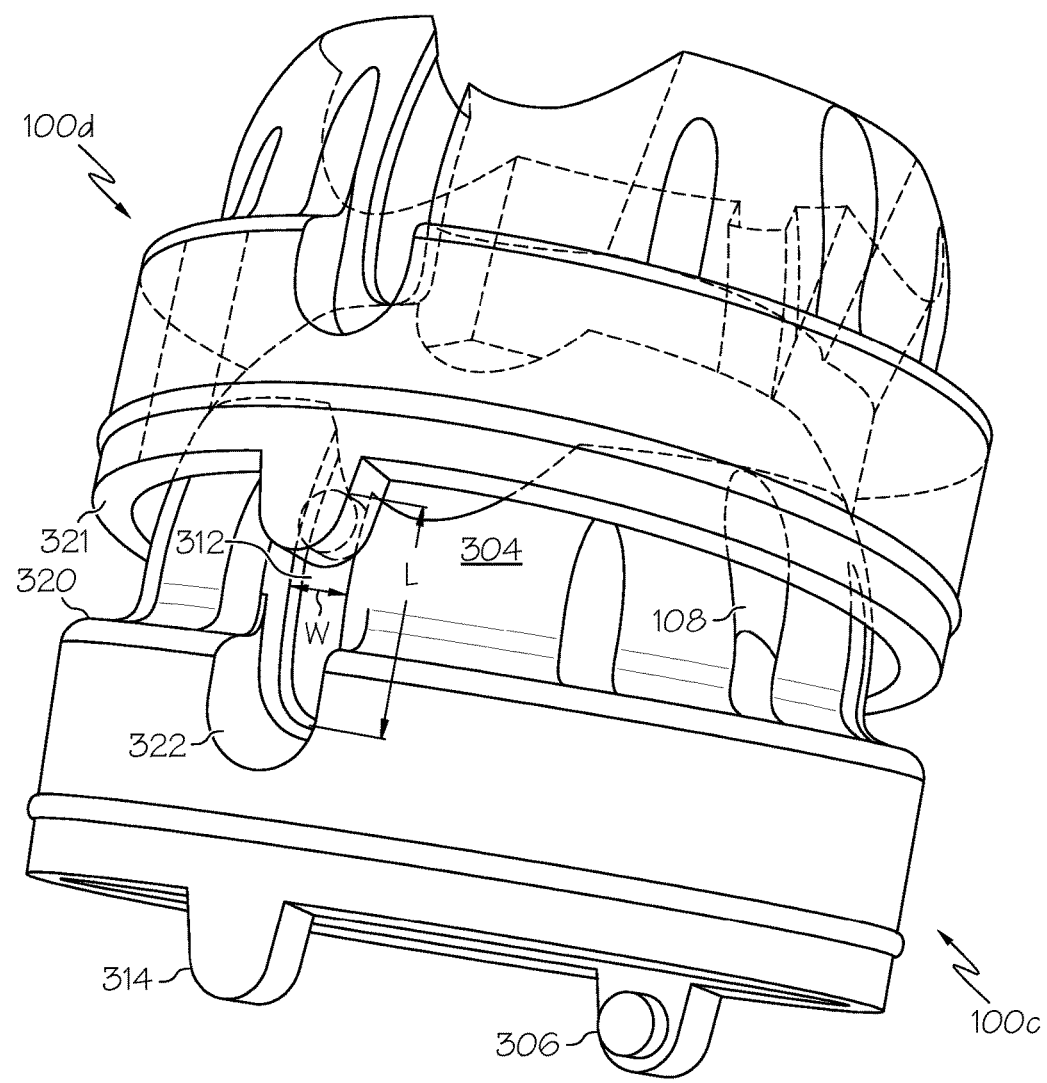
FIGS. 3A and 3B are perspective views of outer links of an articulating probe of a system for performing a medical procedure according to other embodiments of the present inventive concepts.

FIG. 3A is a perspective view of first and second outer links of an articulating probe of a system for performing a medical procedure according to other embodiments of the present inventive concepts.

Referring to FIG. 3A, in this embodiment, the motion resisting assembly comprises one or more slots 312 positioned on an external portion of the convex articulation surface 304 of the link 100*c*, 100*d*. The motion resisting assembly further comprises one or more corresponding pins 306, in this example two opposed pins, that are positioned on tabs 314 configured to engage the corresponding slots 312 of a neighboring link 100*c*, 100*d*.

In some embodiments, the convex articulation surface 304 of the links 100*c*, 100*d* is semi-spherical. In such an arrangement, the pins 306 of a neighboring second link 100*d* can be positioned such that when the neighboring links are at an articulation angle of zero, and therefore, their respective longitudinal axes are aligned, the pins 306 of the neighboring second link 100*d* are aligned with the equator of the semi-spherical convex articulation surface 304 of the first link 100*c*. The slots 312 can be oriented to extend along the outer surface of the semi-spherical convex articulation surface 304 in a direction that is along a meridian curve, or longitude curve, from the equator of the surface 304 to a pole of the surface 304. In some embodiments, the length L of the slots 312 can be extended beyond the equator of the surface 304, to accommodate articulation of the neighboring second link 100*d* relative to the first link 100*c*. In some embodiments, at a maximum articulation angle, the lower surface 321 of the second link 100*d* abuts a shoulder 320 of the first link 100*c* to limit articulation. A recess 322 formed in the shoulder 320 accommodates the tab 314 in this position, without interfering with free articulation of the second link 100*d* relative to the first link 100*c*. Alternatively, the tab 314 and corresponding recess 322 can be configured to provide an articulation-limiting function.

In the present embodiment, with any such twisting moment imparted on the second link 100*d*, the sidewalls of the slots 312 of the first link 100*c* abut the pins 306 of the second link 100*d* and thus prevent the second link 100*d* from rotating about its longitudinal axis relative to the first link 100*c*. At the same time, the interaction of the pins 306 and slots 312 do not obstruct or limit articulation of the second link 100*d* relative to the first link 100*c*, for example articulation of the second link 100*d* about the first and second articulation axes 102*x*, 102*y* of the first link 100*c* (see FIG. 2). Free articulation of the second link 100*d* relative to the first link 100*c* is maintained, while mitigating or preventing undesired twisting of the second link 100*d* relative to the first link 100*c*

In some embodiments, two pins 306 and slots 312 can be positioned on each link 100*c*, 100*d* at opposed 180 degree positions, as shown in FIG. 3A.

Figure 3B:
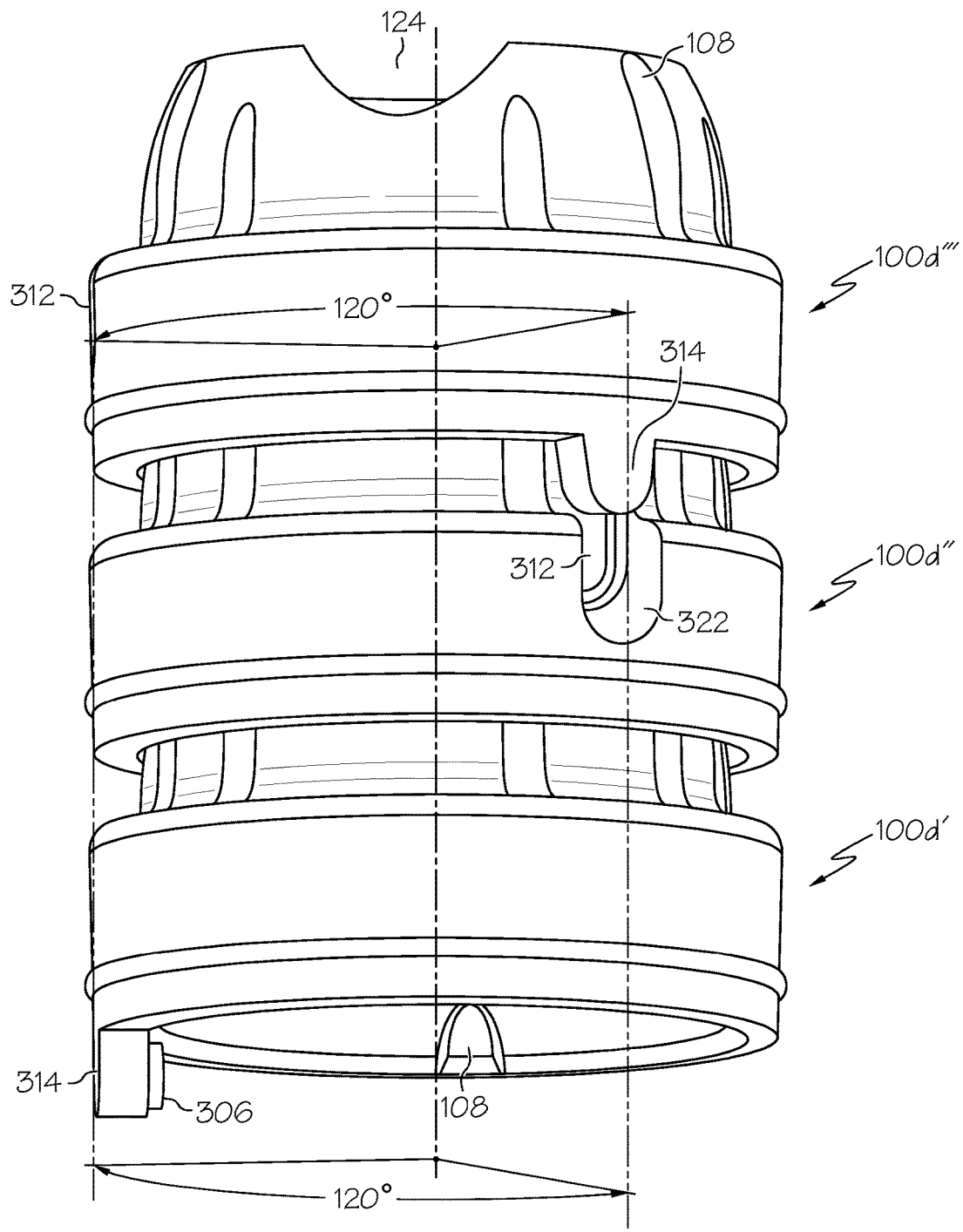

Referring to FIG. 3B, in other embodiments, a single pin 306 and a single slot 312 can be positioned on each link 100*d'*, 100*d"*, 100*d'"*. In an example embodiment, the pin 306 and slot 312 of each link 100*d'*, 100*d"*, 100*d'"* can be positioned at an angular distance of 120 degrees apart from each other about the perimeter of the link 100*d'*, 100*d"*, 100*d'"*. During assembly, each respective link 100*d'*, 100*d"*, 100*d'"*, can be seated into its respective position by rotating each link by 120 degrees relative to the neighboring link as the links progress from the proximal end to the distal end of the articulating probe. Engagement of the single pin 306 and slot 312 is sufficient for mitigating or preventing undesired twisting of the link 100*d"* relative to an adjacent link, e.g. 100' and 100'", since the pin 306 and corresponding slot 112 remain engaged throughout the range of articulation.

Figure 4:
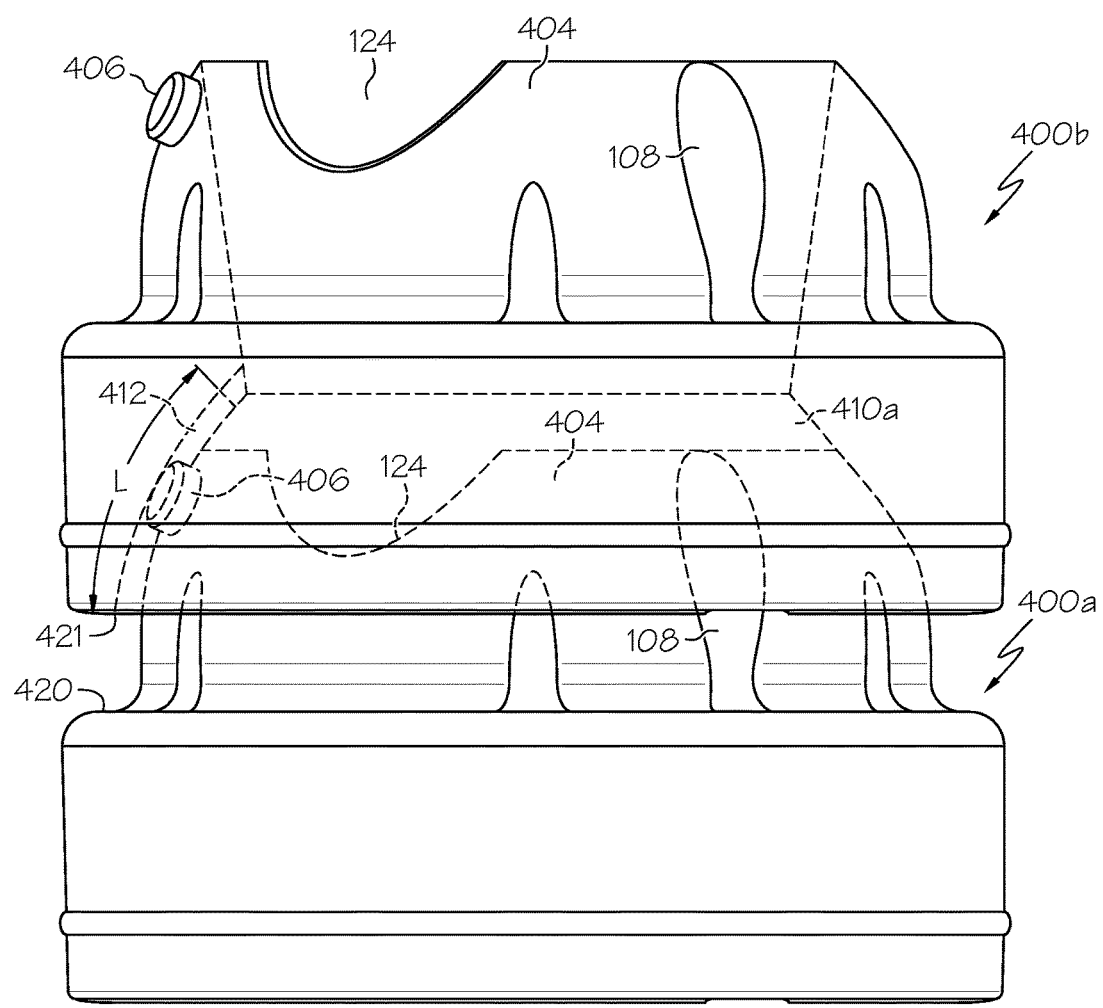
FIG. 4 is a perspective view of first and second outer links of an articulating probe of a system for performing a medical procedure according to other embodiments of the present inventive concepts.

FIG. 4 is a perspective view of first and second outer links of an articulating probe of a system for performing a medical procedure according to other embodiments of the present inventive concepts.

Referring to FIG. 4, in this embodiment, the motion resisting assembly comprises one or more pins 406 positioned on an external portion of the convex articulation surface 404 of the link 400*a*, 400*b*. The motion resisting assembly further comprises one or more corresponding slots 406 that are positioned within the concave articulation surface 410*a* and configured to engage the corresponding pins 406 of a neighboring link 400*a*, 400*b*. In the embodiment illustrated in FIG. 4, a single pin 406 and a single corresponding slot 412 are used.

In some embodiments, the convex articulation surface 404 of the links 400*a*, 400*b* is semi-spherical. In such an arrangement, the pin 406 of each link can be positioned to lie on the convex articulation surface 404 at a position above the equator of the semi-spherical convex articulation surface 404, and between the equator and the pole of the surface 404.

The slots 412 can be oriented to extend along the inner surface of the semi-spherical concave articulation surface 410*a* in a direction that is oriented along a meridian curve, or longitudinal curve, from the equator of the surface 410*a* toward a pole of the surface 410*a*. In some embodiments, the length L of the slots 412 can accommodate articulation of the neighboring second link 400*b* relative to the first link 400*a*. In some embodiments, at a maximum articulation angle, the lower surface 421 of the second link 400*b* abuts a shoulder 420 of the first link 400*a* to limit articulation.

In the present embodiment, with any such twisting moment imparted on the second link 400*b*, the sidewalls of the slot 412 of the second link 400*b* abut the pin 406 of the first link 400*a* and thus prevent the second link 400*b* from rotating about its longitudinal axis relative to the first link 400*a*. At the same time, the interaction of the pin 406 and slot 412 do not obstruct or limit articulation of the second link 400*b* relative to the first link 400*a*, for example articulation of the second link 400*b* about the first and second articulation axes 102*x*, 102*y* of the first link 400*a* (see FIG. 2). Free articulation of the second link 400*b* relative to the first link 400*a* is maintained, while mitigating or preventing undesired twisting of the second link 400*b* relative to the first link 400*a*.

Figure 5A:
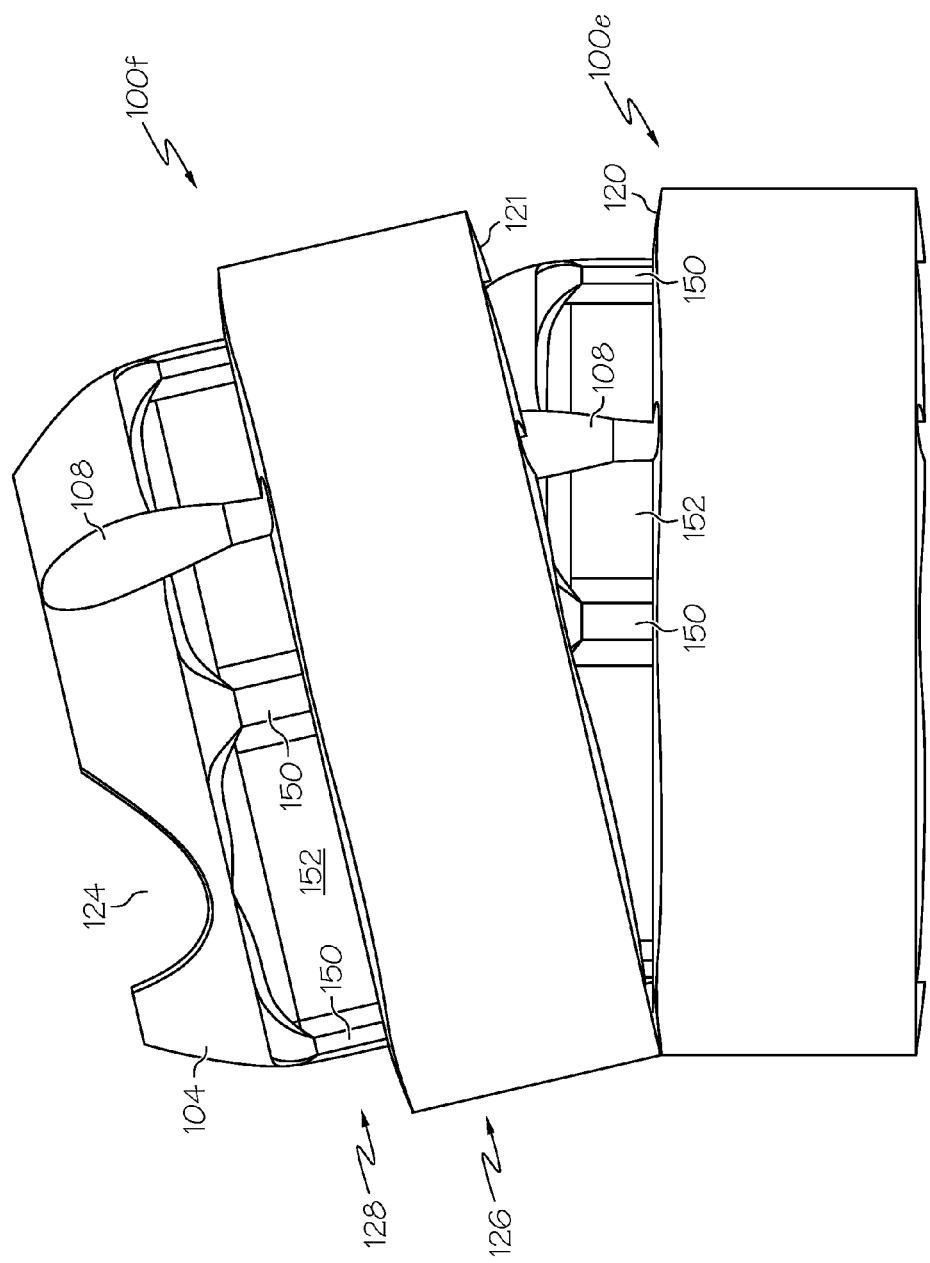
FIG. 5A is a side view of first and second outer links of an articulating probe of a system for performing a medical procedure according to other embodiments of the present inventive concepts.
Figure 5B:
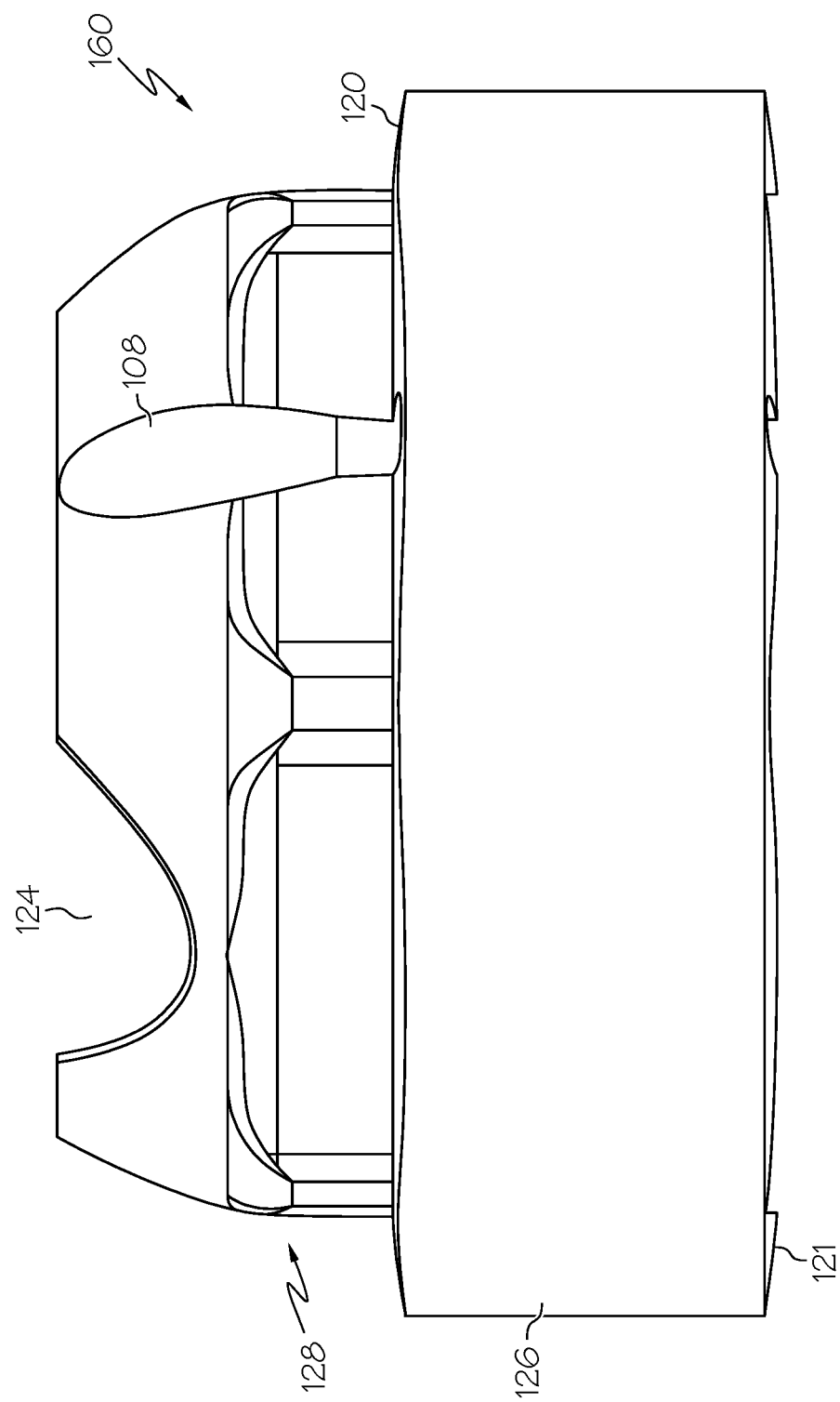
FIG. 5B is a close-up side view of one of the first and second outer links of FIG. 5A.

FIG. 5A is a side view of first and second outer links of an articulating probe of a system for performing a medical procedure according to other embodiments of the present inventive concepts. FIG. 5B is a close-up side view of one of the first and second outer links of FIG. 5A. FIG. 5C is a lower perspective view of the link of FIG. 5B.

Referring to FIGS. 5A-5C, in some embodiments, the motion resisting assembly comprises a plurality of lobes, or ribs, 150, spaced apart from each other about an outer perimeter of the convex articulation surface 104 of the link 100*e*, 100*f*. In some embodiments, the convex articulation surface 104 is semi-spherical and the plurality of lobes 150 are spaced apart about an equator region of the convex articulation surface 104. In other embodiments, the lobes 150 can be placed between the equator region and the polar region of the convex articulation surface. The lobes 150 can be linked to each other by planar outer linking surfaces 152; however, the linking surfaces can alternatively be curved or angular, depending on the application. The motion resisting assembly further comprises a plurality of recesses 154 spaced apart from each other about an inner surface of the lower portion of the concave articulation surface 110. The recesses 154 are similarly linked to each other by planar inner linking surfaces 156, which otherwise can also be curved or angular, depending on the application. The lobes 150 and outer linking surfaces 152 of a first neighboring link 100*e* are positioned to correspond with the recesses 154 and inner linking surfaces 156 of a second neighboring link 100*f*. In this manner, throughout the range of articulation of the second link 100*f* relative to the first link 100*e*, at least one of the plurality of recesses 154 and/or planar inner linking surfaces 156 remains engaged with the corresponding lobes 150 and/or outer linking surfaces 152 of the neighboring link. In some embodiments, in a position where the second link 100*f* is in position at a zero-degree articulation angle relative to the first link 100*e*, at least top portions of all lobes 150 and outer linking surfaces 152 can be in position to engage at least bottom portions of all recesses 154 and inner linking surfaces 156. On the other hand, at a position of full articulation limited by contact of the lower surface 121 of the second link 100*f* and the shoulder 120 of the first link 100*e*, such as in the example depicted in FIG. 5A, the leftmost lobes 150 and corresponding recesses 154 are fully engaged, the central lobes 150 and recesses 154 are partially engaged and the rightmost lobes 150 and recesses 154 are not engaged.

In the present embodiment, with any such twisting moment imparted on the second link 100*f*, the inner walls of the recesses 154 and inner linking surfaces 156 of the second link 100*f* abut the lobes 150 and outer linking surfaces 152 of first link 100e and thus prevent the second link 100f from rotating about its longitudinal axis. At the same time, the interaction of the recesses and lobes 154, 150 and inner and outer linking surfaces 156, 152 do not obstruct or limit articulation of the second link 100f relative to the first link 100e, for example articulation of the second link 100f about the first and second articulation axes 102x, 102y of the first link 100e (see FIG. 2). Free articulation of the second link 100f relative to the first link 100e is maintained, while mitigating or preventing undesired twisting.

Figure 6A:
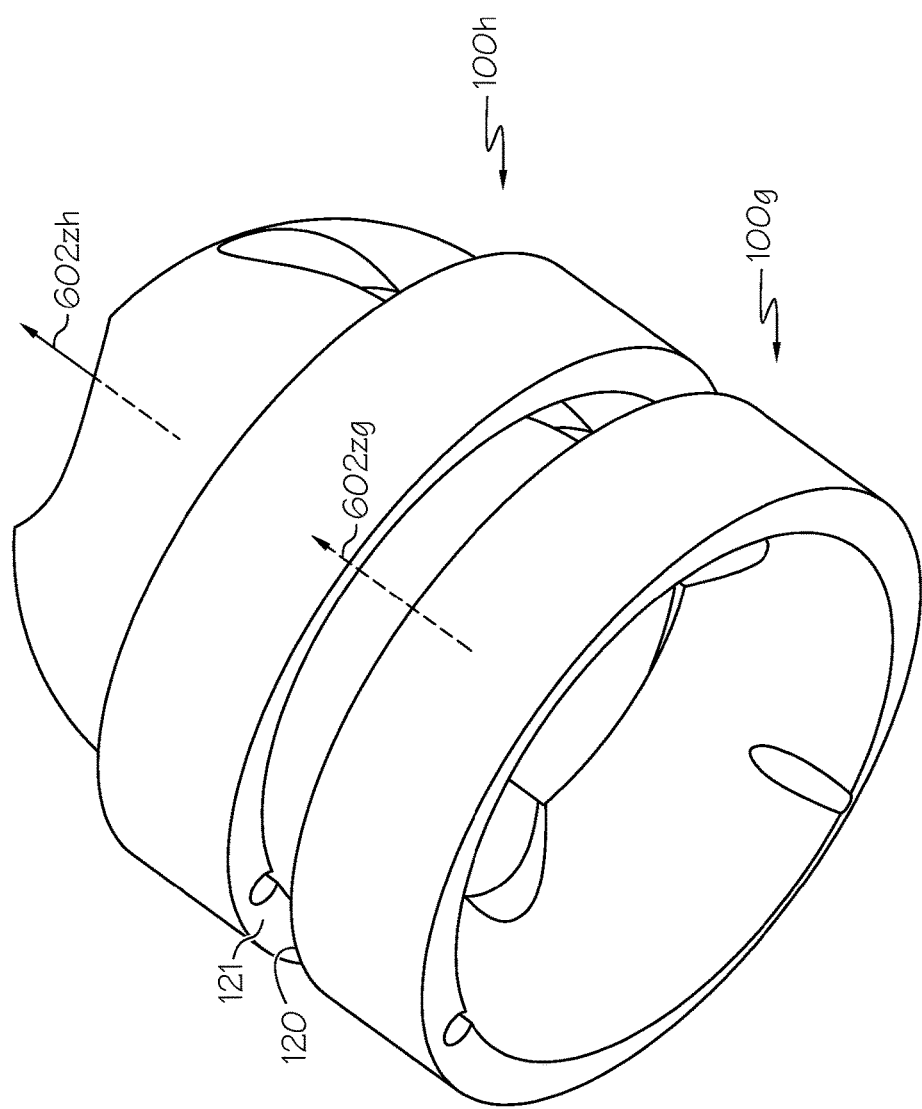
FIG. 6A is a lower perspective view of first and second outer links of an articulating probe of a system for performing a medical procedure according to other embodiments of the present inventive concepts.
Figure 6B:
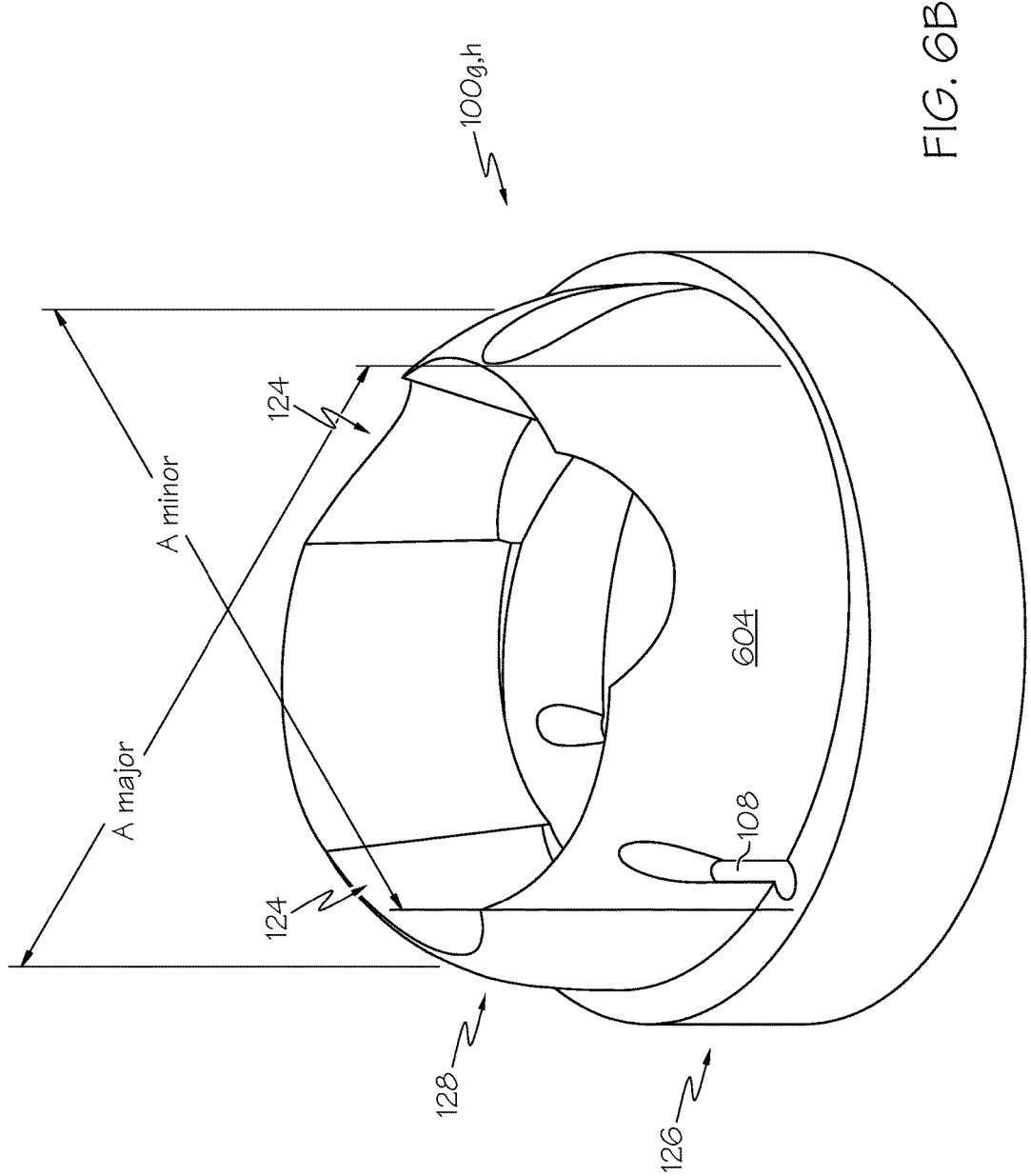
FIG. 6B is a top perspective view of one of the first and second outer links of FIG. 6A.

In the embodiment of FIGS. 5A-5C, six lobes 150 and corresponding recesses 154 are depicted so as to be evenly distributed about the links in mating hexagonal shapes. In various embodiments, any of a number of lobes 150 and recesses 154 can be employed. For example, any of two through eight, or more, lobes 150 can be employed and two through eight, or more, recesses 154 can be employed. The number of lobes 150 can be the same as, or different than the number of recesses 154. The lobes and/or recesses can be evenly distributed at angular intervals about the links or can be unevenly distributed. The outer linking surfaces 152 can be planar, or otherwise curved or angular, depending on the application. Similarly, the inner linking surfaces 156 can be planar, or otherwise curved or angular, depending on the application FIG. 6A is a lower perspective view of first and second outer links of an articulating probe of a system for performing a medical procedure according to other embodiments of the present inventive concepts. FIG. 6B is a top perspective view of one of the first and second outer links of FIG. 6A. FIG. 6C is a lower perspective view of the link of FIG. 6B.

Referring to FIGS. 6A-6C, in some embodiments, the motion resisting assembly comprises a convex first articulation surface 604 on an upper portion 128 of a first link 100g and a concave second articulation surface 610 in a lower portion of a second link 100h neighboring the first link 100g.

In some embodiments, the convex first articulation surface 604 is semi-ellipsoidal. In some embodiments, the concave second articulation surface 610 is semi-ellipsoidal. In some embodiments, the semi-ellipsoidal surface has a major axis Amajor and a minor axis Aminor in the plane of the first and second articulation axes 102x, 102y (see FIG. 2). Referring to FIGS. 6B and 6C, the major axis Amajor can have a greater length than the minor axis Aminor for both the convex first articulation surface 604 and the concave second articulation surface 610.

Interaction of the corresponding convex and concave semi-ellipsoidal articulation surfaces 604, 610 of the neighboring links permit free articulation of the second link 100h relative to the first link 100g. The articulation can be limited for example, by positioning of the lower surface 121 of the second link 100h relative to the shoulder 120 of the first link 100g, as described herein in connection with various other embodiments.

In the present embodiment, with any such twisting moment imparted on the second link 100h, the elongated shapes of the mating semi-ellipsoidal surfaces 604, 610 of the neighboring links prevent the second link 100h from rotating about its longitudinal axis 602Zh relative to the longitudinal axis 602Zg of the first link 100g. At the same time, the interaction of the semi-ellipsoidal surfaces 604, 610 does not obstruct or limit articulation of the second link 100h relative to the first link 100g, for example articulation of the second link 100h about the first and second articulation axes 102x, 102y of the first link 100g (see FIG. 2). Free articulation of the second link 100h relative to the first link 100g is maintained, while mitigating or preventing undesired twisting of the second link relative to the first link.

Figure 7A:
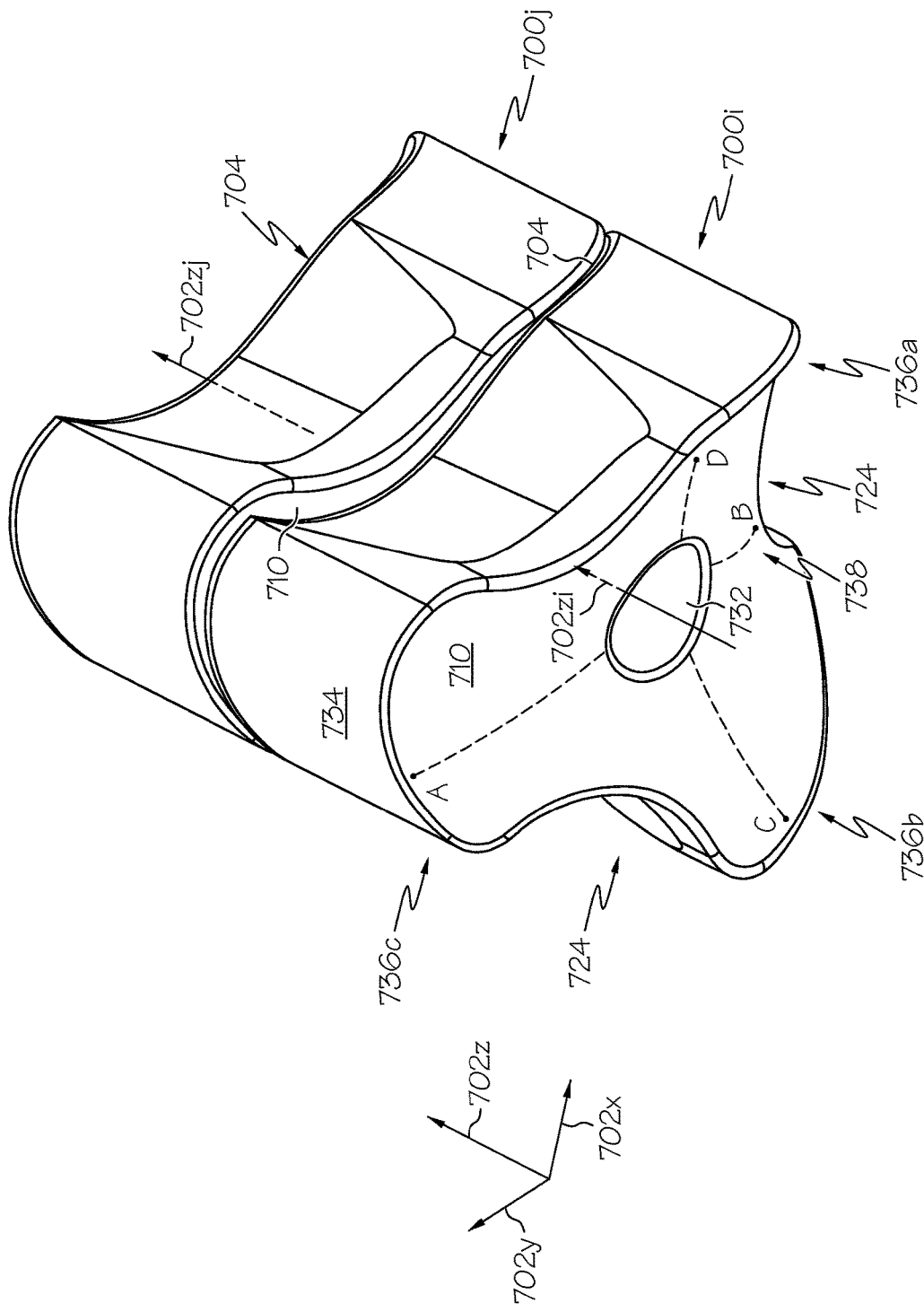
FIG. 7A is a lower perspective view of first and second inner links of an articulating probe of a system for performing a medical procedure according to other embodiments of the present inventive concepts.
Figure 7B:
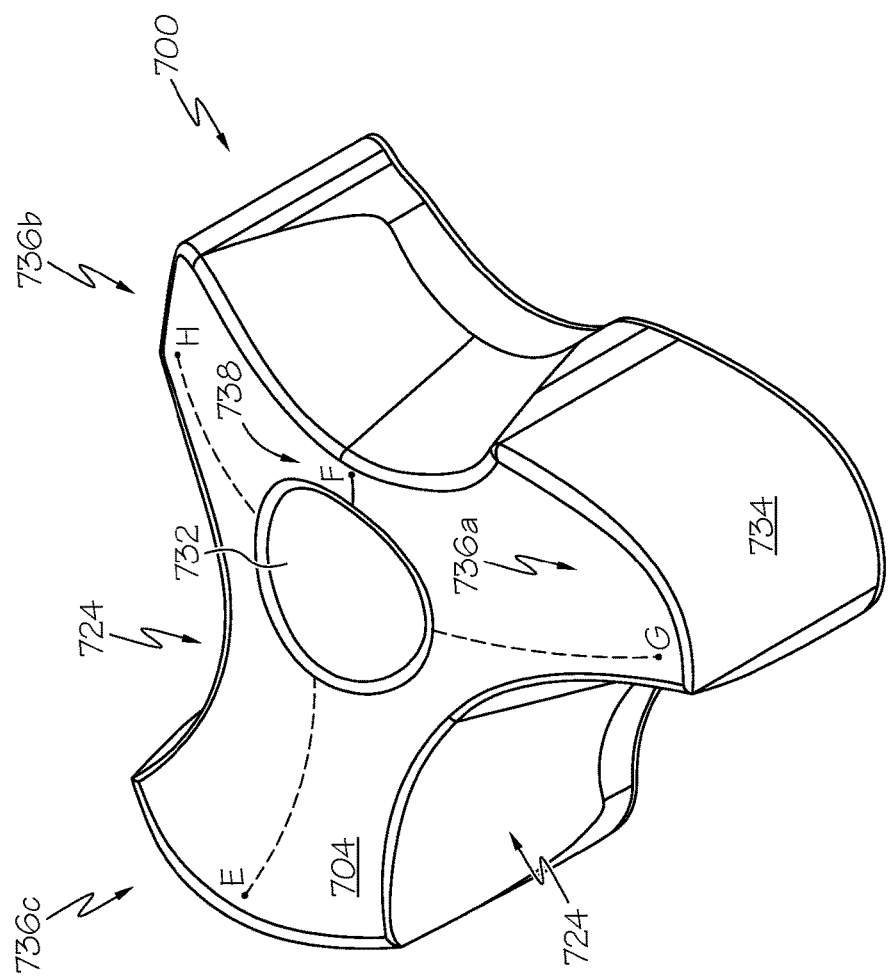
FIG. 7B is a top perspective view of one of the first and second inner links of FIG. 7A.

FIG. 7A is a lower perspective view of first and second inner links of an articulating probe of a system for performing a medical procedure according to other embodiments of the present inventive concepts. FIG. 7B is a top perspective view of one of the first and second inner links of FIG. 7A.

Referring to FIGS. 7A-7B, in some embodiments, the motion resisting assembly comprises a first articulation surface 704 on an upper surface of a first link 700i and a second articulation surface 710 on a lower surface of a second link 700j neighboring the first link 700i.

In the present example of FIGS. 7A and 7B, the first and second links 700i, 700j comprise inner links of the articulating probe. The first and second inner links 700i, 700j are configured to be positioned within the longitudinal openings present in the arrangement of outer links.

In some embodiments, the first and second links 700i, 700j (generally 700) include a central cable opening 732 that passes through the links 700 in a longitudinal direction of the links 700 along their respective longitudinal axes 702Zi, 702Zj. The cable opening 732 is configured to receive an operating cable for the inner mechanism of the articulating probe. In some embodiments, the outermost surface portions 734 of the first and second links lie on a circle. In some embodiments recesses 724 can be provided to accommodate working channels of the articulating probe that are formed between the inner regions of the outer links and outer regions of the inner links, as described herein. In a case where three working channel recesses 724 are present, then the links are generally shaped to have three lobe regions 736a-c surrounding the cable opening 732.

In some embodiments, the first articulation surface 704 comprises convex features and concave features. For example, referring to FIG. 7B, the first articulation surface 704 is convex in profile between points G and H on the surface 704 between the first and second lobes 736a, 736b. At the same time, the first articulation surface 704 is concave in profile between points E and F on the surface 704 between the third lobe 736c and the saddle region 738 between the first and second lobes 736a, 736b.

Similarly, the second articulation surface 710, as shown in FIG. 7A comprises concave features and convex features that correspond with those of the first articulation surface 704 of a neighboring link. In particular, the second articulation surface 710 is concave in profile between points C and D on the surface 710 between the first and second lobes 736a, 736b. At the same time, the second articulation surface 710 is convex in profile between points A and B on the surface 710 between the third lobe 736c and the saddle region 738 between the first and second lobes 736a, 736b.

Accordingly, the convex features of the first articulation surface 704 mate with, or otherwise interface with, the concave features of the second articulation surface 710 of a neighboring link. Similarly, the concave features of the first articulation surface 704 mate with, or otherwise interface with, the convex features of the second articulation surface 710 of a neighboring link.

Interaction of the corresponding convex and concave features of the first and second articulation surfaces 704, 710 of the neighboring links permit free articulation of the second link 700j relative to the first link 700i. For example, the concave feature between points C and D of the second articulation surface interacting with the corresponding feature on the neighboring first articulation surface permits free articulation in a first plane; while the convex feature between points A and C of the second articulation surface interacting with the corresponding feature on the neighboring first articulation surface permits free articulation in a second plane.

In the present embodiment, with any twisting moment imparted on the second link 700*j*, the opposed convex and concave features of the first and second articulation surfaces 704, 710 prevent the second link 700*j* from rotating about its longitudinal axis 702Zj relative to the longitudinal axis 702Zi of the first link 700*i*, or otherwise limit or mitigate such rotation. At the same time, the interaction of the opposed convex and concave features does not obstruct or limit articulation of the second link 700*j* relative to the first link 700*i*, for example articulation of the second link 700*j* about the first and second articulation axes 702*x*, 702*y* of the first link 700*i*. Free articulation of the second link 700*j* relative to the first link 700*i* is maintained, while mitigating or preventing undesired twisting of the second link relative to the first.

The inventive concepts of the present embodiment including opposed and mating convex and concave features is not only applicable to inner links 700, but also can be applied to the outer links 100 of the articulating probe.

FIG. 8A-8C are top views of first and second outer links of an articulating probe of a system for performing a medical procedure according to other embodiments of the present inventive concepts.

Referring to the embodiment of FIG. 8A, first magnets 802*k* are positioned about the shoulder 120 of a first link 800*k*. The first magnets 802*k* can be positioned at regular angular intervals about the shoulder 120. In the present example embodiment, a 90 degree interval is illustrated. Similarly, second magnets 802*l* are positioned about the lower surface 121 of a second link 800*l* to correspond with those of the first link. In some examples, the ends of the first magnets 802*k* positioned on the shoulder 120 of the first link 800*k* have a first polarity, for example South (S), and ends of the second magnets 802*l* positioned on the lower surface 121 of the second link 800*l* have a second polarity, for example, North (N). In other embodiments, mating pairs of the first and second magnets 802*k*, 802*l* can be selected so as to have opposite polarities, and the polarities of all magnets of a given link do not need to have the same orientation.

Referring to the embodiment of FIG. 8B, first magnets 802*m* are positioned about the convex first articulating surface 804 of a first link 800*m*. The first magnets 802*m* can be positioned at regular angular intervals about first articulating surface 804. In the present example embodiment, a 90 degree interval is illustrated. Similarly, second magnets 802*n* are positioned about the concave second articulating surface 810 of a second link 800*n* to correspond with those of the first link 800*m*. In some examples, the first magnets 802*m* positioned on the first link 800*m* have a first polarity, for example South (S), and the second magnets 802*n* positioned on the second link 800*n* have a second polarity, for example, North (N). In other embodiments, mating pairs of the first and second magnets 802*m*, 802*n* can be selected so as to have opposite polarities, and the polarities of all magnets of a given link do not need to have the same orientation.

Referring to the embodiment of FIG. 8C, first magnetic strips 802*p* are positioned circumferentially about the convex first articulating surface 804 of a first link 800*p*. The first magnetic strips 802*p* can be positioned at regular angular intervals about first articulating surface 804. In the present example embodiment, two strips at a 180 degree interval are illustrated. Similarly, second magnetic strips 802*q* are positioned about the concave second articulating surface 810 of a second link 800*q* and are oriented to correspond with those of the first link 800*p*. In some examples, the first magnetic strips 802*p* positioned on the first link 800*p* have a first polarity, for example South (S), and the second magnetic strips 802*q* positioned on the second link 800*q* have a second polarity, for example, North (N). In other embodiments, mating pairs of the first and second magnets 802*p*, 802*q* can be selected so as to have opposite polarities, and the polarities of all magnets of a given link do not need to have the same orientation.

In some embodiments, the first and second magnets are positioned so as to magnetically engage each other over a range of articulation angles of the second link relative to the first link. The magnetic engagement between the magnets of the neighboring links permits articulation of the second link relative to the first link. The articulation can be limited for example, by positioning of the lower surface 121 of the first link relative to the shoulder 120 of the second link, as described herein in connection with various other embodiments.

In the present embodiments of FIGS. 8A-8C, with any such twisting moment imparted on the second link, the magnetic interaction of the neighboring links prevent the second link from rotating about its longitudinal axis relative to the longitudinal axis of the first link, or otherwise limit or mitigate such rotation. At the same time, the magnetic interaction does not obstruct or limit articulation of the second link relative to the first link. Free articulation of the second link relative to the first link is maintained, while mitigating or preventing undesired twisting of the second link relative to the first. The embodiments illustrated in FIGS. 8A-8C can be employed in connection with any of the other embodiments described herein to further restrict or limit twisting of the links.

In the present example embodiment, the magnets are illustrated as being applied to outer links of the articulating probe, however, the principles of this concept of the invention are equally applicable to inner links, as well.

FIG. 9 is a cross-sectional view of an inner link and an outer link including an anti-twist member positioned therebetween, in accordance with embodiments of the present inventive concepts.

Referring to FIG. 9, an articulating probe includes an assembly of outer links 100*r* having a central opening. An assembly of inner links 700*s* is positioned through the central opening of the inner links. As described herein the plurality of outer links 100*r* have recesses 124 on their inner sidewalls and the plurality of inner links 700*s* have recesses 724 on their outer sidewalls. Together, the opposed recesses 124, 724 form working channels for the articulating probe for the purposes described herein, and for other purposes.

An anti-twist member 942 is positioned in at least one of the working channels 125. In some embodiments, the anti-twist member comprises a tube-shaped member that is hollow or solid in cross-section. In other embodiments, the anti-twist member 942 comprises a flexible material that permits articulation of neighboring inner links and articulation of neighboring outer links. At the same time, the tube can exhibit strength or rigidity when subjected to a twisting motion between neighboring links. In some embodiments, the anti-twist member 942 can be configured to extend along an entire length, or nearly the entire length, of the working channel 125 of the articulating probe, from its proximal to distal end. In some embodiments, the anti-twist member 942 can be segmented so that it extends through portions of the working channel 125. In some embodiments, the anti-twist member 942 can be affixed to a recess 724 of the inner link 700s or a recess 124 of the outer link 100r. In some embodiments, the anti-twist member 942 can be affixed to both a recess 724 of the inner link 700s and a recess 124 of the outer link 100r.

In some embodiments, the tube-shaped anti-twist member 942 can be fixed at its proximal and distal ends. The torsional rigidity of the anti-twist member 942 will determine the degree to which it prevents twisting.

In the present embodiments of FIG. 9, with any such twisting moment imparted on a second link neighboring a first link, the presence of the anti-twist member prevents the second link from rotating about its longitudinal axis relative to the longitudinal axis of the first link. At the same time, the anti-twist member does not obstruct or limit, or minimally obstructs or limits, articulation of the second link relative to the first link. Free articulation of the second link relative to the first link is maintained, while mitigating or preventing undesired twisting. The embodiments illustrated in FIG. 9 can be employed in connection with any of the other embodiments described herein to further restrict or limit twisting of the links.

As described herein, the systems and methods of the present inventive concepts prevent, mitigate, or otherwise restrict, torsional rotation, or twisting, of links in a system of links in a highly articulated robotic system. The systems and methods can be applied to both an inner link mechanism and an outer link mechanism of the robotic system. In some embodiments, rotation of a second link relative to a first link can be limited to about 1 degree of rotation. Other rotational limit amounts are equally applicable, depending on the configuration, and the inventive concepts are not limited thereto.

While the present inventive concepts have been particularly shown and described above with reference to exemplary embodiments thereof, it will be understood by those of ordinary skill in the art, that various changes in form and detail can be made without departing from the spirit and scope of the present inventive concepts described and defined by the following claims.

What is claimed is:

1. An articulating probe, comprising:
    a first mechanism comprising:
        a first link comprising a first longitudinal axis, a first articulation surface and a first motion limiting element;
        a second link comprising a second longitudinal axis, a second articulation surface and a second motion limiting element;
        an articulation joint comprising the first articulation surface and the second articulation surface and constructed and arranged to allow two degree-of-freedom articulation of the second link relative to the first link; and
        a motion resisting assembly comprising the first motion limiting element and the second motion limiting element, wherein the motion resisting assembly is constructed and arranged to resist rotation of the second link about the second longitudinal axis; and
    a second mechanism comprising:
        a third link comprising a third longitudinal axis and a third articulation surface;
        a fourth link comprising a fourth longitudinal axis and a fourth articulation surface;
        an articulation joint comprising the third articulation surface and the fourth articulation surface and constructed and arranged to allow at least two degree of freedom articulation of the fourth link relative to the third link, wherein the first mechanism and the second mechanism extend in a longitudinal direction, wherein a link of one of the first and second mechanisms has an opening having an inner width greater than a greatest outer width of a link of the other of the first and second mechanisms, and wherein the link of the other of the first and second mechanisms extends through the opening of the link of the one of the first and second mechanisms and an entire length of the link of the other of the first and second mechanisms is movable in a longitudinal direction through the opening of the link of the one of the first and second mechanisms.

2. The articulating probe of claim 1 wherein the first mechanism comprises an inner link mechanism of the articulating probe and wherein the second mechanism comprises an outer link mechanism of the articulating probe.

3. The articulating probe of claim 1 wherein the first mechanism comprises an outer link mechanism of the articulating probe and wherein the second mechanism comprises an inner link mechanism of the articulating probe.

4. The articulating probe of claim 1
    wherein the third link further comprises a third motion limiting element;
    wherein the fourth link further comprises a fourth motion limiting element; and
    wherein the second mechanism further comprises a motion resisting assembly comprising the third motion limiting element and the fourth motion limiting element, wherein the motion resisting assembly is constructed and arranged to resist rotation of the fourth link about the fourth longitudinal axis.

5. The articulating probe of claim 1 wherein the first motion limiting element comprises at least one projecting member and the second motion limiting element comprises at least one receiving region constructed and arranged to receive the at least one projecting member.

6. The articulating probe of claim 5 wherein the projecting member comprises a pin and the receiving region comprises a slot.

7. The articulating probe of claim 5 wherein the projecting member comprises a rib and the receiving region comprises a recess.

8. The articulating probe of claim 5 wherein the projecting member comprises multiple projecting members and the receiving member comprises multiple receiving regions.

9. The articulating probe of claim 8 wherein the multiple projecting members are distributed evenly about the first link at equal angular intervals.

10. The articulating probe of claim 1 wherein the first motion limiting element comprises a pin and wherein the second motion limiting element comprises a slot and wherein the pin of the first link engages the slot of the second link.

11. The articulating probe of claim 1
    wherein the first motion limiting element comprises a pin;
    wherein the second motion limiting element comprises a slot;
    wherein the pin of the first link engages the slot of the second link; and
    wherein the pin of the first link interfaces with sidewalls of the slot of the second link to resist the rotation of the first link relative to the second link.

12. The articulating probe of claim 1 wherein the first motion limiting element comprises first and second pins and wherein the second motion limiting element comprises first and second corresponding slots and wherein over a range of articulation motion of the second link relative to the first link, at least one of the first and second pins is at least partially engaged with the corresponding at least one of the first and second slots.

13. The articulating probe of claim 1 wherein the first motion limiting element comprises at least one rib and wherein the second motion limiting element comprises at least one recess and wherein over a range of articulation motion of the second link relative to the first link, the at least one rib is at least partially engaged with the at least one recess.

14. The articulating probe of claim 1 wherein the first articulation surface comprises a convex surface and wherein the second articulation surface comprises a concave surface.

15. The articulating probe of claim 14 wherein the convex, first articulation surface comprises a semi-spherical surface.

16. The articulating probe of claim 14 wherein the concave, second articulation surface comprises a semi-spherical surface.

17. The articulating probe of claim 1
wherein the first articulation surface comprises a convex, semi-ellipsoidal surface;
wherein the second articulation surface comprises a concave, semi-ellipsoidal surface;
wherein the convex, semi-ellipsoidal, first articulation surface of the first link comprises the first motion limiting element; and
wherein the concave, semi-ellipsoidal, second articulation surface of the second link comprises the second motion limiting element.

18. The articulating probe of claim 1
wherein the first articulation surface comprises convex and concave regions;
wherein the second articulation surface comprises concave and convex regions that correspond to the convex and concave regions of the first articulation surface;
wherein the first articulation surface of the first link comprises the first motion limiting element; and
wherein the second articulation surface of the second link comprises the second motion limiting element.

19. The articulating probe of claim 1
wherein the first motion limiting element comprises a first magnet;
wherein the second motion limiting element comprises a second magnet, and
wherein the first and second magnets are positioned on the first and second links respectively so as to magnetically engage each other.

20. The articulating probe of claim 19
wherein the first magnet comprises multiple first magnets and wherein the second magnet comprises multiple second magnets and
wherein the multiple first and second magnets are positioned about the longitudinal axes of the respective first and second links at regular angular intervals.

21. The articulating probe of claim 19
wherein the first magnet is positioned on the first articulation surface and the second magnet is positioned on the second articulation surface; and
wherein the first and second magnets are aligned relative to each other so as to magnetically engage each other.

22. The articulating probe of claim 1 further comprising:
at least one steering cable opening through the first link and the second link extending in a direction that is parallel to the respective first and second longitudinal axes; and
at least one steering cable corresponding to links in the first mechanism that is selectively tensioned to retain the first and second articulation surfaces of the first and second links in physical contact and selectively released to allow for selective motion of the second link relative to the first link.

23. The articulating probe of claim 22 wherein the at least one steering cable opening comprises multiple steering cable openings and wherein the at least one steering cable comprises multiple steering cables.

24. The articulating probe of claim 1 wherein:
the first link further comprises a first articulation axis and a second articulation axis, the first and second articulation axes normal to each other and normal to the first longitudinal axis of the first link;
the second link further comprises a first articulation axis and a second articulation axis, the first and second articulation axes normal to each other and normal to the second longitudinal axis of the second link; and
the two-degree-of-freedom articulation of the second link relative to the first link comprises angular movement of the second link about the first and second articulation axes of the first link.

* * * * *